United States Patent
Hu et al.

(10) Patent No.: US 11,419,584 B2
(45) Date of Patent: Aug. 23, 2022

(54) DEVICES, SYSTEMS, AND METHODS FOR DIAGNOSIS OF PULMONARY CONDITIONS THROUGH DETECTION OF B-LINES IN LUNG SONOGRAPHY

(71) Applicant: Tokitae LLC, Bellevue, WA (US)

(72) Inventors: Liming Hu, Kent, WA (US); Courosh Mehanian, Redmond, WA (US); Benjamin K. Wilson, Snoqualmie, WA (US); Xinliang Zheng, Issaquah, WA (US)

(73) Assignee: TOKITAE, LLC, Bellevue, WA (US)

( * ) Notice: Subject to any disclaimer, the term of this patent is extended or adjusted under 35 U.S.C. 154(b) by 1005 days.

(21) Appl. No.: 15/969,977

(22) Filed: May 3, 2018

(65) Prior Publication Data

US 2019/0000425 A1 Jan. 3, 2019

Related U.S. Application Data

(60) Provisional application No. 62/525,952, filed on Jun. 28, 2017.

(51) Int. Cl.
| | |
|---|---|
| *A61B 8/00* | (2006.01) |
| *A61B 8/08* | (2006.01) |
| *G06T 7/00* | (2017.01) |
| *A61B 5/08* | (2006.01) |
| *A61B 8/14* | (2006.01) |

(52) U.S. Cl.
CPC .............. *A61B 8/5269* (2013.01); *A61B 8/08* (2013.01); *A61B 8/5223* (2013.01); *G06T 7/0012* (2013.01); *A61B 5/08* (2013.01); *A61B 8/14* (2013.01); *A61B 8/565* (2013.01); *G06T 2207/10016* (2013.01); *G06T 2207/10132* (2013.01); *G06T 2207/30061* (2013.01)

(58) Field of Classification Search
CPC .... A61B 5/08; A61B 8/08; A61B 8/14; A61B 8/5223; A61B 8/5269; A61B 8/565; G06T 2207/10016; G06T 2207/10132; G06T 2207/20076; G06T 2207/20081; G06T 2207/20084; G06T 2207/20104; G06T 2207/20132; G06T 2207/30061; G06T 2207/30064; G06T 7/0012; G06T 7/0016
See application file for complete search history.

(56) References Cited

U.S. PATENT DOCUMENTS

| | | |
|---|---|---|
| 2008/0119735 A1 | 5/2008 | Lin et al. |
| 2010/0125202 A1 | 5/2010 | Lee et al. |
| (Continued) | | |

FOREIGN PATENT DOCUMENTS

| | | |
|---|---|---|
| KR | 1020150002932 A | 1/2015 |
| WO | 2015048767 A1 | 4/2015 |
| WO | 2016046140 A1 | 3/2016 |

OTHER PUBLICATIONS

Corradi et al., "Computer Aided Quantitative Ultrasonography for Detection of Pulmonary Edema in Mechanically Ventilated Cardiac Surgery Patients", Chest, Sep. 2016 (Year: 2016).*

(Continued)

*Primary Examiner* — Christopher L Cook
(74) *Attorney, Agent, or Firm* — AEON Law, PLLC; Adam L. K. Philipp; Shan Liao

(57) ABSTRACT

One or more implementations allow for detecting B-lines in ultrasound video and images for diagnostic purposes through analysis of Q-mode images for B-line detection.

8 Claims, 44 Drawing Sheets

(56) References Cited

U.S. PATENT DOCUMENTS

| | | |
|---|---|---|
| 2013/0197370 A1 | 8/2013 | Burlina et al. |
| 2015/0150503 A1 | 6/2015 | Pamnani et al. |
| 2015/0371379 A1* | 12/2015 | Averikou ............. A61B 8/5284 |
| | | 382/128 |
| 2017/0071577 A1 | 3/2017 | Seo et al. |
| 2017/0086790 A1 | 3/2017 | Halmann et al. |
| 2017/0135672 A1* | 5/2017 | Pelissier ............. G01S 7/52033 |

OTHER PUBLICATIONS

Peng et al.; "Classification of Pulmonary Emphysema in CT Images Based on Multi-Scale Deep Convolutional Neural Networks"; ICIP; 2018; pp. 3119-3123; IEEE.

Peng et al.; "Joint Weber-Based Rotation Invariant Uniform Local Ternary Pattern For Classification of Pulmonary Emphysema in CT Images"; ICIP; 2017; pp. 2050-2054; IEEE.

Peng et al.; "Multi-scale Residual Network with Two Channels of Raw CT Image and Its Differential Excitation Component for Emphysema Classification"; DLMIA 2018/ML-CDS 2018; LNCS 11045; pp. 36-46: Springer Nature Switzerland AG 2018.

PCT International Search Report; International App. No. PCT/US2018/039063; dated Oct. 19, 2018; pp. 1-4.

Extended European Search Report and Opinion, EP Application No. 18825472.6, dated Feb. 23, 2021, 6 pages.

Moshavegh et al., "Novel Automatic Detection of Pleura and B-Lines (Comet-Tail Artifacts) on In Vivo Lung Ultrasound Scans", SPIE Medical Imaging, 2016.

\* cited by examiner

HORIZONTAL Q-MODE MAP GENERATION
X-Axis: Frame; Y-Axis: Location; Origin: Top-Left Vertical Q mode at different depth ranges
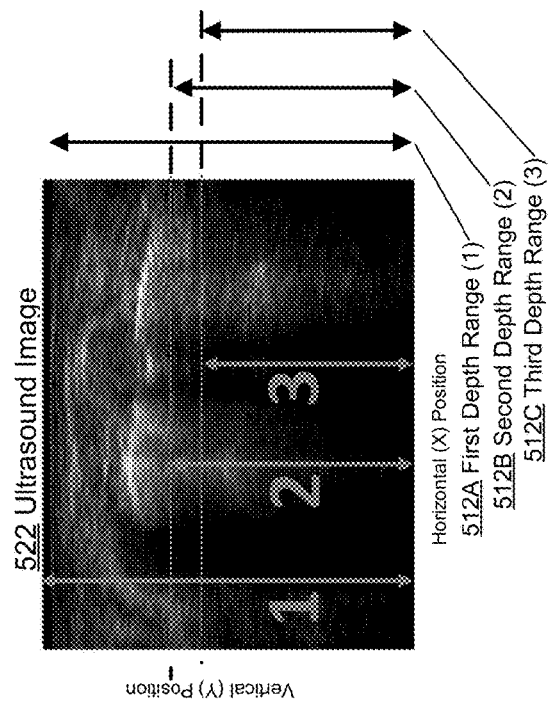
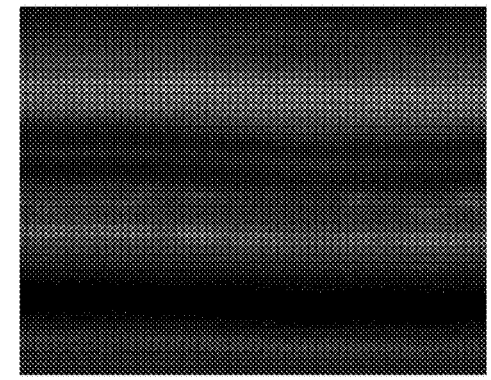
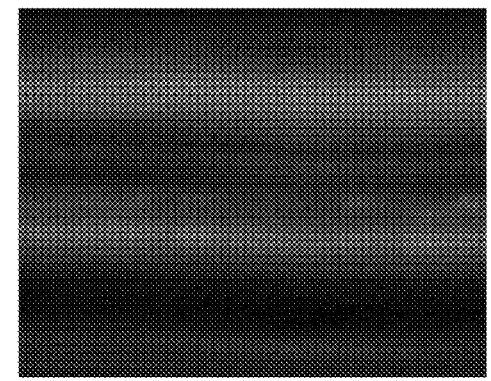
FIG. 5B

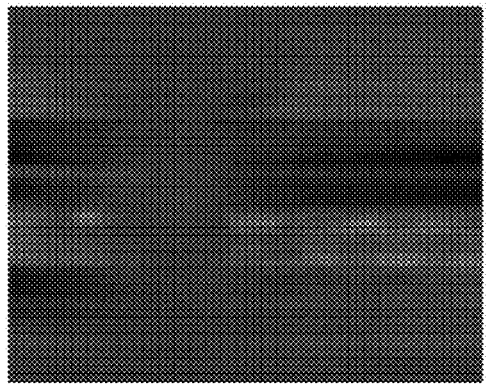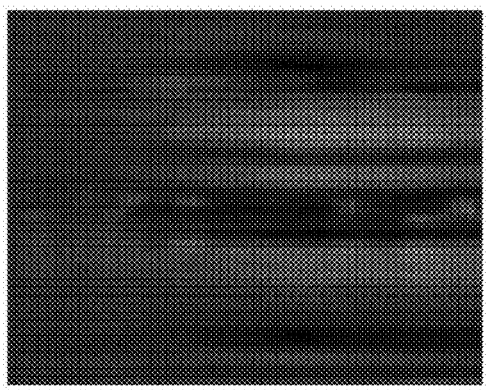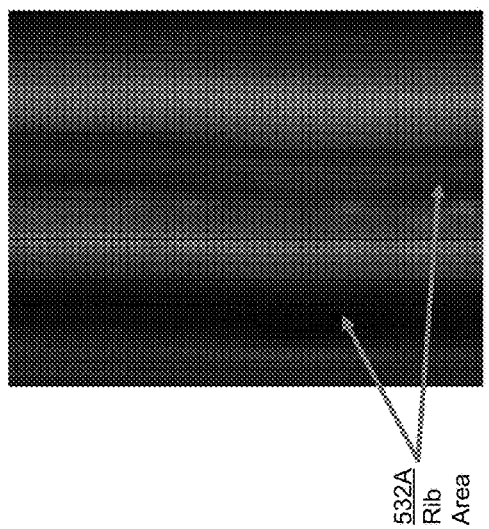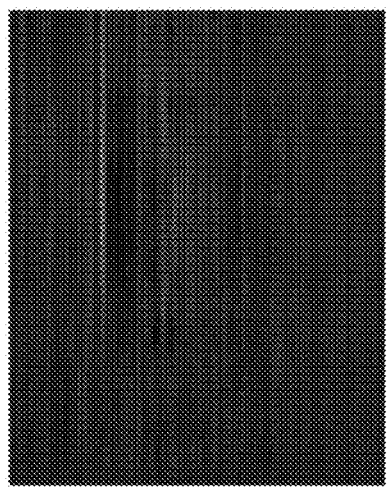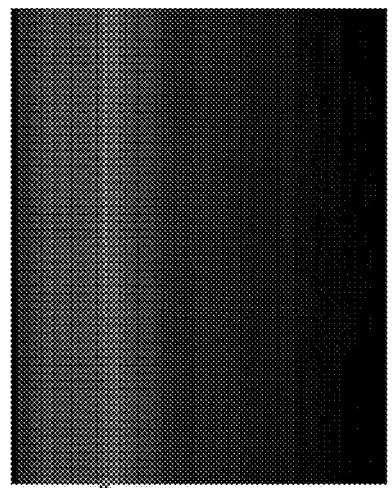
FIG. 5C

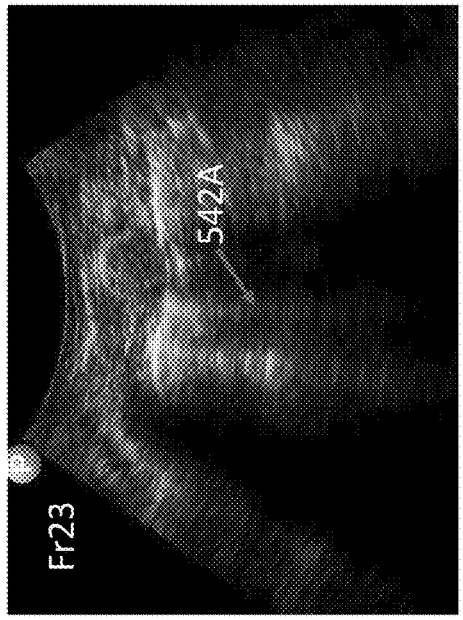
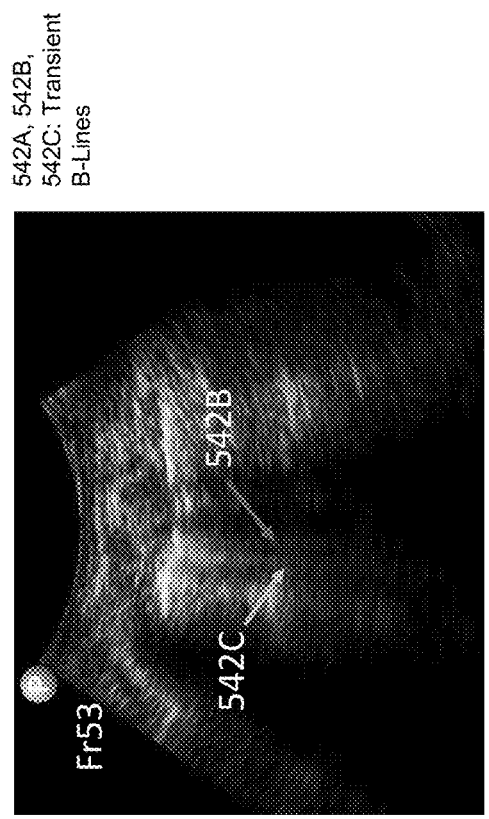
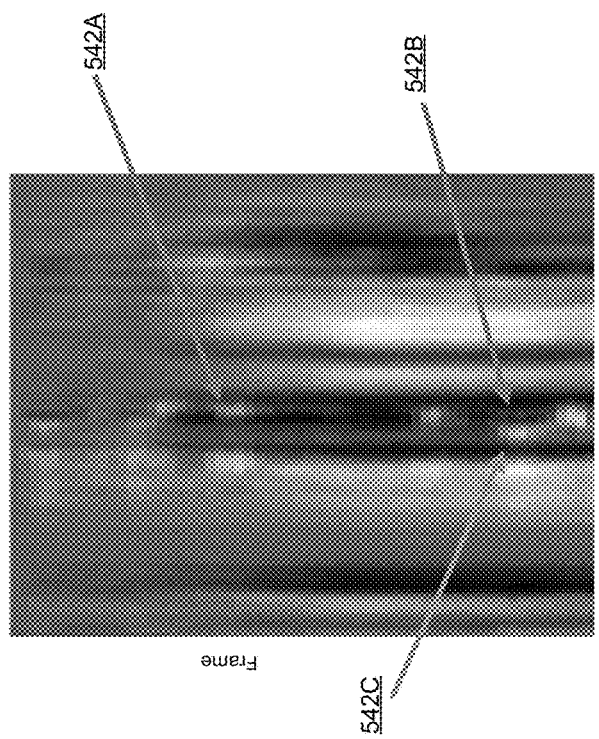
FIG. 5D

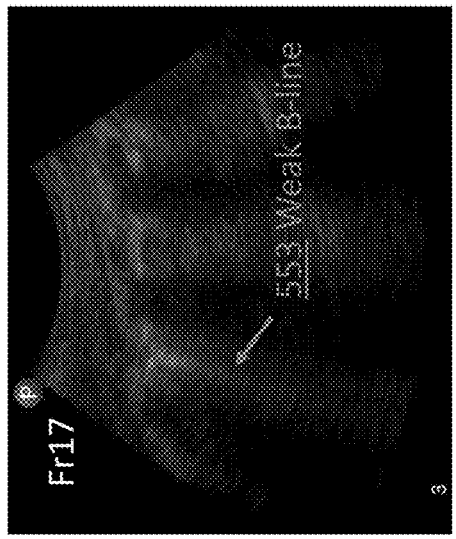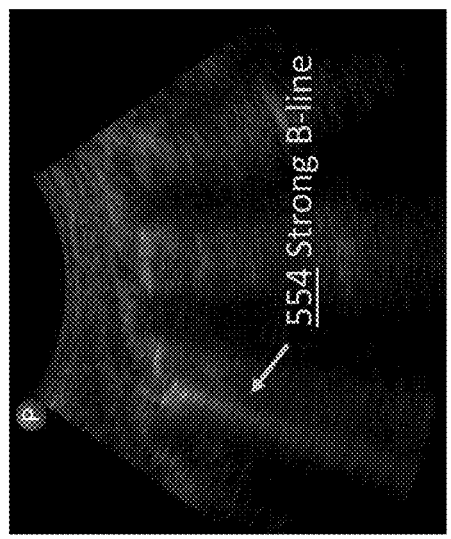
551 Ultrasound Image Frame 17 — 553 Weak B-line
552 Ultrasound Image Frame 48 — 554 Strong B-line
FIG. 5E
Q-mode can detect B-lines
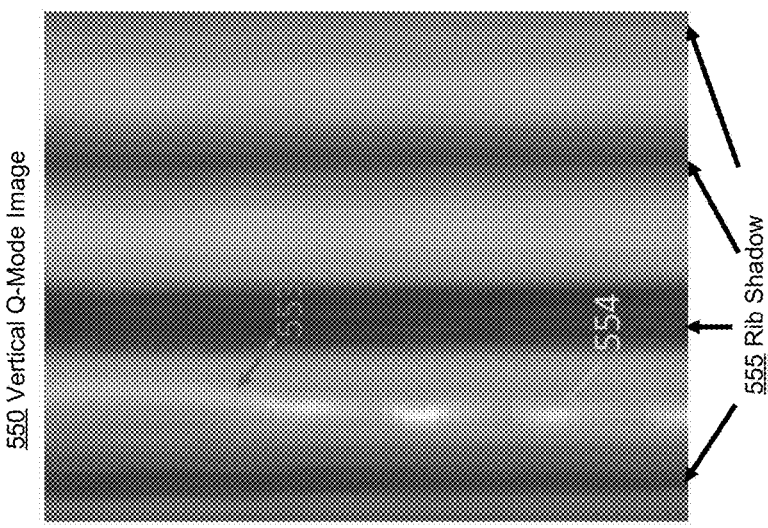
550 Vertical Q-Mode Image
555 Rib Shadow

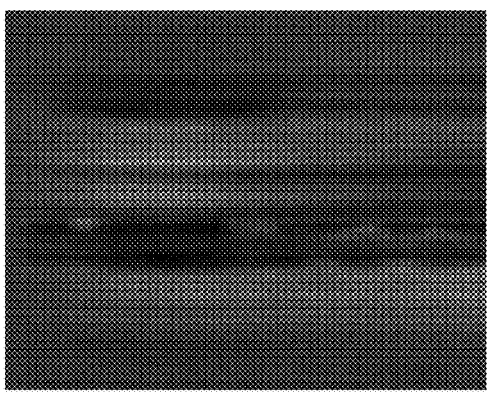
612 Baseline-Adjusted Vertical Q-Mode Image With Frame 1 Values Used As Baseline
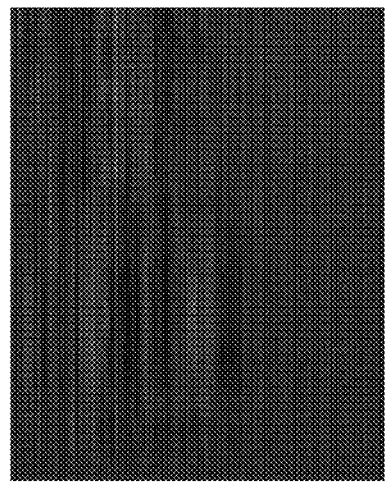
622 Baseline-Adjusted Horizontal Q-Mode Image With Frame 1 Values Used As Baseline
610 Vertical Q-Mode Image of 602
617
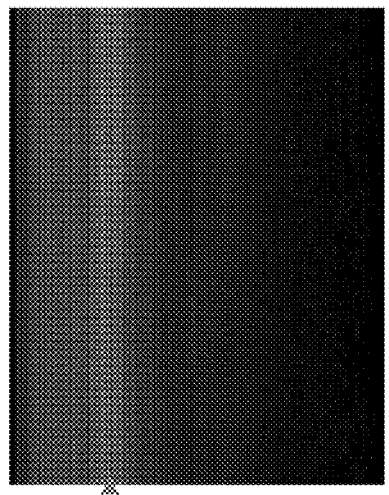
620 Horizontal Q-Mode Image of 602
619 Pleural Line
FIG. 6B Frame25 baseline-subtracted
Threshold value plays a role
Threshold=4
646 Vertical Q-Mode Image With Frame 25 Values Subtracted And Thresholded at Value 4
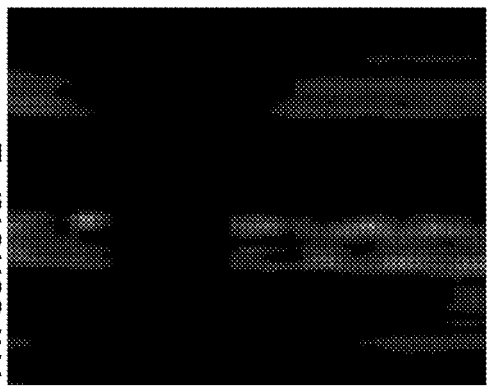
Threshold=2
644 Vertical Q-Mode Image With Frame 25 Values Subtracted And Thresholded at Value 2
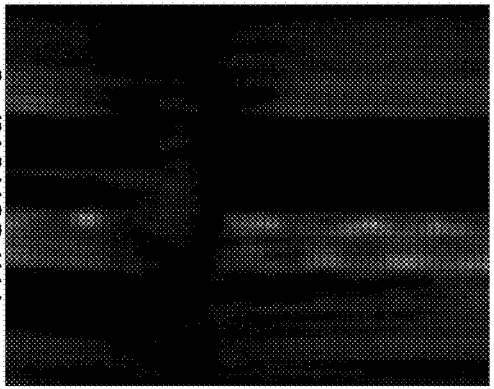
Threshold=0
642 Vertical Q-Mode Image With Frame 25 Values Subtracted And Thresholded at 0
FIG. 6C

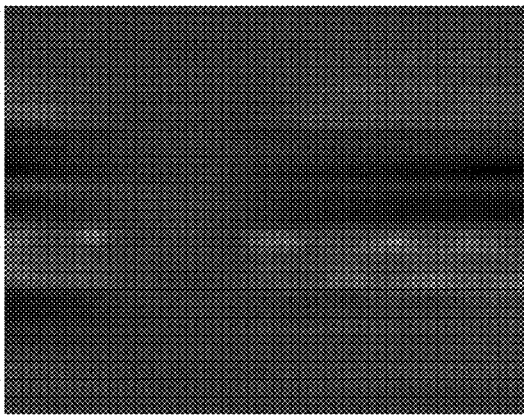
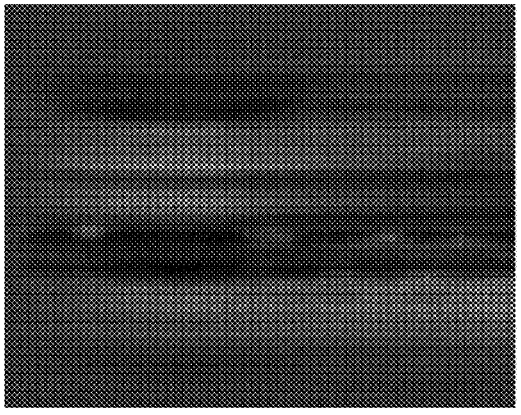
FIG. 6D

702 Ultrasound Image

704 B-Line

Frame 25 (left) vs. median value (right) as baseline
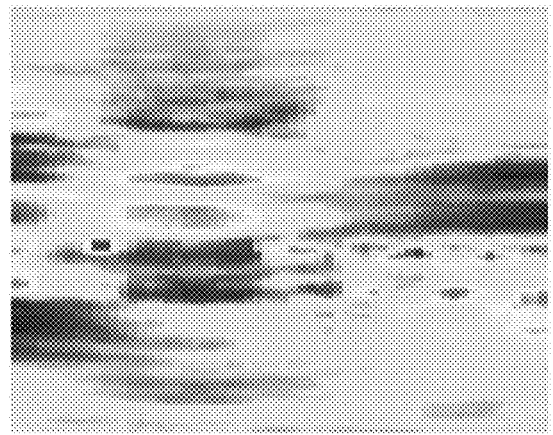
714 Baseline-Adjusted Vertical Q-Mode Image of 702 With Median Pixel Value Used As Baseline (Subtracted)
Median baseline-subtracted
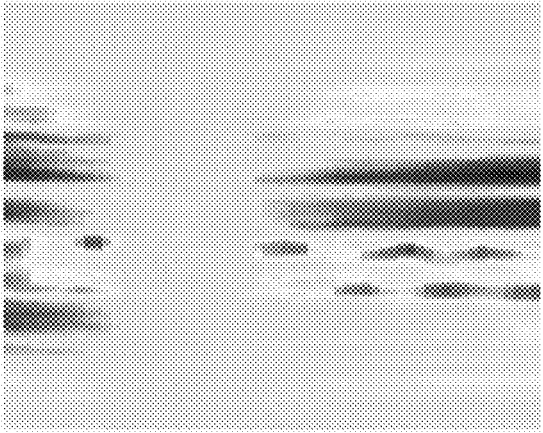
712 Baseline-Adjusted Vertical Q-Mode Image Of 702 With Frame 25 Used As Baseline (Subtracted)
Frame25 baseline-subtracted
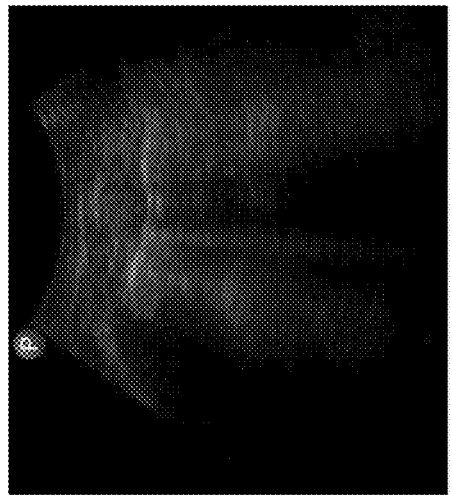
702 Ultrasound Image (From Fig. 7A)
FIG. 7B

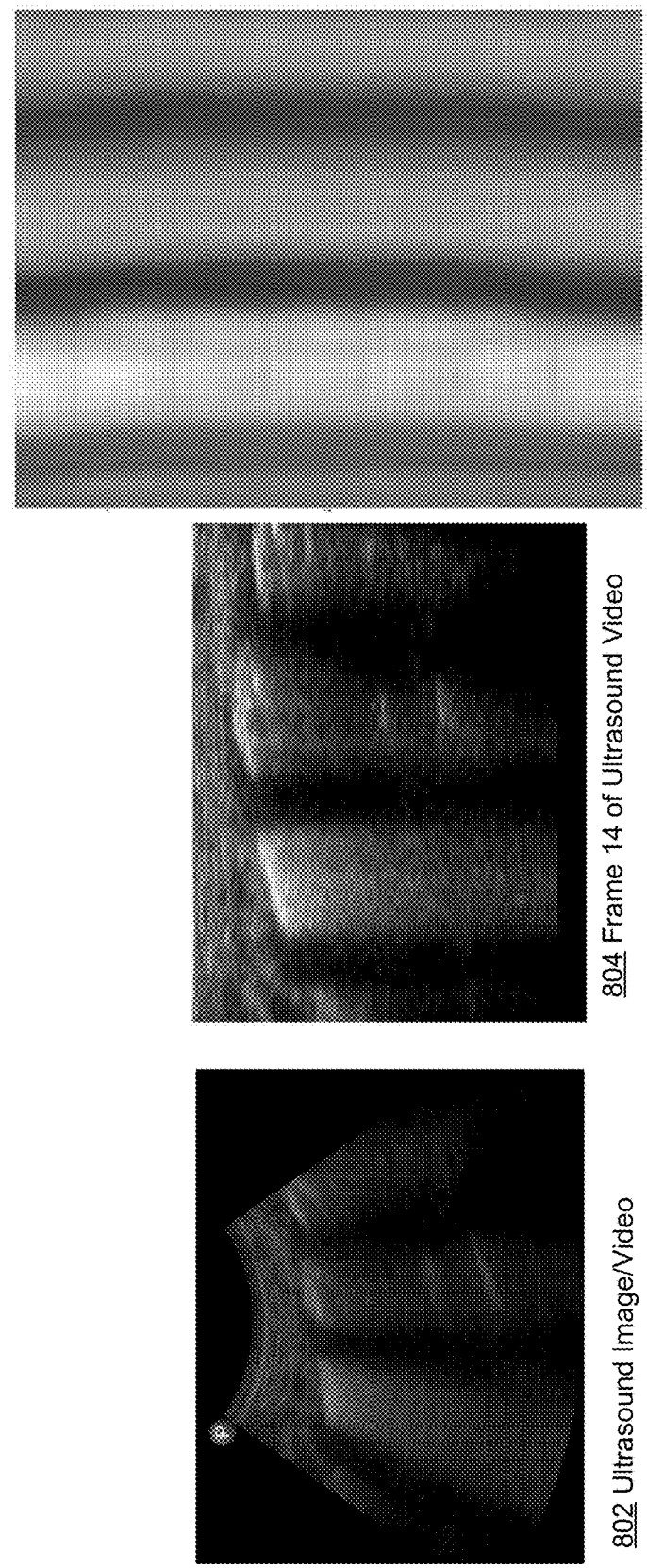

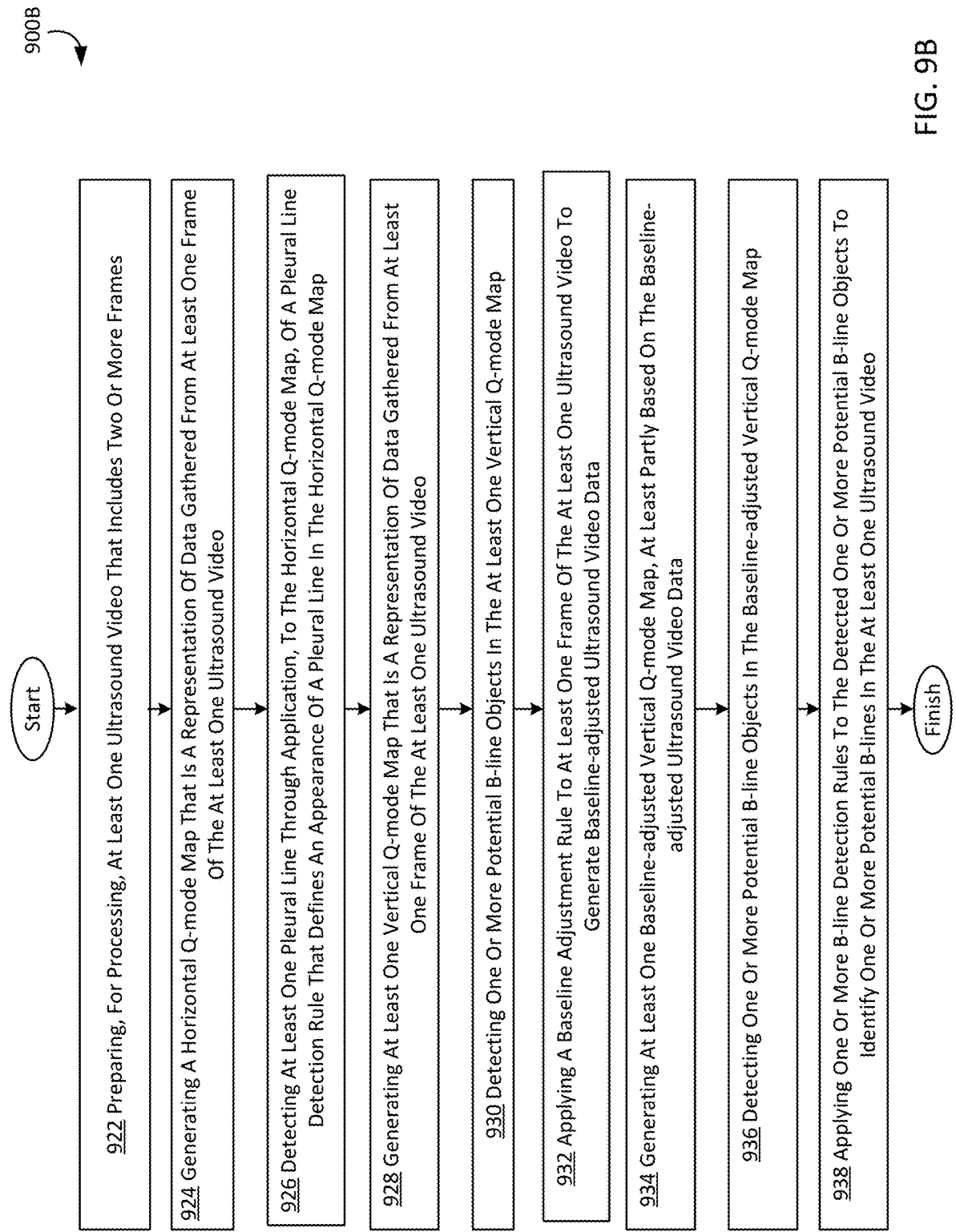

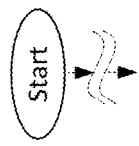

928 Generating At Least One Vertical Q-mode Map That Is A Representation Of Data Gathered From At Least One Frame Of The At Least One Ultrasound Video 1325 Creating, For Each Frame, A Vertical-Average Row Vector That Includes A Row Of Averaged Pixel Intensities, Wherein Each Averaged Pixel Intensity Represents A Vertical Average Of Pixel Intensities Along A Range Of Rows Of A Corresponding Column 1326 The Range Of Rows Is All Rows In The Respective Frame 1327 The Range Of Rows Is Fewer Than Seventy-five Percent Of The Rows In The Respective Frame 1328 The Range Of Rows Includes All Rows That Appear Below The Detected Pleural Line In The Respective Frame 1320 Generating At Least One Vertical Q-mode Image At Least Partly Based On The At Least One Ultrasound Video 1322 Using The Data Present In The Generated At Least One Vertical Q-mode Image To Mark Or Modify Areas Of The At Least One Ultrasound Video That Represent One Or More Rib Shadows 1330 Creating The Vertical Q-mode Map By Stacking The Created Vertical-Average Row Vectors Downward Vertically, According To Frame, From A Top-left Origin

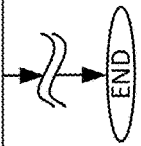

FIG. 13

Free ROC vs Distance Tolerance
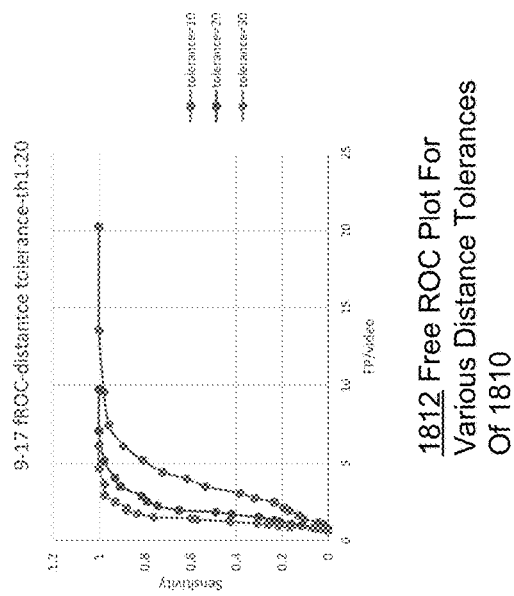
1812 Free ROC Plot For
Various Distance Tolerances
Of 1810
FIG. 18
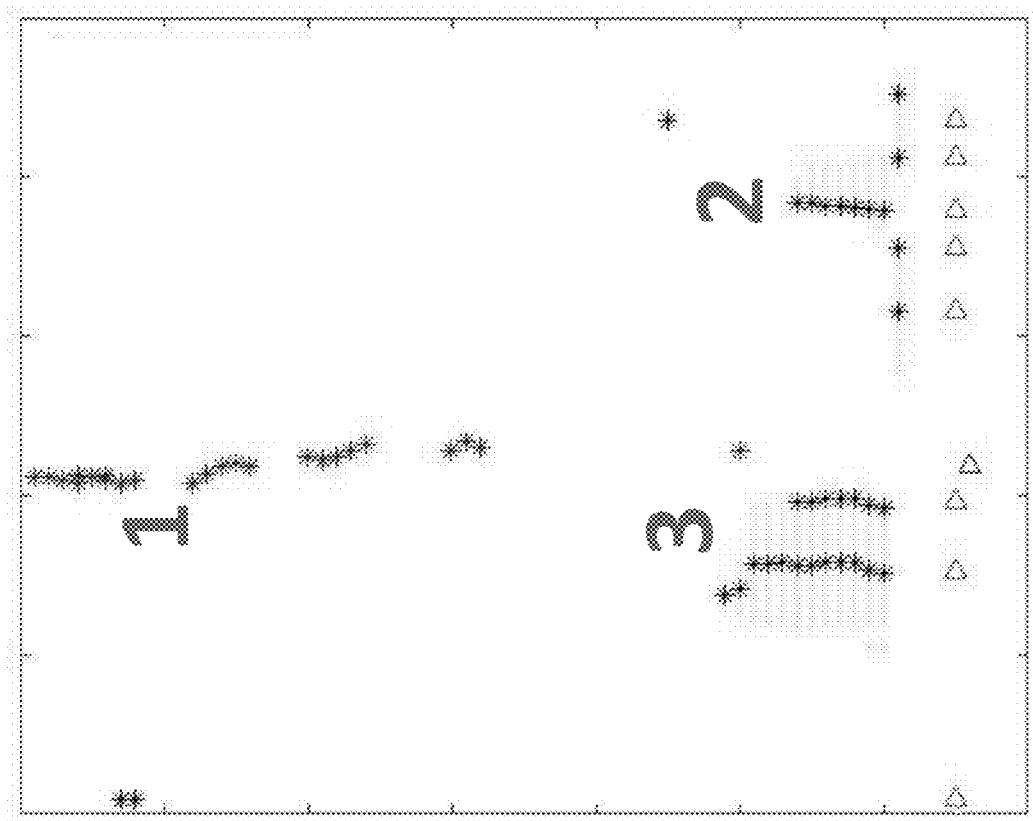
1810 Annotated Thresholded Vertical Q-mode Map Showing
Video-Based And Frame-Based Potential B-Line Detection

DEVICES, SYSTEMS, AND METHODS FOR DIAGNOSIS OF PULMONARY CONDITIONS THROUGH DETECTION OF B-LINES IN LUNG SONOGRAPHY

CROSS-REFERENCE TO RELATED APPLICATIONS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

PRIORITY APPLICATIONS

The present application claims benefit of priority of U.S. Provisional Patent Application No. 62/525,952, entitled Devices, Systems, and Methods for Diagnosis of Pulmonary Conditions Through Detection of B-Lines in Lung Sonography, naming Liming Hu, Courosh Mehanian, Benjamin K. Wilson, and Xinliang Zheng as inventors, filed 28 Jun. 2017, which was filed within the twelve months preceding the filing date of the present application or is an application of which a currently priority application is entitled to the benefit of the filing date.

This invention was made with Government support under Agreement No. HR0011-17-3-001, awarded by DARPA. The Government has certain rights in the invention.

RELATED APPLICATIONS

None as of the filing date.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

BACKGROUND

The invention is in the technical field of pulmonary ultrasound image or ultrasound echo map diagnosis through the automated and automatic machine-performed detection of B-lines and/or other lung phenomena in ultrasound images.

SUMMARY

Chest and/or lung sonography (hereinafter interchangeably referred to as "lung ultrasound" or as context dictates, simply "ultrasound") is the use of a transducer to emit high-frequency acoustic waves from the transducer into the human body, and to detect their return from contact with one or more interior portions of the human body. When applied to the lungs, ultrasound technology can be used to detect artifacts in the ultrasound image that are useful to diagnose various illnesses and conditions. These ultrasound images, however, conventionally require interpretation by a specialist.

This specialist interpretation, although generally accurate, may substantially increase the cost of extracting useful diagnosis from pulmonary ultrasound images, and also may substantially increase the time required to extract useful diagnosis. Moreover, although conventional ultrasound equipment is relatively inexpensive, plentiful, and generally portable (relative to other forms of imaging that rely on ionizing radiation, for example), access to specialists who can read and diagnose pulmonary conditions based on the pulmonary ultrasound images may be limited. This is especially true in developing countries, where pneumonia is a one of the leading causes of mortality, particularly in infants and children. In many remote areas of the world, access to ultrasound equipment is not a problem, but lack of access to specialists capable of reading the output of the ultrasound equipment may be more problematic.

Nevertheless, it is often difficult to diagnose lung conditions such as pulmonary edema, infection, or other signs of pneumonia, even for specialists. The "B-lines" which are used to diagnose fluids or nodules in the lung are not easy to detect, and many artifacts that appear to be "B-lines," but are not B-lines, appear in these images, as will be discussed in more detail herein. Thus, any computer-aided detection and image diagnosis must take these factors into account, and these factors may be different for each lung. Current computer technology and algorithms cannot successfully detect B-lines and thus, cannot provide accurate diagnoses or even serve as an accurate first pass to allow further specialist review.

Thus, the devices, methods, and systems herein constitute an improvement to a computer, to the way a computer works, e.g., by allowing a computer to perform a process currently only provided by human specialists, and only after years of training, in order to reduce the cost of obtaining useful results from an ultrasound device. Additionally, the devices, methods, and systems described herein disclose a novel transformation of image data that allows for detection of B-lines, as well as the application of a novel set of rules to that novel transformation of image data. These fundamentally new discoveries allow targeted computation to perform work that ordinarily could only be done by a highly-trained human specialist. It is important to note, however, that with generation of the Q-mode data, and application of the rules to that Q-mode data, the computer is not merely performing the same steps as a human specialist would perform, but rather reaches a similar result in a fundamentally different way. That is, the computer is not merely performing the same steps as a human specialist would perform, but rather reaches a similar result using novel data generation and rule set application. Specifically, as will be described in more detail herein, the automated detection of B-lines in ultrasound images is performed using novel data generation and application of a specific rule set to that generated data.

In one or more various aspects, one or more related systems may be implemented in machines, compositions of matter, or manufactures of systems, limited to patentable subject matter under 35 U.S.C. 101. The one or more related systems may include, but are not limited to, circuitry and/or programming for affecting the herein-referenced method aspects.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent by reference to the detailed description, the corresponding drawings, and/or in the teachings set forth herein.

BRIEF DESCRIPTION OF THE FIGURES

For a more complete understanding of embodiments, reference now is made to the following descriptions taken in connection with the accompanying drawings. The use of the same symbols in different drawings typically indicates similar or identical items, unless context dictates otherwise, with the exception of arrows, which may be used to indicate exemplary but non-limiting process flow when appearing in process/method flowcharts, and which may be used to indicate exemplary but non-limiting data flow when appearing in system and device diagrams, as context dictates. The illustrative embodiments described in the detailed description, drawings, and claims are not meant to be limiting. Other embodiments may be utilized, and other changes may be made, without departing from the spirit or scope of the subject matter presented here.

FIG. 2, including

FIG. 3, including

FIG. 5B shows an exemplary illustration of various vertical Q-mode maps/images taken at various depth ranges of an ultrasound image/video, according to various embodiments of the invention.

FIG. 5C shows an exemplary illustration of various baseline-adjusted vertical Q-mode maps/images and various baseline-adjusted horizontal Q-mode maps/images, according to various embodiments of the invention.

FIG. 5D shows an exemplary illustration of a mapping of transient B-lines between video frames and Q-mode maps/images, according to various embodiments of the invention.

FIG. 5E shows an exemplary illustration of a mapping of transient B-lines and rib shadows between video frames and Q-mode maps/images, according to various embodiments of the invention.

FIG. 6B shows an exemplary illustration of various Q-mode maps/images and modified Q-mode maps/images, based on ultrasound image 602, according to various embodiments of the invention.

FIG. 6C shows an exemplary illustration of various Q-mode maps/images and modified Q-mode maps/images, according to various embodiments of the invention FIG. 6D shows an exemplary illustration of various Q-mode maps/images and modified Q-mode maps/images, according to various embodiments of the invention.

FIG. 7B shows an exemplary illustration of various baseline-subtracted Q-mode maps/images, according to various embodiments of the invention.

FIG. 8A shows an exemplary illustration of various ultrasound video images that contain merged B-lines, Q-mode maps/images and modified Q-mode maps/images, according to various embodiments of the invention.

FIG. 9B is a high-level logic flowchart of a process, e.g., operational flow 900B, according to various embodiments of the invention.

FIG. 10, including

FIG. 13 is a high-level logic flowchart of a generating a vertical Q-mode map operation 928, according to embodiments of the invention.

FIG. 18 shows an exemplary illustration of an effect of pre-defined distance tolerance selection in video-based B-line detection on free ROC (Receiver Operating Characteristic) curves, according to various embodiments of the invention.

DETAILED DESCRIPTION

Figure 1:
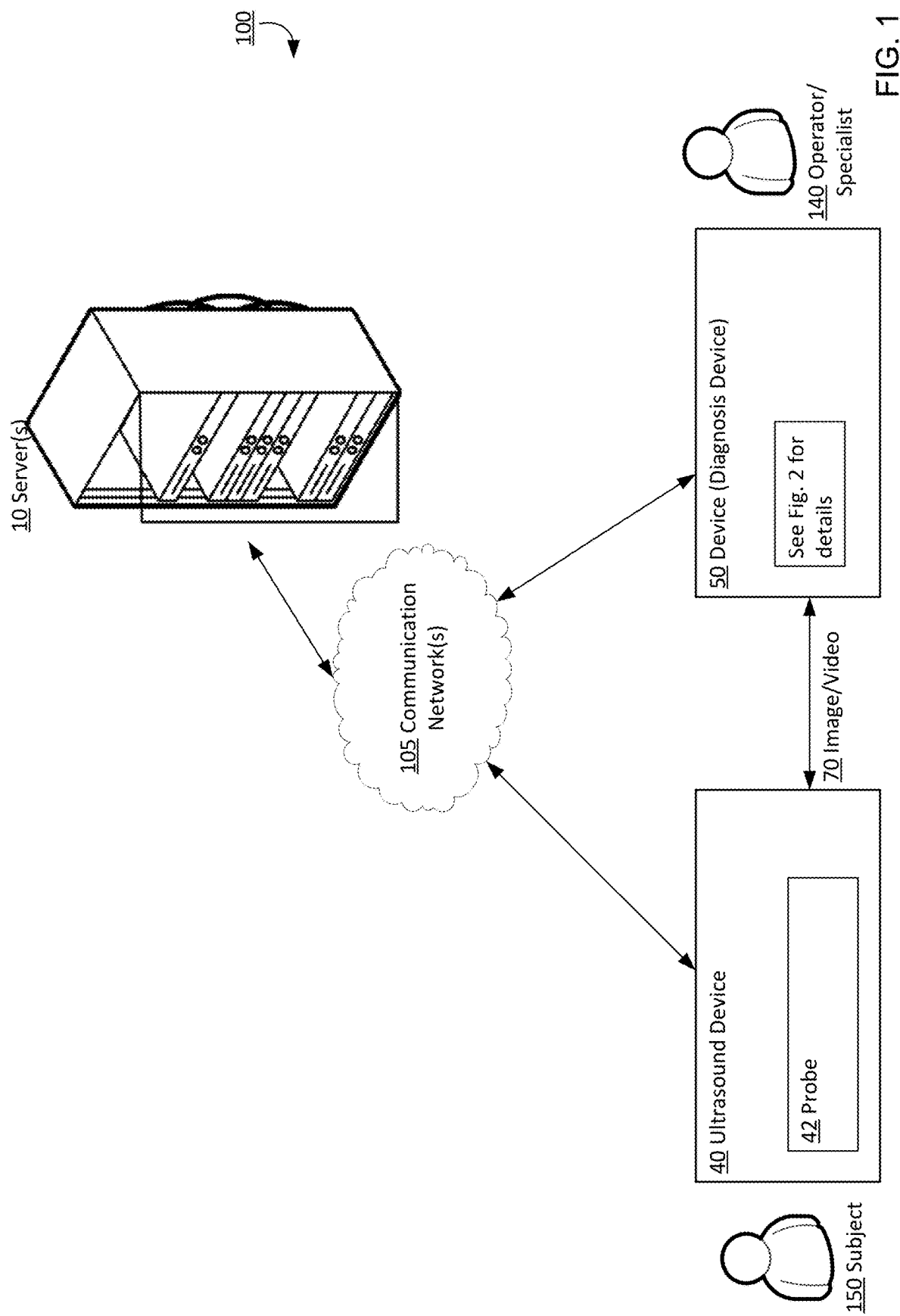
FIG. 1 shows an environment diagram of a device 50, operating in environment 100, according to various embodiments of the invention.

| Table of Contents |  |
|---|---|
| I. | Introduction: |
| II. | Advantages of Various Embodiments: |
| III. | The Claims are Directed to Statutory Subject Matter: |
| IV. | Description of Various Embodiments: |
| V. | Various Implementations and Non-Limiting Language: |
| VI. | Preface to the Claimed Subject Matter: |

Beginning of Detailed Description

I. Introduction

The following represents a discussion of the devices, methods, systems, articles of manufacture, and/or compositions of matter that make up the invention. The portions of the detailed description that are not claims should be understood as exemplary only, with the scope of the invention being defined completely and solely by the claims themselves, read in light of the foregoing and the following description.

II. Advantages of Various Embodiments

It is to be understood that the following are just some of the advantages of one or more various embodiments of the invention. The following advantages are not intended to describe every implementation of the invention nor are they intended to outline what is required for the invention. They do not limit the invention in any way. The invention is solely defined by the claims, and recitations or advantages presented herein that are not in the claims should not in any way be read into the claims. This section is provided merely so that later readers may understand and comprehend some of the advantages the instant invention provides over the existing art.

As will be discussed in more detail herein, B-lines are often difficult to distinguish from other artifacts in an ultrasound image. In various implementations, the position of an artifact relative to the pleural line is important in determining whether the detected artifact is a B-line or merely air or another foreign body. Thus, detection of the pleural line is useful in some, although not necessarily all, implementations.

Further, in various implementations, the overall cost of analysis of the ultrasound and diagnosis of the patient may be substantially decreased, as the amount of work required to be performed by a human specialist is decreased or eliminated. In various implementations, a human specialist is not needed to intervene in the process. In other implementations, the process may serve as a first pass through a set of ultrasound images, with further analysis to be performed by a human specialist. This is useful in, for example, such implementations as the deployment of pulmonary ultrasound technologies to developing countries, where many people, particularly children, may be scanned in a single day, and in which access to a human specialist may be severely restricted or not present at all.

III. The Invention, as Claimed, is Directed to Statutory Subject Matter

The claims, description, and drawings of this application may describe one or more of the instant technologies in operational/functional language, for example as a set of operations to be performed by a computer. Such operational/functional description in most instances would be understood by one skilled the art as specifically configured hardware (e.g., because a general purpose computer in effect becomes a special purpose computer once it is programmed to perform particular functions pursuant to instructions from program software).

Importantly, although the operational/functional descriptions described herein are understandable by the human mind, they are not abstract ideas of the operations/functions divorced from computational implementation of those operations/functions. Rather, the operations/functions represent a specification for massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to the human mind. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions will be understood by those of skill in the art to be representative of static or sequenced specifications of various hardware elements. This is true because tools available to one of skill in the art to implement technical disclosures set forth in operational/functional formats—tools in the form of a high-level programming language (e.g., C, java, visual basic, etc.), or tools in the form of Very high speed Hardware Description Language ("VHDL," which is a language that uses text to describe logic circuits)—are generators of static or sequenced specifications of various hardware configurations. This fact is sometimes obscured by the broad term "software," but, as shown by the following explanation, those skilled in the art understand that what is termed "software" is shorthand for a massively complex interchaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. In order to facilitate human comprehension, in many instances, high-level programming languages resemble or even share symbols with natural languages.

It has been argued that because high-level programming languages use strong abstraction (e.g., that they may resemble or share symbols with natural languages), they are therefore a "purely mental construct" (e.g., that "software"—a computer program or computer programming—is somehow an ineffable mental construct, because at a high level of abstraction, it can be conceived and understood in the human mind). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In fact, those skilled in the art understand that just the opposite is true. If a high-level programming language is the tool used to implement a technical disclosure in the form of functions/operations, those skilled in the art will recognize that, far from being abstract, imprecise, "fuzzy," or "mental" in any significant semantic sense, such a tool is instead a near incomprehensibly precise sequential specification of specific computational machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture, limited to patentable subject matter under 35 USC 101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

IV. Description of Various Embodiments

In the following detailed description, reference is made to the accompanying drawings, which form a part hereof. In the drawings, similar symbols typically identify similar or identical components or items, unless context dictates otherwise. The illustrative embodiments described in the detailed description, drawings, and claims are not meant to be limiting. Other embodiments may be utilized, and other changes may be made, without departing from the spirit or scope of the subject matter presented here.

Thus, in accordance with various embodiments, computationally implemented methods, systems, circuitry, articles of manufacture, ordered chains of matter, and computer program products are designed to, among other things, provide an interface for the environment 100 illustrated in FIG. 1.

Referring now to FIG. 1, FIG. 1 shows a system diagram according to one or more implementations. Specifically, FIG. 1 shows a system environment 100, which, in various implementations, includes a subject 150, an ultrasound device 40, a device 50, and a server 10. In some implementations, FIG. 1 also shows a specialist or operator 140, which represents the person operating the ultrasound device and/or the person reading and/or interpreting the result (in some, but not all, instances these are the same person). In various implementations, server 10 may communicate with device 50 over communications network 105. It is noted that, in various implementations, all of the various circuitry described herein may be part of ultrasound device 40, and/or all of the method steps described herein may be performed by ultrasound device 40. In other implementations, all of the various circuitry described herein may be part of device 50 and/or all of the method steps described herein may be performed by device 50. The server 10 may be wholly optional and may, in various implementations, be eliminated. In various implementations, ultrasound device 40 and/or device 50 may carry out all of the functions listed herein without being connected to a network, e.g., to communications network 105. In other various implementations, portions of the operations described herein, and portions of the circuitry described herein, may be partially executed at or on ultrasound device 40 and/or device 50, and partially executed at or on server 10, or. e.g., in the "cloud" or at another remote and/or distributed location. What follows from here, before further description of the devices and entities illustrated in FIG. 1 and beyond, is a basic description of the operation of an ultrasound device, e.g., ultrasound device 40, the various artifacts that can be seen in an ultrasound video, e.g., ultrasound image/video 70, and brief descriptions of the correlations between the artifacts that can be seen in the ultrasound video, and various conditions of the lung to which the ultrasound device has imaged.

Ultrasound Operation

Thus, in an implementation, an ultrasound device, e.g., ultrasound device 40 captures an ultrasound video of a pulmonary region, e.g., a region including the lungs. This video consists of a number of still images, e.g., frames, stitched together. The ultrasound device, e.g., ultrasound device 40, operates by sending an electric voltage to a probe, e.g., probe 42, which generates an acoustic wave (e.g., a soundwave, although not audible to human ears), e.g., through a piezoelectric device. In various implementations, a range of acoustic frequencies may be used to visualize the lungs, e.g., from 3 to 12 MHz, depending on various factors regarding what is to be detected, e.g., higher frequencies generally create higher resolution images but do not penetrate as far. The sound wave travels into the human body, e.g., the lung, and passes through the various tissue and organs until it hits an interface, e.g., an area where two different tissues are contiguous, or a tissue is contiguous with another material, e.g., air, water, or a nodule. At this interface, a portion of the sound is returned, e.g., reflected or scattered back, e.g., echoed, and is received by the probe and converted back to an electrical signal. Additional characteristics of this electrical signal, including the timing of the returned, reflected, or scattered sound and the intensity at which it is returned back, generate an ultrasound image or video by a standard process that is not repeated here.

In conventional systems, the ultrasound video is then read by a specialist, e.g., a radiologist. Although many regions of the world may have access to ultrasound technology, which is relatively plentiful, fewer regions of the world have adequate specialists to read the ultrasound video and perform diagnosis of patients based on the ultrasound video. This is particularly problematic in developing nations and hard-to-reach areas. Thus, in some implementations, the ultrasound video captured by the ultrasound device 40 is analyzed and diagnosed by machine according to various processes described herein.

In an implementation, the ultrasound device, e.g., ultrasound device 40 captures the ultrasound video, e.g., image/video 70 of FIG. 1, of the pulmonary region, as described above. In an implementation, the ultrasound video consists of a number of still images, e.g., frames, that are stitched together (the term "image" and "frame" will be used substantially interchangeably throughout, except where context dictates otherwise). These frames may be displayed on a monitor, e.g., a part of the device output component 220B, and/or saved for later analysis. In an implementation, real-time analysis of the ultrasound video that is captured may be performed, and in another implementation, the video is saved for later analysis consistent with systems and methods described herein. In an implementation, the image is handled according to one or more DICOM ("Digital Imaging and Communications in Medicine") standards (e.g., ISO standard 2052:2006), the entirety of which are available publicly at the National Electrical Manufacturers Association (NEMA) repository, with all rights reserved.

In an implementation, the ultrasound image will show areas that appear very dark with low pixel intensity. Generally, these dark areas are artefactual anechoic shadow images and are caused by the ribs in front of the lungs, generating what is referred to at various points in this document as a "rib shadow." In some implementations, these areas will be ignored, and in other implementations, these areas will be taken into consideration by one or more algorithms in an attempt to improve accuracy in detecting potential B-lines. In an implementation, in the ultrasound image, a healthy lung will show a hyperechogenic line that, on a Cartesian coordinate plane, will appear horizontal or substantially horizontal. This line generally represents the interface between the chest wall and the lung (which contains air and has a different density than the chest wall), and is commonly referred to as the "pleural line." As will be seen later, in various implementations, detection of the pleural line may be useful for processing the ultrasound video and/or detecting one or more potential B-lines, because objects detected "above" the pleural line (in the Cartesian coordinate plane) are generally caused by tissue that is located between the transducer and the lung, e.g., skin, fat, muscle tissue, or other tissue. These objects that are detected above the pleural line are not B-lines, and do not require consideration when performing B-line detection on the ultrasound video. Moreover, one characteristic of B-lines is that they originate from the pleural line. The pleural line's position is not strictly static, but may shift or change positions slightly with respiration or heartbeat.

In an implementation, other patterns may be viewed in the ultrasound image/video. For example, the circuitry described herein may detect "A-lines," which are horizontal, regularly spaced hyperechogenic lines. A-lines are commonly seen in both healthy and unhealthy patients, may be so-called reverberation artifacts, and may appear as artifacts of the pleural line. A-lines are not used in the techniques discussed further herein, and because they are generally substantially horizontal, are generally not difficult to distinguish from B-lines, which are generally substantially vertical in the Cartesian coordinate plane. Referring now to these B-lines, the circuitry described herein may be architected to detect "B-lines," which are vertical or substantially vertical lines, generally narrow, and which start from the pleural line and extend outward. In various implementations, these B-lines are the lines that are to be detected for use in diagnosis, although a certain number, e.g., fewer than three, of B-lines may be present in healthy lung tissue. B-lines are sometimes called "lung comet tails" because of their appearance in a conventional ultrasound image. When viewed in the ultrasound image, B-lines may cancel out or "remove" A-lines that would otherwise overlap from the images.

In an implementation, other patterns may be viewed in the image. Not all of these patterns and/or artifacts will be discussed in this document, but the circuitry described herein may detect two other types of artifacts that are specifically mentioned here due to their similar appearance to B-lines, and which, in various implementations, may be accounted for in order to reduce a false positive rate of B-line detection. For example, the circuitry may detect "Z-lines," which are similar to B-lines and may be referred to as "false B-lines." Like true B-lines, Z-lines may be vertical lines, and may be present in both healthy and unhealthy lungs. In some implementations, Z-lines differ from B-lines in that they are ill-defined, have a shorter length than B-lines, and do not "erase" or otherwise cancel out A-lines. For another example, the circuitry may detect E-lines, which can be indicators of parietal emphysema or parietal echogenic multiple foreign bodies, and may be detected in some implementations. E-lines are often well defined, but unlike B-lines, E-lines do not arise from the pleural line. Instead, E-lines originate in subcutaneous space in the lung, e.g., where gas is trapped or where there is presence of a foreign body or nodule. Although E-lines may be useful in diagnosing lung health, for the implementations disclosed herein, the focus is on B-line detection and diagnosis therefrom.

Diagnosis Based on B-Lines

As set forth above, ultrasound technology is an inexpensive and widely available scanning technology for diagnosing patients. Detection of B-lines in a human lung may indicate a number of different conditions. Most commonly, infection or edema may cause water or other fluid buildup in the lungs that may manifest itself as B-lines, and may be a precursor or an indicator of serious respiratory illnesses, e.g., pneumonia. Sometimes, the presence of B-lines may indicate a foreign object in the lungs (e.g., if the resolution of the ultrasound device is set to, e.g., sub-millimeter resolution). Accordingly, detection of B-lines serves as a useful screen for healthy vs. unhealthy lung tissue. As mentioned above, B-lines may be present in healthy lungs but at a lower rate, e.g., fewer than three B-lines in a healthy lung.

It is noted that the foregoing description is neither exhaustive nor fully complete, and thus should not be interpreted as limiting the various implementations disclosed herein. Other implementations detect other artifacts and correlate to other diagnoses. The foregoing is merely provided as one example that is easily and thoroughly illustrated throughout the rest of the drawings and specification, with the full scope of the invention to be set forth exclusively in the claims. Thus, having now completed a brief description of the operation of the ultrasound, the various artifacts that are to be detected, and the correlated diagnoses that follow therefrom, reference is returned to FIG. 1. In an implementation, ultrasound device 40 may include a probe 42. The probe 42 may be, e.g., a transducer probe that emits the sound waves and receives the reflected soundwaves. In an implementation, probe 42 may be the entirety of ultrasound device 40, for example, all of the processing may be performed by device 50. In an implementation, probe 42 may be connected to ultrasound device 40, e.g., by a wire, or through wireless connection. In another implementation, probe 42 contains the transducer probe, ultrasound device 40 handles a portion of the processing, and device 50 carries out the processing that is described further herein in the description and the claims. In various portions of this document, this latter implementation will be used for exemplary purposes; however nothing in this document should be construed as limiting where processing can take place, where circuitry is located, or which circuitry may be implemented in ultrasound device 40, device 50, server 10, some combination thereof, or other remote circuitry not pictured in FIG. 1.

In various implementations, device 50 may be a server-type device, or may be a user-level device, e.g., including, but not limited to, a desktop computer, a laptop computer, a special-purpose medical device, a scanner, a piece of diagnostic equipment, a cellular phone, a network phone, a smartphone, a tablet, a music player, a walkie-talkie, a radio, an augmented reality device (e.g., augmented reality glasses and/or headphones), wearable electronics, e.g., watches, belts, earphones, or "smart" clothing, earphones, headphones, audio/visual equipment, media player, television, projection screen, flat screen, monitor, clock, appliance, navigation system, medical alert device, remote control, peripheral, video camera, personal video recorder, personal audio recorder, and/or any combination thereof.

In various implementations, communications network 105 may be any form of one or more networks, wired or wireless or some combination thereof, that serve to transmit data and/or information between two endpoints. In various embodiments, the communications network 105 may include one or more of a local area network (LAN), a wide area network (WAN), a metropolitan area network (MAN), a wireless local area network (WLAN), a personal area network (PAN), a Worldwide Interoperability for Microwave Access (WiMAX), public switched telephone network (PTSN), a general packet radio service (GPRS) network, a cellular network (GSM, CDMA, etc.), a microwave network, and so forth. The communications network 105 may be wired, wireless, or a combination of wired and wireless networks. It is noted that "communications network" as it is used in this application refers to one or more communication networks, which may or may not interact with each other.

In various implementations, server 10 may be any piece or set of computer equipment capable of being implemented in the request-response model. For example, a server 10 may provide various services, functionalities, or computational tasks for one or more clients, including, but not limited to, device 50. The term "server" does not imply a specific set or class of hardware, although hardware designed for servers may be preferable in some applications. Additionally, the term "server" does not imply more than one client, or even one client, provided that the server is capable of handling a client. Moreover, server 10 may be part of a set of distributed servers and/or other computing equipment, with variable locations for different parts (e.g., a memory may be in one physical location, and a CPU may be in an entirely different location), and may have various redundancy portions which also may be in various, disparate locations. In other implementations, server 10 may be local to device 50 or internal to device 50 (e.g., in some implementations, portions of device 50 may act as server 10 to one or more processes active on device 50). Additionally, server may refer to the specific computer program or process that gives rise to the server, the device that acts as the server by running the program, or some combination thereof. The use of the term "server" does not exclude or eliminate a peer-to-peer or other network arrangement. The ultrasound device 40, device 50, server 10, and communications network 105 are illustrated as shown in FIG. 1 for ease of understanding, but other arrangements and setups are contemplated and are within the scope of the following disclosure.

Figure 2A:
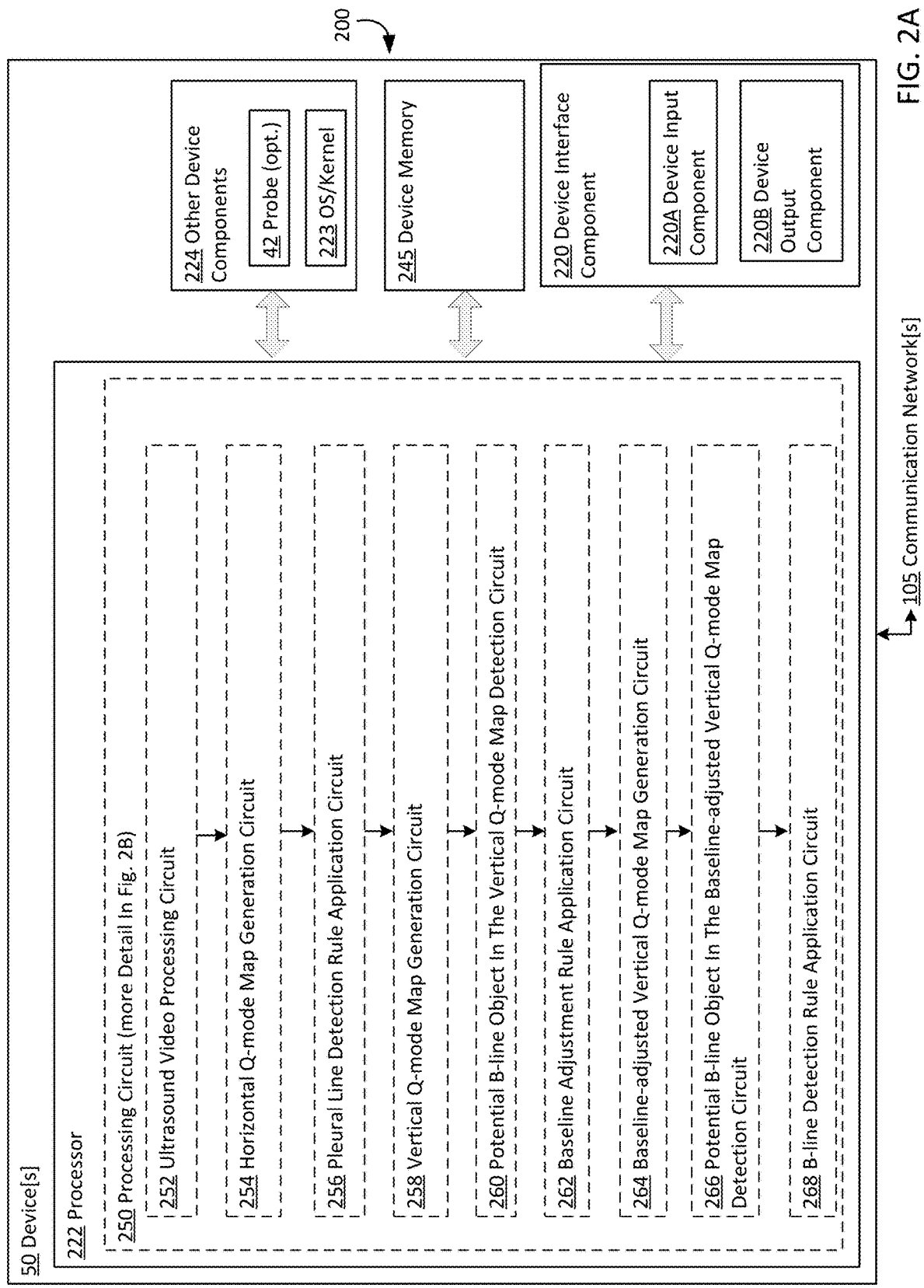
FIGS. 2A-2E, shows exemplary implementations of device 50, operating in environment 200 and/or environment 200B, according to various embodiments of the invention.

Before moving on to FIG. 2A, which shows implementations of device 50 according to various embodiments, further explanation of the Q-mode maps may be beneficial for understanding. Specifically, this document references Q-mode maps throughout, including generation of Q-mode maps, use of Q-mode maps in B-line object and other object detection, and various other operations to be performed on or with Q-mode maps. As will be discussed herein, in an implementation, there are two different types of Q-mode maps, horizontal Q-mode maps, and vertical Q-mode maps. Of the vertical Q-mode maps, in an implementation, there are two sub-types: the standard vertical Q-mode map, and the baseline-adjusted Q-mode map. These also will be described in more detail herein, however as an overview, the horizontal Q-mode map is generally configured to assist in detecting pleural lines. The vertical Q-mode map is generally configured to assist in detecting merged or persistent B-lines in the ultrasound video. The baseline-adjusted Q-mode map is generally configured to assist in detecting transient B-lines, e.g., B-lines that do not appear throughout the entirety of the ultrasound video. The Q-mode maps have other purposes and other possible uses, but these are the basic uses in an exemplary implementation. Prior to referencing the specific circuitry of B-line detection according to various implementations, it is beneficial to describe, as background, how to generate the various Q-mode maps, with reference to FIG. 3, e.g., FIGS. 3A-3E. The implementation of generating the Q-mode maps, in both circuitry and process, will be described in more detail, after an initial explanation of the Q-mode maps is provided, with reference to FIG. 3.

Q-Mode Maps

Figure 3A:
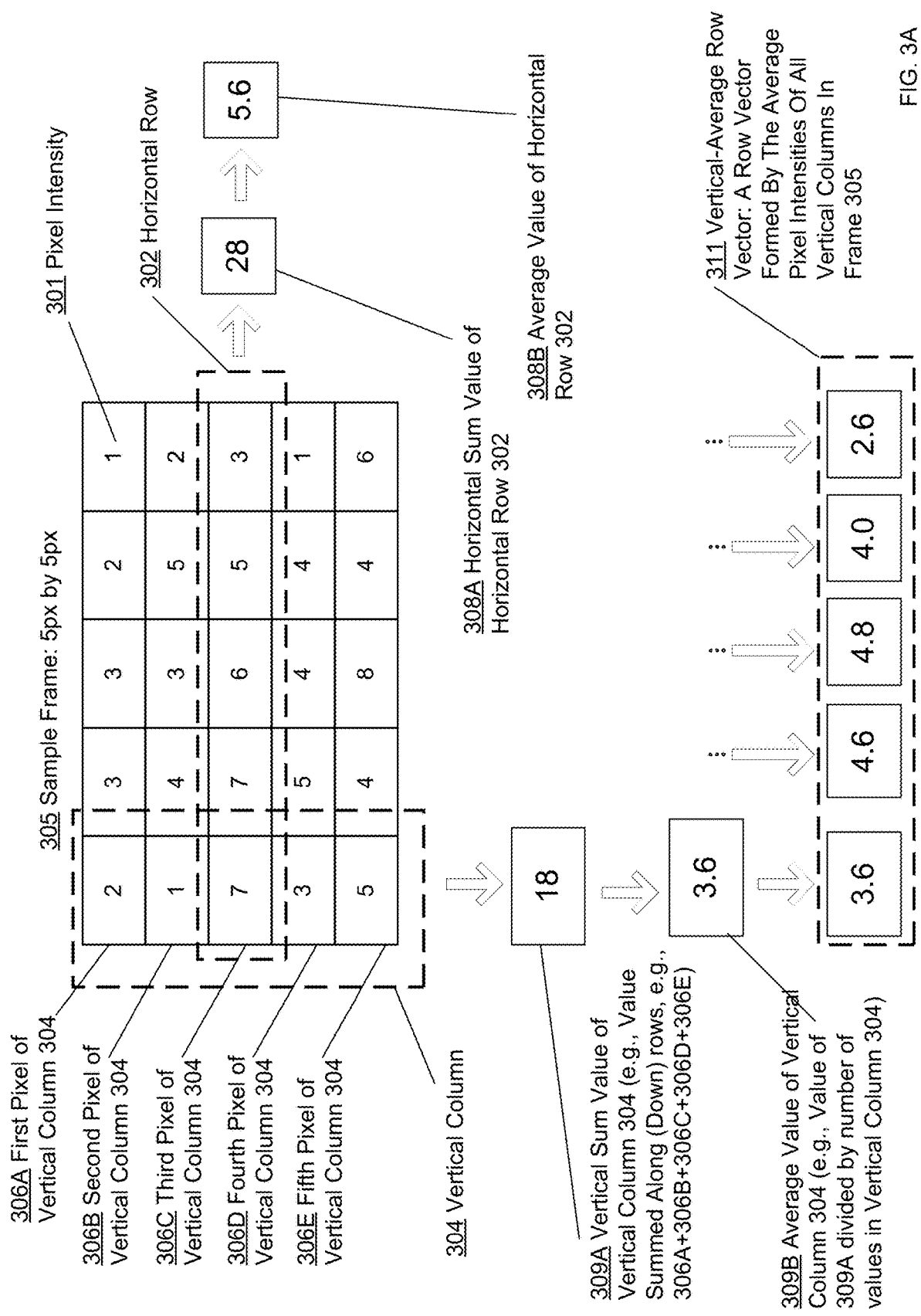
FIGS. 3A-3E, shows a graphical example of implementations of various Q-mode maps or images, according to various embodiments of the invention.

In various implementations, the ultrasound video is transformed into what will hereinafter be referred to as "Q-mode," e.g., "Q-mode maps," "Q-mode image(s)," or simply, "Q-mode," with various modifiers that will be described in more detail herein, e.g., "horizontal Q-mode" or "baseline-adjusted Q-mode." In many of the illustrations that follow, the Q-mode appears as an image, because it is a map of pixel intensities at specific coordinates, however, this is merely done for illustration, as the processing of the Q-mode map does not require conversion, display, or storage, as an image, in order to properly function. Accordingly, unless dictated otherwise by context, the term "Q-mode map" and "Q-mode image" should be considered interchangeable and will be used substantially interchangeably. FIG. 3, and the included FIGS. 3A-3E, show various implementations of how a Q-mode map may be generated from one or more frames of a video, e.g., an ultrasound video. Referring now to FIG. 3A, FIG. 3A shows a sample frame 305. In an implementation, sample frame 305 represents a single frame of a video, e.g., an ultrasound video, e.g., ultrasound image/video 70 (from FIG. 1). Due to the limitations of black and white rendering, and also to illustrate the interchangeability between a "Q-mode image" and a "Q-mode map," rather than showing an actual pixel in each cell of sample frame 305, FIG. 3A (and the other sub-figures of FIG. 3) shows a number that corresponds to the pixel intensity of the pixel in that cell. In various implementations, a pixel intensity may be split into various components, or may be a single value, e.g., from 0 to 255, as in an 8-bit grayscale image. For ease of illustration of this example, the pixel intensities shown in FIG. 3 will be integers from 0-9, reflecting relative levels of pixel intensity (e.g., a pixel intensity of "4" will be twice as intense as a pixel intensity of "2"), although in actual implementations, greyscale intensity values are often on a non-linear scale, e.g., a logarithmic or gamma scale. It is noted here that, although in some disclosed implementations, pixel intensity values are used to generate the Q-mode images, in other implementations, other features of the image could be used, particularly if the image is a color image. In various implementations, ultrasound imaging devices may be used that generate greyscale images (e.g., images in which only intensity information is stored), however, in other implementations, color or false-color images may be generated and other image data, e.g., RGB vectors, alpha values, or other numerical representations of visual data may be used.

Referring again to FIG. 3A, in an implementation, sample frame 305 is a twenty-five pixel square-shaped image that is five pixels by five pixels. As shown in FIG. 3A, a column of pixels, e.g., vertical column 304, represents all of the pixels in the frame with the same "x-value" on a traditional screen coordinate system (e.g., with "0,0" at the top-left, the x-coordinate increasing rightward, and the y-coordinate increasing downward), or all of the pixels in a same column, as represented in a traditional table or matrix system. Similarly, a row of pixels, e.g., horizontal row 302, represents all of the pixels in the frame with the same "y-value" on a traditional screen coordinate system. As will be discussed in more detail herein, the selection of a coordinate system is not specifically important to the process, nor is the designation of x and y axes of the various Q-mode maps. The herein displayed coordinate system, origin selection, and x- and y-axis designations are provided for ease of understanding/explanation only, and in other implementations these selections may be flipped, altered, transposed, or otherwise modified. The designators "vertical" and "horizontal" may appear redundant, but are provided for ease of understanding the process.

Referring again to FIG. 3A, FIG. 3A also shows a summation 309A, which is a summation value (total) of the pixel intensities of vertical column 304 of sample frame 305, e.g., first pixel 306A, second pixel 306B, third pixel 306C, fourth pixel 306D, and fifth pixel 306E. The five pixel intensity values of first pixel 306A (2), second pixel 306B (1), third pixel 306C (7), fourth pixel 306D (3), and fifth pixel 306E (5), are added together (e.g., 2+1+7+3+5) to arrive at a summation 309A with a value of 18, as shown in FIG. 3A. In an implementation, the value of summation 309A is then converted to an average (e.g., by dividing by the number of pixel intensities that were taken) for the vertical column 304, that is, the sum (18) is divided by the number of rows that were sampled from vertical column 304 (5). This value leads to vertical average value 309B of vertical column 304. In the implementation shown herein, vertical average value 309B may be averaged using an arithmetic mean, although other implementations could use other averaging methods. To reiterate the example in FIG. 3A, vertical average value 309B is derived by dividing the summation 309A (18) by the total number of values (5) that constitute vertical column 304 (e.g., the total number of rows in sample frame 305), e.g., 18/5=3.6, to arrive at 3.6 as the value for vertical average value 309B. In an implementation, e.g., an implementation in which the Q-mode map may be displayed as an image on a display that uses integer values for the various pixel intensities, vertical average value 309B may be converted to an integer, e.g., through a rounding function, or a floor or ceiling function, which may be handled by the hardware or software.

Referring again to FIG. 3A, FIG. 3A shows the same process being carried out for horizontal row 302, in which the row values of the third row (e.g., horizontal row 302) of sample frame 305 are summed together to arrive at summation 308A (e.g., 7+7+6+5+3=28). Also, similarly to as described above with respect to summation 309A, in various implementations, summation 308A may be converted into horizontal average value 308B. It is noted here that, although further calculations with described Q-mode implementations involve averaging, other calculations could be performed on the various vertical columns and horizontal rows, and are within the scope of implementations described by this document. For example, in another implementation, a median, mode, geometric mean, root mean square of vertical column 304, or other, more complex mathematical operation, including various stepwise operations or regression-fit operations.

Referring again to FIG. 3A, if the process by which vertical average value 309B is derived from vertical column 304 for each of the columns of sample frame 305, then five values will be generated. If those five values are placed horizontally in a one dimensional vector, with their position corresponding to the column number from which they were averaged, then a vertical-average row vector is generated, e.g., vertical-average row vector 311. This vertical-average row vector 311 includes each average of each column of sample frame 305, and a set of these vertical-average row vectors for each frame will be used to construct the vertical Q-mode map, as will be described herein with respect to FIGS. 3B and 3C.

An important note about terminology is included here regarding the vertical-average row vectors and their counterparts (not pictured in FIG. 3A; refer to FIG. 3D for illustration), the horizontal-average column vectors. Specifically, the vertical-average row vectors are so named because they are row (i.e., horizontal) vectors that are generated from averaging vertically down the columns of the frame. They are named row vectors, although they represent the average of columns (i.e., an averaging of a column down some or all rows), because the resultant structure is horizontal and is a one-dimensional row vector, the structure of which will be important later, when these one-dimensional row vectors are used to build the vertical Q-mode maps. Thus, the first two words of "vertical-average row vectors" represent the mathematical operation (e.g., vertical average, e.g., a sum of a column, down a set of rows divided by the number of rows summed), and the second two words represent the resultant data structure (e.g., a row vector).

Similarly, although not explicitly shown in FIG. 3A, the process by which horizontal average value 308B is generated from horizontal row 302 also may be repeated for the rows of sample frame 305, to generate five values representing the five present rows. The structure that results from these operations is named a horizontal-average column vector, as shown in FIG. 3D. Specifically, the horizontal-average column vectors are so named because they are column (i.e., vertical) vectors that are generated from averaging horizontally across the rows of the frame. These vectors are named column vectors, although they represent the average of rows (i.e., an averaging of a row across all columns), because the resultant structure is vertical and is a one-dimensional column vector. Thus, similarly to as above, except with directions switched, the first two words of "horizontal-average column vectors" represent the mathematical operation (e.g., horizontal average, e.g., a sum of a row, across a set of columns divided by the number of columns summed), and the second two words represent the resultant data structure (e.g., a row vector).

Figure 3B:
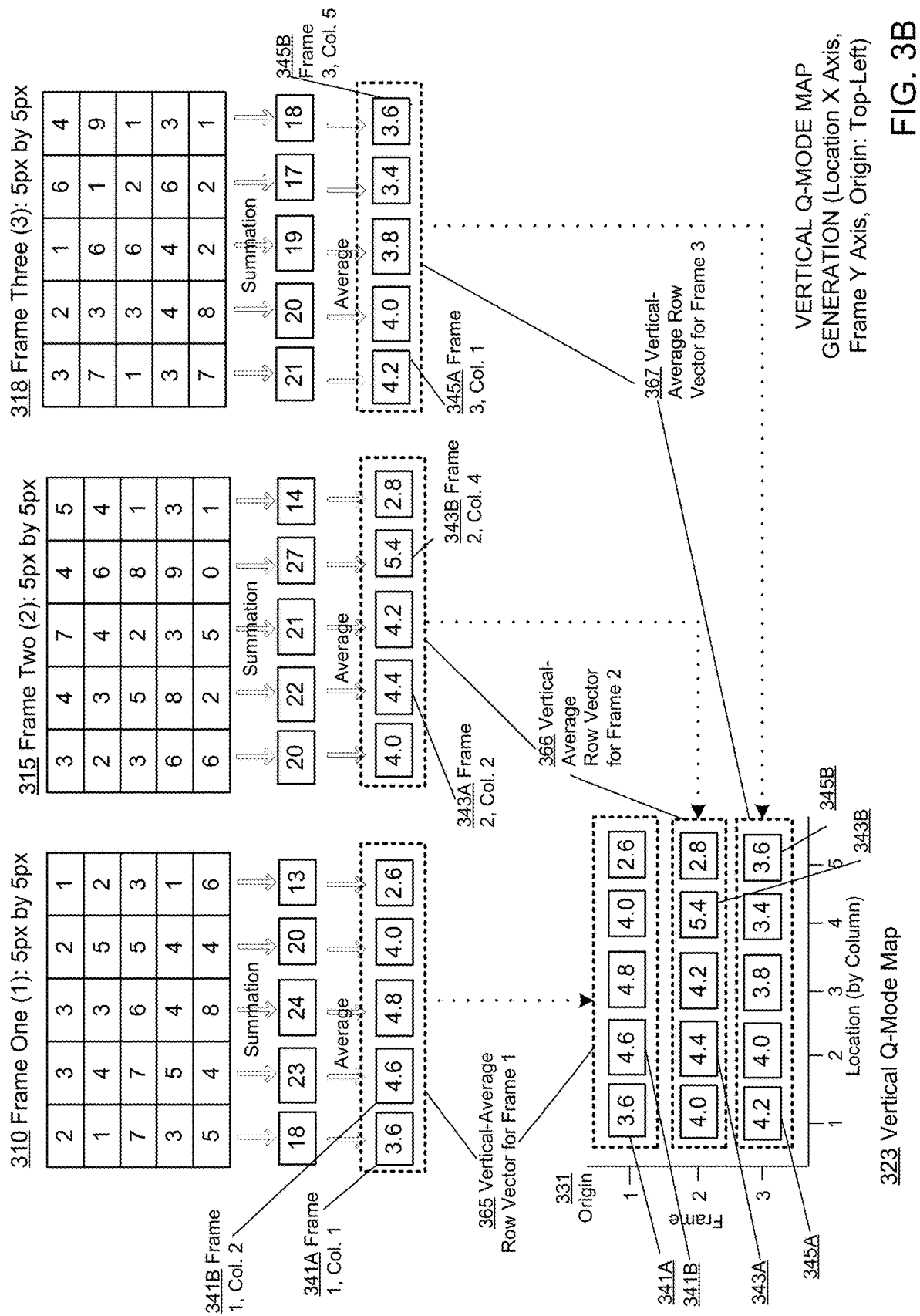
Figure 3C:
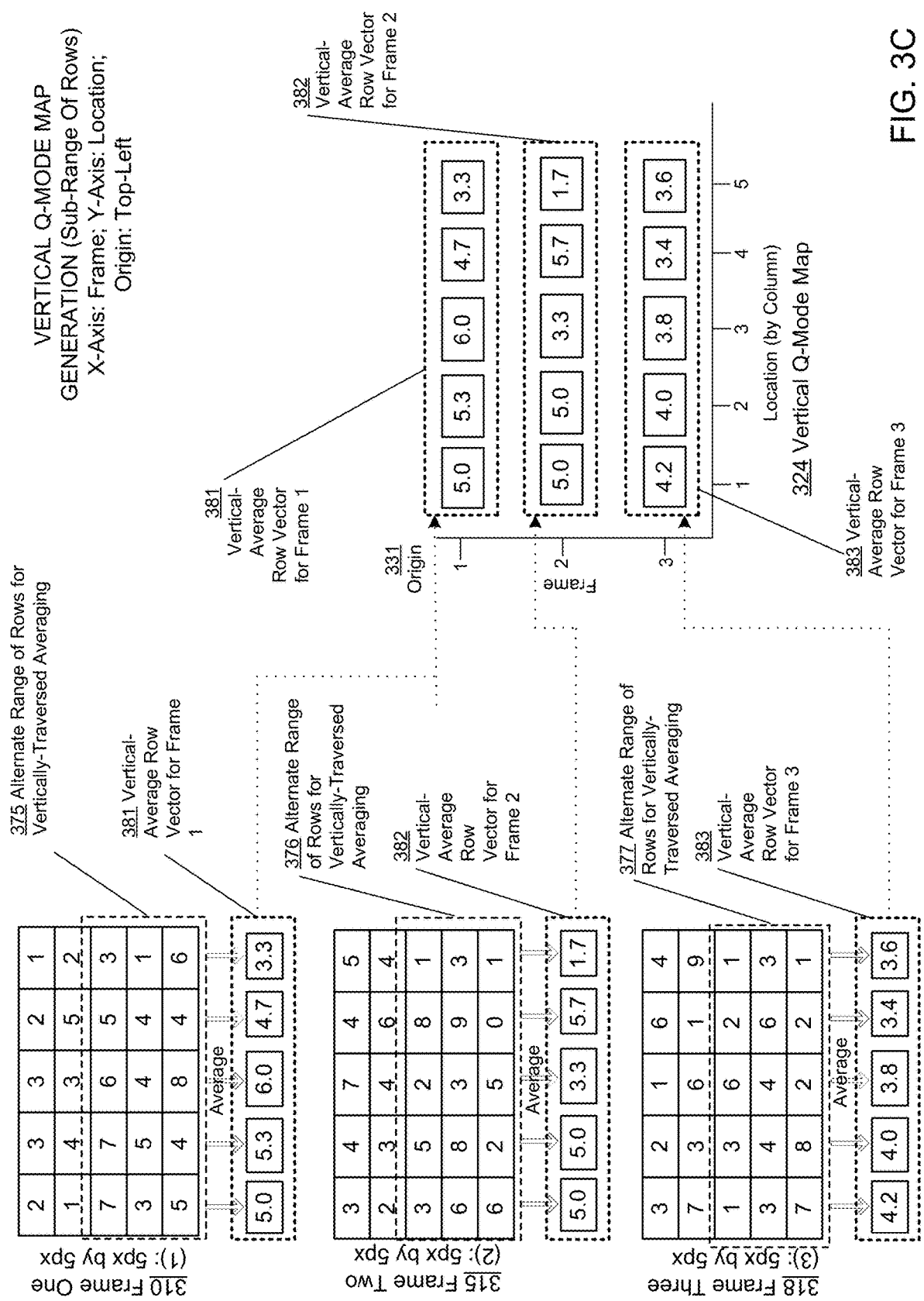
Figure 3D:
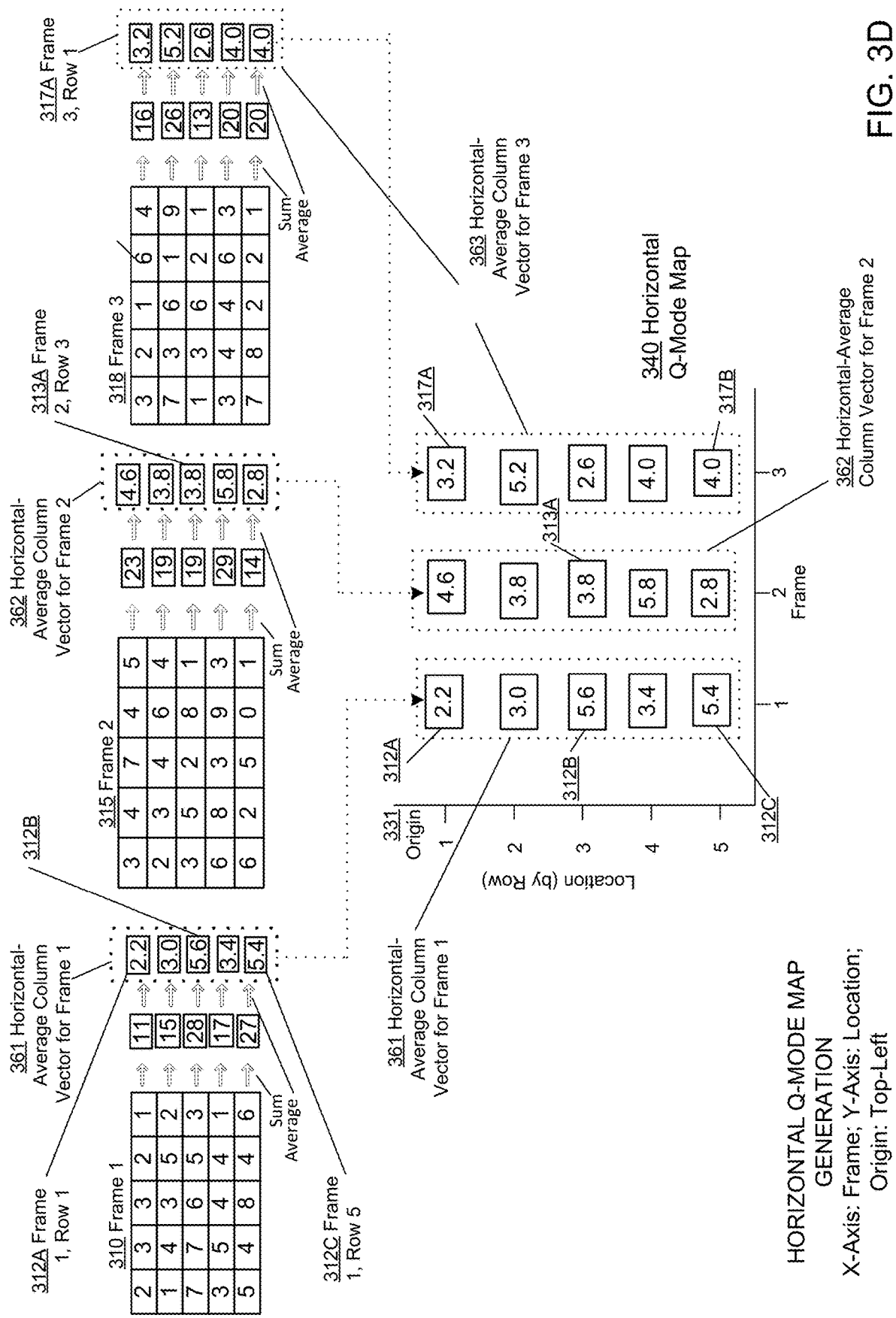
Figure 3E:
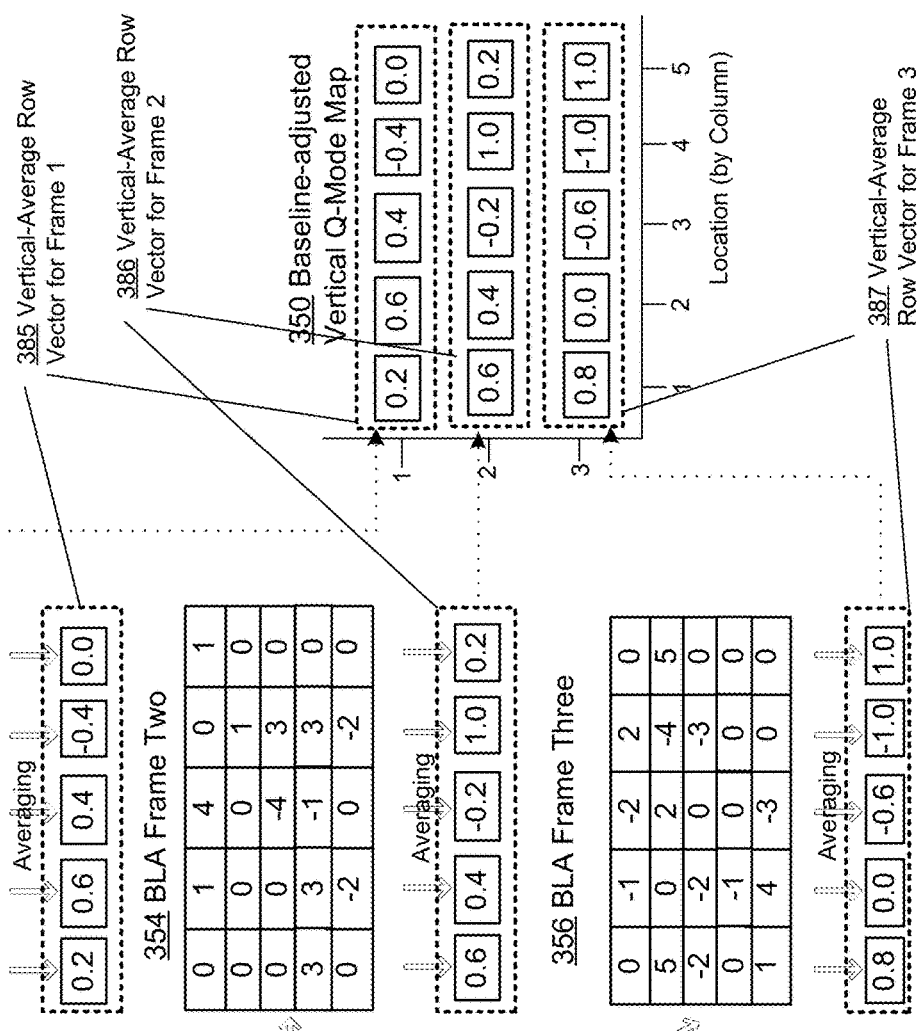

FIGS. 3B-3E show various layouts and methods for calculating vertical Q-mode maps and horizontal Q-mode maps. It is noted that not all of these layouts and methods are used in every implementation, and other layouts and methods are possible. As will be described in more detail herein, neither the specific layouts (e.g., coordinate systems, axes, and points of origin) used to generate the Q-mode maps, nor the specific algorithm for generating the various Q-mode maps, is critical to detection of B-lines. Rather, some exemplary implementations are shown in FIGS. 3B-3E, so that some examples of the generation of Q-mode maps are described and illustrated. Accordingly, FIG. 3B shows calculation of a vertical Q-mode map that shows the summation and averaging operations for each vertical-average row vector, and then the placement of each vertical-average row vector into the vertical Q-mode map, e.g., vertical Q-mode map 323, with the x-value set to the column location and the y-value set to the frame, and with the top-left as the point of origin. That is, a set of vertical-average row vectors that each correspond to a single frame is generated, and the where the values inside each vertical-average row vector represent the average of the respective vertical column inside that frame. The vertical-average row vectors are then placed in the vertical Q-mode map, top-to-bottom (e.g., with Frame 1's vector at the top or uppermost position of the vertical Q-mode map). FIG. 3C is similar to FIG. 3B, except that the averaging operation is illustrated as a single operation, and, for reasons that will be described in more detail herein, a subset or range of rows are selected for averaging. FIG. 3D shows generation of a horizontal Q-mode map through generation of horizontal-average column vectors that each correspond to a single frame, where the values inside each horizontal-average column vector represent the average of the respective horizontal rows inside that frame. The horizontal-average column vectors are then placed in the horizontal Q-mode map, left-to-right, with Frame 1's corresponding horizontal-average column vector at the leftmost position of the horizontal Q-mode map. FIG. 3E shows generation of a baseline-adjusted vertical Q-mode map similar to that shown in FIG. 3B, except with baseline-adjusted values rather than original values. The following table illustrates the relationships of FIGS. 3B-3E as follows:

TABLE 1

Comparison of Various Implementations Depicted in FIGS. 3B-3E

| Figure | Q-Mode Map Type | Full Range or Subset | X-Axis | Y-Axis | Origin |
|---|---|---|---|---|---|
| 3B | Vertical | Full Range | Col. Location | Frame No. | Top-Left |
| 3C | Vertical | Subset Range | Col. Location | Frame No. | Top-Left |
| 3D | Horizontal | Full Range | Frame No. | Col. Location | Top-Left |
| 3E | Baseline-Adjusted Vertical | Full Range | Col. Location | Frame No. | Top-Left |

As will be discussed in more detail further herein, the implementations that illustrate the bulk of the alignments and orientations for later images depicted in this application are as follows: FIG. 3B/3C for vertical Q-mode maps, FIG. 3D for horizontal Q-mode maps, and FIG. 3E for baseline-adjusted vertical Q-mode maps. What follows is a more detailed discussion of FIGS. 3B-3E. Some components are omitted between figures if they are redundant, to improve clarity and readability. FIGS. 3B-3D each use the same three exemplary ultrasound image frames, whereas FIG. 3E draws from baseline-adjusted versions of the same three exemplary frames. It is noted that, in each of the following 3B-3E, similarly to FIG. 3A, the frames illustrate a 5×5 pixel size for a total of twenty-five pixels, and similarly to FIG. 3A and throughout, this representation is for illustration purposes only. Also similarly to FIG. 3A, each cell of the exemplary frames (frame 310, frame 315, and frame 318) includes a numeric representation of the pixel intensity of that frame.

For exemplary purposes, throughout all of FIGS. 3B-3E, each of frame 310, frame 315, and frame 318 represent consecutive frames of an ultrasound video, however in practical application the frames would be much larger, e.g., "HD" resolution of 1920×1080 or other resolution used depending on the specific ultrasound device, e.g., ultrasound device 40. Moreover, in practical application, the ultrasound device would likely be operating at 20-100 Hz, generating 20-100 frames per second, rather than the three shown for exemplary purposes.

Referring now to FIG. 3B, FIG. 3B shows a calculation of the vertical Q-mode map, e.g., vertical Q-mode map 323, using three exemplary frames, frame 310, frame 315, and frame 318. As set forth above in Table 1 and the associated description, FIG. 3B illustrates a vertical Q-mode map in which the x-axis is the column location, the y-axis is the frame number, and the origin is in the top-left. The view and orientation of axes shown in FIG. 3B corresponds to the view shown in FIG. 5A, as well as to all other vertical Q-mode maps or images, except where otherwise specified. In vertical Q-mode map 323, the vertical-average row vectors are generated similarly to as shown in FIG. 3A, that is, each column is summed across a range of rows, which in the case of FIG. 3B is all rows. That sum is then divided by the number of rows that were summed in the specific column, to generate the average. That average is then placed in the vertical-average row vector, e.g., vertical-average row vector 365 for frame 310, which in FIG. 3B shows performance of an averaging of all of the columns in frame 310. It is noted that, in an implementation, the averaged pixel intensities are not rounded, but in other implementations the averaged pixel intensities may be rounded upwards, downwards, or set to a specific number of significant figures. In an implementation, averaged pixel intensity 341A, the average of the pixel intensities of Frame 1, Column 1, across all rows, is placed at the first position in vertical-average row vector 365 and thus at the top-left corner of vertical Q-mode map 323, as shown in FIG. 3B. Similarly, averaged pixel intensity 341B, the average of Frame 1, Column 2, is placed in the top row (corresponding to frame 1) and in the second column (corresponding to the column location). In a similar manner, the other averages of frame 310 are added to the first (top) row of vertical Q-mode map 323. FIG. 3B also shows how the vertical-average row vectors, e.g., vertical-average row vector 365, are added to vertical Q-mode map 323.

Continuing to refer to FIG. 3B, similarly, all of the vertical columns of frame 315 are averaged, as shown in the middle section of FIG. 3B. For example, the second column of frame 315 is averaged into averaged pixel intensity 343A, and the fourth column of frame 315 is averaged into averaged pixel intensity 343B. As illustrated, averaged pixel intensity 343A then is stored at position (2,2) of vertical Q-mode map 323, which in this orientation, with origin 331 at the top left corner, means the second column from the left, and the second row from the top. Similarly, averaged pixel intensity 343B then is stored at position (2,4) of vertical Q-mode map 323, which in this orientation means the fourth column from the left, and the second row from the top. Similarly to vertical-average row vector 365, vertical-average row vector 366, which is a one-dimensional vector representation of the averages of all of the columns of frame 315, also is shown in FIG. 3B, in its position in the second row of vertical Q-mode map 323.

Continuing to refer to FIG. 3B, the vertical columns of frame 318 then are averaged, as shown in the rightward section of FIG. 3B. For example, averaged pixel intensity 345A, the average of the pixel intensities of Frame 3, Column 1, is placed at the bottom-left corner of vertical Q-mode map 323. Similarly, averaged pixel intensity 345B, the average of the pixel intensities of Frame 3, Column 5, is placed in the bottom row (corresponding to Frame 3) and in the fifth column (corresponding to the column location). In a similar manner, the other averaged pixel intensities of the columns of frame 318 are added to the third (bottom) row of vertical Q-mode map 323. Thus, similarly to vertical-average row vector 365 and vertical-average row vector 366, vertical-average row vector 367, which is a one-dimensional vector representation of the averaged pixel intensities of all of the columns of frame 318, is shown in FIG. 3B, in its position in the third (bottom) row of vertical Q-mode map 323.

Referring now to FIG. 3C, in an implementation, FIG. 3C shows a calculation of the vertical Q-mode map, e.g., vertical Q-mode map 324, using three exemplary frames, frame 310, frame 315, and frame 318, similarly to as shown in FIG. 3B, except that not all rows will be summed in FIG. 3C to generate the vertical-average row vectors that make up vertical Q-mode map 324. That is, in various implementations, a range of pixel row locations is selected, e.g., ranges 375, 376, and 377 in FIG. 3C, and these ranges of pixel row locations are used to set a "depth range" of the image for generating vertical Q-mode maps. In various implementations, the range of pixel row locations is set by the detection of the pleural line, e.g., only those pixel row locations below the detected pleural line (e.g., where B-lines may be detected), are included in the range of pixel row locations. Although it is possible to select a corresponding range of pixel column locations when generating the horizontal Q-mode map, and in some implementations this may be carried out, it is not needed in the examples given because the horizontal Q-mode map does not measure image depth.

Referring again to FIG. 3C, as set forth above in Table 1 and the associated description, FIG. 3C, like FIG. 3B, illustrates a vertical Q-mode map in which the x-axis is the column location, the y-axis is the frame number, the origin is the top-left. In FIG. 3C, the vertical Q-mode map 324 is generated using a subset of, e.g., three of the five rows, to generate vertical-average row vector 365, vertical-average row vector 366, and vertical-average row vector 367 in order to build vertical Q-mode map 324. Thus, the orientation and axes of vertical Q-mode map 324, like the view of vertical Q-mode map 323 of FIG. 3C, corresponds to the view shown in FIG. 5A and the view of other vertical Q-mode maps described herein.

Referring again to FIG. 3C, FIG. 3C shows performance of an average of all of the columns in frame 310. The averaging steps are illustrated in FIG. 3C with a single directional arrow (e.g., omitting the intermediary "row" of showing the summed-but-not-yet-averaged values as separately illustrated steps, as in FIG. 3B) due to space constraints and also because these procedures have been previously demonstrated in other figures, but no difference in computation or effect should be implied from this omission of the intermediate step. In an implementation, vertical-average row vector 381 is generated in a manner similar to that of vertical-average row vector 365, that is, by averaging, for each column, pixel intensity values. However, rather than averaging all of the pixel intensity values in the columns of frame 310, a range of rows, e.g., range of rows 375, are averaged. Specifically, the bottom three rows of each column (e.g., rows 3-5) are summed, and averaged by dividing by three, not five, because three rows were summed. As previously described, the averaged pixel intensities of the range of rows of each column are stored in the one dimensional vector, e.g., vertical-average row vector 381, at a position corresponding to that column's location. As shown in FIG. 3C, the vertical-average row vector 381 is then "stacked" into vertical Q-mode map 324 at the Frame 1 position, e.g., at the top row of vertical Q-mode map 324, as specified by origin 331 being in the top-left, as in the other examples and illustrations. This process is repeated for frame 315 to generate vertical-average row vector 382, similarly to the generation of vertical-average row vector 366 of FIG. 3B, except only using the range of rows specified by range of rows 376, e.g., the bottom three rows. The same process then is repeated again for frame 318, by summing, for each column, a range of rows specified by range of rows 377, to generate vertical-average row vector 383. Then, vertical-average row vector 382 and vertical-average row vector 383 are stacked in the rows of vertical Q-mode map 324, e.g., at rows two and three of vertical Q-mode map 324, respectively, similarly to vertical-average row vector 366 and vertical-average row vector 367 as shown in previous FIG. 3B.

In the implementation depicted in FIG. 3C, various implementations, the range of pixel row locations is consistent across different frames, e.g., range 377 of frame 318 includes the same number of rows as range 376 of frame 315 and range 375 of frame 310. In various implementations, however, the range of pixel row locations need not be continuous, and does not need to extend to either "edge" of the various vertical columns, although these more complex ranges are not illustrated graphically.

FIGS. 3B-3C previously showed examples of generation of various vertical Q-mode maps, e.g., vertical Q-mode map 323 (FIG. 3B) and vertical Q-mode map 324 (FIG. 3C). Moving forward, FIG. 3D shows examples of generation of a horizontal Q-mode map. Specifically referring now to FIG. 3D, FIG. 3D shows a calculation of the horizontal Q-mode map, e.g., horizontal Q-mode map 340, using three exemplary frames, e.g., frame 310, frame 315, and frame 318. As set forth above in Table 1 and the associated description, FIG. 3D illustrates a horizontal Q-mode map in which the x-axis is the frame number, the y-axis is the row location, the origin is the top-left, and horizontal Q-mode map 340 includes a stacking of horizontal-average column vectors, as will be described herein.

FIG. 3D shows a similar procedure as shown in FIG. 3A, to generate a horizontal Q-mode map, e.g., horizontal Q-mode map 340. For exemplary purposes, FIG. 3D uses the same frames as in prior FIGS. 3B-3C, e.g., frame 310 (frame one), frame 315 (frame two), and frame 318 (frame three). As shown in FIG. 3D, for each of frame 310, frame 315, and frame 318, the rows are summed horizontally, e.g., across the columns of the frame, and then divided by the sum of the number of columns that were summed. That averaged pixel intensity of each row of each frame is placed in a one-dimensional vector, e.g., horizontal-average column vector 361, at a location corresponding to the row location that was averaged. These horizontal-average column vectors then are "stacked" side by side, starting on the far left as specified by origin 331, to form horizontal Q-mode map 340. Specifically, FIG. 3D shows three horizontal-average column vectors, e.g., horizontal-average column vector 361 corresponding to Frame 1, horizontal-average column vector 362 corresponding to Frame 2, and horizontal-average column vector 363 corresponding to Frame 3.

Put another way, in an implementation, horizontal-average column vector 361 is generated with respect to frame 310 by summing, for each row, pixel intensity values of that row across each column, dividing the sum by the number of columns summed to compute the average, and storing the averaged pixel intensity in the horizontal-average column vector, e.g., horizontal-average column vector 361, at a position corresponding to the row location. As shown in FIG. 3D, the horizontal-average column vector 361 is then "stacked" or adjoined to horizontal Q-mode map 340 at the Frame 1 position, e.g., at the leftmost column of horizontal Q-mode map 340, with the top averaged horizontal row pixel intensity value corresponding to the top row of horizontal Q-mode map 340. This process is repeated for frame 315 to generate horizontal-average column vector 362 and for frame 318 to generate horizontal-average column vector 363. Then, horizontal-average column vector 362 and horizontal-average column vector 363 are stacked along the columns of vertical Q-mode map 324, ascending rightward, e.g., at columns two and three of horizontal Q-mode map 340, respectively. Regarding individual pixel intensities, these are also illustrated in FIG. 3D for purposes of reference and illustration, and another way of understanding the generation of the horizontal Q-mode map 340. Specifically, the first horizontal row of the first frame, e.g., frame 310, is averaged into averaged pixel intensity 312A, which represents the average of the pixel intensities of Row 1, across all columns, of Frame 1 of the ultrasound video image represented by frame 310. Similarly, as shown in FIG. 3D, the third and fifth rows of Frame 1 are averaged into averaged pixel intensity 312B and averaged pixel intensity 312C, respectively. These averages are then adjoined to the horizontal Q-mode map 340, with the row location of the averaged pixel intensity as the y-value (e.g., vertical position), and the frame number as the x-value (e.g., the horizontal position), with the top-left of the graph being the origin 331 (0,0). In the first frame, e.g., frame 310, the averaged pixel intensity 312A of Frame 1, Row 1, is plotted at position (1,1) of the illustration which may be the topmost and left-most pixel of the horizontal Q-mode map 340. Thus, averaged pixel intensity 312A is plotted in the topmost row and left-most column making up horizontal Q-mode map 340, averaged pixel intensity 312B is plotted in the middle row and left-most column, and averaged pixel intensity 312C is plotted at the bottom row and left most column of horizontal Q-mode map 340.

Similarly, an exemplary horizontal average of frame 315 labeled in FIG. 3D, e.g., averaged pixel intensity 313A, representing the horizontal average across the columns of Frame 2, Row 3 (frame 315), is positioned in the middle row and the middle column of horizontal Q-mode map 340. Referring again to FIG. 3D, the horizontal average across the columns of Frame 3, Row 1 (frame 318), e.g., averaged pixel intensity 317A, representing the average of the first row of frame 318, and the exemplary horizontal average across the columns of Frame 3, Row 5, e.g., averaged pixel intensity 317B, representing the averaged pixel intensity of the fifth row of frame 318, are placed in the third column and in the top-most and bottom-most row, respectively, as shown in FIG. 3D.

In other portions of this application, reference is made to a baseline-adjusted vertical Q-mode map, which is calculated in the same manner as the vertical Q-mode map 324 and vertical Q-mode map 323, except that, prior to averaging, each "cell" of each frame has its pixel intensity reduced by a baseline number, which may be specific to that cell. In various embodiments, this baseline number may be the median pixel intensity of all of the intensity values of that pixel location across all the frames that make up the ultrasound video. This will be discussed in more detail with respect to FIG. 3E.

Specifically referring now to FIG. 3E, FIG. 3E shows a calculation of the baseline-adjusted vertical Q-mode map, e.g., baseline-adjusted vertical Q-mode map 350, from baseline-adjusted frames, e.g., baseline adjusted frame 352 (Frame 1), baseline adjusted frame 354 (Frame 2), and baseline-adjusted frame 356 (Frame 3). As set forth above in Table 1 and in the associated description, FIG. 3E shows a baseline-adjusted vertical Q-mode map, e.g., baseline-adjusted vertical Q-mode map 350, oriented in the same manner as vertical Q-mode map 324 of FIG. 3C, in which the x-axis is the column location, the y-axis is the frame number, and the origin is the top-left. The baseline-adjusted vertical Q-mode map 350 is generated through vertical-average row vectors, e.g., vertical-average row vector 385, vertical-average row vector 386, and vertical-average row vector 387. Accordingly, the view of baseline-adjusted vertical Q-mode map 350 of FIG. 3E corresponds to other baseline-adjusted vertical Q-mode maps and/or images illustrated throughout this document, e.g., baseline-adjusted vertical Q-mode image 1610 of FIG. 16, baseline-adjusted vertical Q-mode image 712 of FIG. 7B, and baseline-adjusted vertical Q-mode image 714 of FIG. 7B.

In other portions of this application, reference is made to the various values used as a baseline, e.g., pixel intensity values from a specific frame, median pixel values, or average pixel values. Similarly to FIGS. 3A-3D, FIG. 3E uses a set of exemplary frames, e.g., frame 310, frame 315, and frame 318. These frames are illustrated in FIG. 3E using their pre-adjustment (original) pixel intensity values on the left side of the figure. In FIG. 3E, the baseline values are set by baseline adjustment value table 355, which shows the median pixel intensity values taken from the exemplary frames, e.g., frame 310 (Frame 1), frame 315 (Frame 2), and frame 318 (Frame 3). Although the depicted implementation shows a table or map of baseline values to adjust the image, e.g., baseline adjustment value table 355, other implementations rely on values from a specific frame of the ultrasound video, or values derived from some other mathematical or statistical selection.

Referring again to FIG. 3E, FIG. 3E shows, starting on the left, a transformation of the pre-adjustment frames into the baseline adjusted frames. For example, frame 310 is adjusted by subtracting, for each pixel intensity at a particular pixel location, the median pixel intensity at that location. Thus, in implementations in which the pixel intensity at a particular pixel location of frame 310 is the median value of the frames, the resulting value of baseline adjusted frame 352 will be zero (e.g., as shown in Row 1, Column 2 of baseline adjusted frame 352, where the median value is "3" taken from frame 310 (e.g., selected from the set {3, 4, 2}), making the resultant baseline-adjusted pixel intensity value of baseline adjusted frame 352 have a value of zero). By processing each frame as described, frame 310, frame 315, and frame 318 may be transformed into baseline adjusted frame 352, baseline adjusted frame 354, and baseline-adjusted frame 356, respectively, as shown in FIG. 3E.

Once the baseline-adjusted frames have been generated as previously described, the baseline-adjusted vertical Q-mode map 350 may be generated from the baseline-adjusted frames in the same manner as described in FIGS. 3B and 3C. Specifically, in an implementation, vertical-average row vector 385 is generated by averaging, for each column, the baseline-adjusted pixel values across each row, and storing the average in the vertical-average row vector, e.g., vertical-average row vector 385, at a position corresponding to the column location. As shown in FIG. 3E, the vertical-average row vector 385 is then "stacked" into baseline-adjusted vertical Q-mode map 350 at the Frame 1 position, e.g., at the top row of baseline-adjusted vertical Q-mode map 350. This process then is repeated for baseline adjusted frame 354 to generate vertical-average row vector 386, and for baseline-adjusted frame 356 to generate vertical-average row vector 387. Then, vertical-average row vector 386 and vertical-average row vector 387 are stacked in the rows of baseline-adjusted vertical Q-mode map 350, e.g., at rows two and three of baseline-adjusted vertical Q-mode map 350, respectively. Although not illustrated in FIG. 3E specifically due to space constraints, pixel row ranges, such as pixel row ranges 375, 376, and 377 from FIG. 3C, may be applied to the generation of baseline-adjusted vertical Q-mode map 350 of FIG. 3E just as in the generation of vertical Q-mode map 324 of FIG. 3C. This is because, similarly to the vertical Q-mode map, the baseline-adjusted vertical Q-mode map also may have variable depth range, which functions in substantially the same manner and for substantially the same reasons as vertical Q-mode map 324 of FIG. 3C.

With the specific graphical illustration of generation of the various Q-mode maps substantially concluded, reference now is made to FIG. 2A, which depicts an implementation of device 50, and specifically processing circuit 250 and other related components of device 50. Specifically, FIG. 2A shows a device 50 according to one or more implementations. As shown in FIG. 2A, device 50 may include a processor 222, a device memory 245, a device interface component 220, and other device components 224. These components will be discussed in more detail herein. It is noted that this is not a complete list of components of device 50, and some components that are listed may be omitted or performed elsewhere. For example, in a distributed environment, the device memory 245 may be physically separated from device 50, and may be, for example, a shared memory. Similarly, processor 222 may be a distributed processor.

As set forth above, in one or more various implementations, device 50 may include a device memory 245. In an embodiment, device memory 245 may include one or more of random access memory ("RAM"), read only memory ("ROM"), flash memory, hard drives, disk-based media, disc-based media, magnetic storage, optical storage, volatile memory, nonvolatile memory, and any combination thereof. In an embodiment, device memory 245 may be separated from the device, e.g., available on a different device on a network, or over the air. For example, in a networked system, there may be one or more devices 50 whose device memory 245 is located at a central server that may be a few feet away or located across an ocean. In an embodiment, device memory 245 may include one or more mass storage devices, read-only memory (ROM), programmable read-only memory (PROM), erasable programmable read-only memory (EPROM), cache memory such as random access memory (RAM), flash memory, synchronous random access memory (SRAM), dynamic random access memory (DRAM), and/or other types of memory devices. In an embodiment, device memory 245 may be located at a single network site. In an embodiment, device memory 245 may be located at multiple network sites, including sites that are distant from each other.

As set forth above, in one or more various implementations, device 50 may include a device interface component 220, as shown in FIG. 2A. As described herein, device interface component 220 is intended to represent all of the components that handle input and output of device 50, e.g., the interactions with operator 140. For ease of explanation, in various implementations, device interface component 220 may include a device input component 220A and a device output component 220B. Although shown separately in FIG. 2A and as described throughout this application, it is noted that there may be substantial overlap, in both hardware and software/programming, between device input component 220A and device output component 220B. For example, a touchscreen monitor may serve as both part of device input component 220A and device output component 220B. Each of device input component 220A and device output component 220B may include many various components and the associated drivers, programs, and software that allow those components to function. In various implementations, an incomplete, non-limiting list of components that may be included in device input component 220A include a keyboard, a keypad, a gamepad, a touchscreen, a microphone, a headset, a gesture tracker, an optical tracker, a camera, and a webcam, or any combination thereof. In various implementations, an incomplete, non-limiting list of components that may be included in device output component 220B include a display, a touchscreen, a projector, an augmented reality projection, a virtual reality projection, a speaker, a set of headphones, and a haptic feedback.

Additionally, device interface component 220 may include the circuits formed by software programs that allow interaction with device 50, e.g., a computer. For example, in an implementation where device 50 is a computer, device interface component 220 may include the circuitry formed by software programs that make up a web browser. The web browser circuitry, in some implementations, allows interaction with the user to reach the circuitry that is claimed in this invention. This circuitry may alternatively be part of processor 222, and may be integrated into the circuitry that is claimed in this invention, though explicitly not claimed as part of the invention to allow for the contemplation of various interfaces. As another example, in an implementation where device 50 is a smartphone, e.g., an Apple iPhone or a Samsung phone running android, and connected to a various "app store" or "play store," an application that configures the circuitry of processor 222 into the circuits claimed in the invention, may interface with the circuitry of processor 222 that allows operator 140 to interact with the smartphone device, e.g., through device interface component 220.

As set forth above, in one or more various implementations, device 50 may include a device interface component 220, as shown in FIG. 2A. As described herein, device interface component 220 is intended to represent all of the components that handle input and output of device 50, e.g., the interactions with operator 140. For ease of explanation, in various implementations, device interface component 220 may include a device input component 220A and a device output component 220B. Although shown separately in FIG. 2A and as described throughout this application, it is noted that there may be substantial overlap, in both hardware and software/programming, between device input component 220A and device output component 220B. For example, a touchscreen monitor may serve as both part of device input component 220A and device output component 220B. Each of device input component 220A and device output component 220B may include many various components and the associated drivers, programs, and software that allow those components to function. In various implementations, an incomplete, non-limiting list of components that may be included in device input component 220A include a keyboard, a keypad, a gamepad, a touchscreen, a microphone, a headset, a gesture tracker, an optical tracker, a camera, and a webcam, or any combination thereof. In various implementations, an incomplete, non-limiting list of components that may be included in device output component 220B include a display, a touchscreen, a projector, an augmented reality projection, a virtual reality projection, a speaker, a set of headphones, and a haptic feedback.

As set forth above, in one or more various implementations, device 50 may include other device components 224. Other device components 224 are primarily shown for illustration, e.g., that the list of components set forth here for device 50 is not intended to be an exhaustive or complete list. For example, other device components 224 may include, for example, an operating system (OS) or kernel 223. In other implementations, other device components 224 may include a graphics card, a GPU, processors other than processor 222, persistent storage, and other components known in the art as optionally part of device 50. In various implementations, other device components 224 may include a probe 42, e.g., in implementations where ultrasound device 40 is omitted or is part of device 50.

Referring again to FIG. 2A, device 50 may include processor 222, as previously described. In an implementation, processor 222 may be configured by instructions to form processing circuit 250. In another implementation, processing circuit 250 may be a persistent part of processor 222, e.g., in the form of an Application-Specific Integrated Circuit (ASIC) or a Field Programmable Gate Array (FPGA). In an implementation, only portions of processing circuit 250 may exist at any given snapshot in time, as processor 222 executes instructions and then re-purposes its logic gates and transistors in accordance with the instructions that are received. In an implementation, e.g., in an implementation in which processor 222 executes pipelining of instructions, portions of processing circuit 250 may not exist all at the exact same instant in time, but are formed to completion as processor 222 forms itself based on instructions received.

Figure 2B:
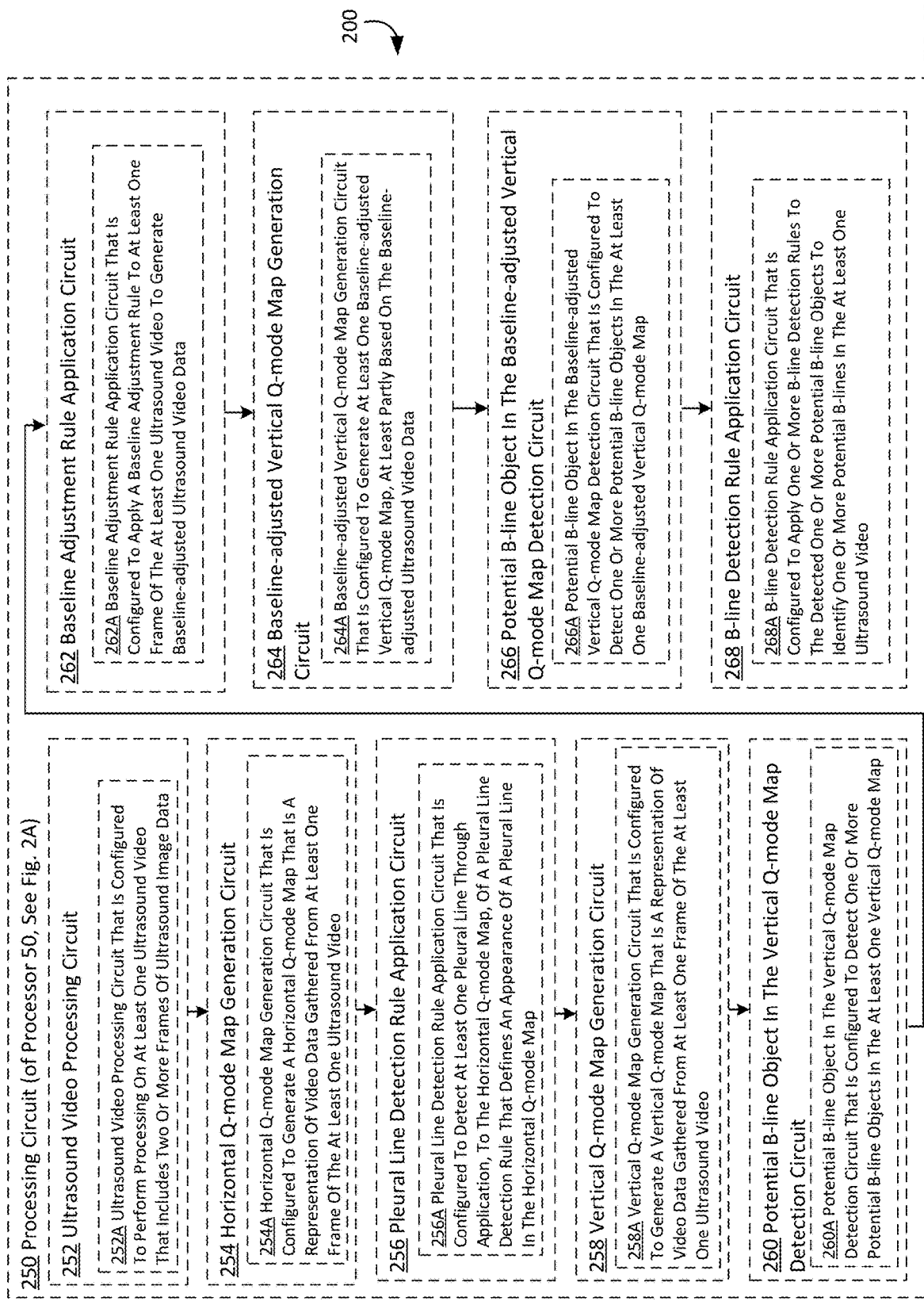

Referring again to FIG. 2A, FIG. 2A shows processing circuit 250, including the various circuits used to carry out one machine-based implementation of the invention. FIG. 2A shows a high-level diagram of the various circuits that are included in processing circuit 250, and the interaction with other components of device 50. FIG. 2B provides more detail regarding each of the various circuits found in FIG. 2B, which shows substantially the same implementation as FIG. 2A, but in greater detail and without illustrating the other components of device 50. processing circuit 250 may include, at one or more times, and not necessarily concurrently or in the order shown in FIG. 2A, an ultrasound video processing circuit 252, a horizontal Q-mode map generation circuit 254, a pleural line detection rule application circuit 256, a vertical Q-mode map generation circuit 258, a potential B-line object in the vertical Q-mode map detection circuit 260, a baseline adjustment rule application circuit 262, a baseline-adjusted vertical Q-mode map generation circuit 264, a potential B-line object in an adjusted Q-mode map detection circuit 266, and a B-line detection rule application circuit 268. It is noted that in FIGS. 2A, 2B, and other figures, various arrows are used. As set forth above, when used in device diagrams, e.g., as in FIGS. 2A, 2B, and others, these arrows may be used to indicate exemplary but non-limiting data flow, for ease of understanding. Although the arrows may coincidentally align with steps to be carried out, such arrows do not necessarily imply a set order or a causal relationship, unless context dictates otherwise. As set forth above, although similar in appearance to arrows appearing in flow diagrams, arrows in circuit and device diagrams represent data flow and are not limited by their arrow direction.

As shown in FIGS. 2A and 2B, in one or more implementations, ultrasound video processing circuit 252 may be configured to perform processing on at least one ultrasound video that includes two or more frames of ultrasound image data 252A. The processing performed by ultrasound video processing circuit 252 may include various forms of pre-processing for images, which in various embodiments may be grayscale images. For example, in an implementation, edge detection using various known implementations may be used, with a modifier to arrive at a rectangular image (e.g., for ease in creating the vertical Q-mode maps and horizontal Q-mode maps, as will be described in more detail herein). Other processing that may be carried out by ultrasound video processing circuit 252 may include cropping unwanted portions of the image, or conversion of the image from one coordinate plane to another, e.g., conversion of a polar-coordinate plane image into a Cartesian coordinate plane image. In other implementations, more advanced processing may be performed on the image, e.g., brightness filters, geometric transformations, etc., to the extent such processing avoids corruption of the raw image data needed to perform the necessary work on the image. Specific types of image processing that are useful for one implementation of the herein-described processes will be discussed in more detail herein.

Referring again to FIG. 2A, in an implementation, ultrasound video processing circuit 252 may carry out operation 922 of FIG. 9B, preparing, for processing, at least one ultrasound video that includes two or more frames, and/or portions of operation 902 of FIG. 9A, generating at least one Q-mode map from at least one ultrasound video, which will be discussed in more detail further herein with respect to the respective figures. In an implementation, ultrasound video processing circuit 252 interacts with device interface component 220 to provide visual output of the ultrasound video, although this step is not necessary or required.

Referring again to FIG. 2A, in an implementation, processing circuit 250 may include horizontal Q-mode map generation circuit 254, in various implementations. As shown in FIG. 2B, e.g., in sub-operation 254A, horizontal Q-mode map generation circuit 254 may be configured to generate a horizontal Q-mode map at least partly based on the processed at least one ultrasound video. In an implementation, horizontal Q-mode map generation circuit 254 may generate a horizontal Q-mode map, e.g., horizontal Q-mode map 340, in a process described in more detail with respect to FIG. 3D. Moreover, in an implementation, horizontal Q-mode map generation circuit 254 may carry out operation 924 of FIG. 9B, generating a horizontal Q-mode map that is a representation of video data gathered from at least one frame of the at least one ultrasound video, and/or portions of operation 902 of FIG. 9A, generating at least one Q-mode map from at least one ultrasound video, which will be discussed in more detail further herein with respect to the referenced figures.

Figure 2C:
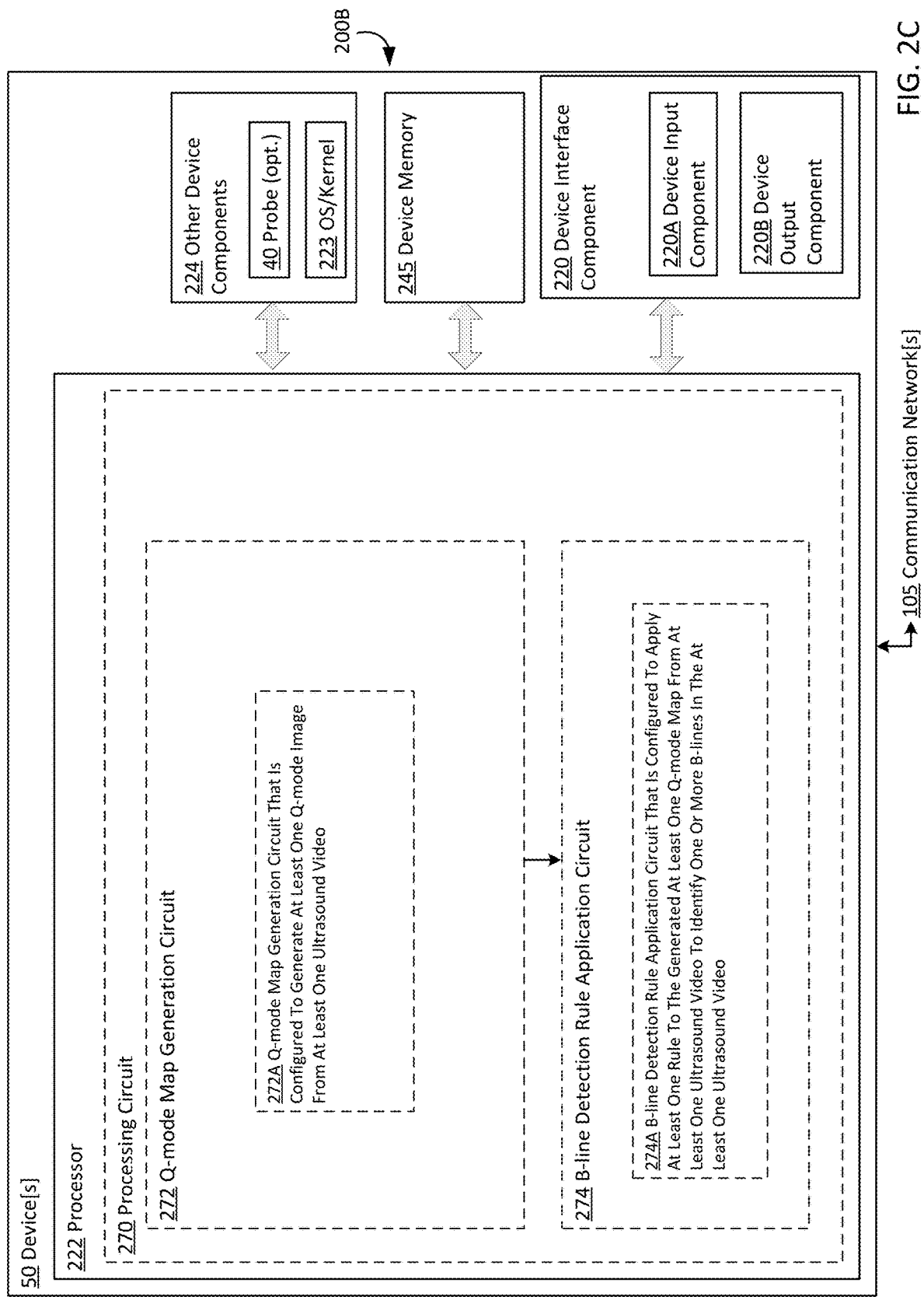
Figure 2D:
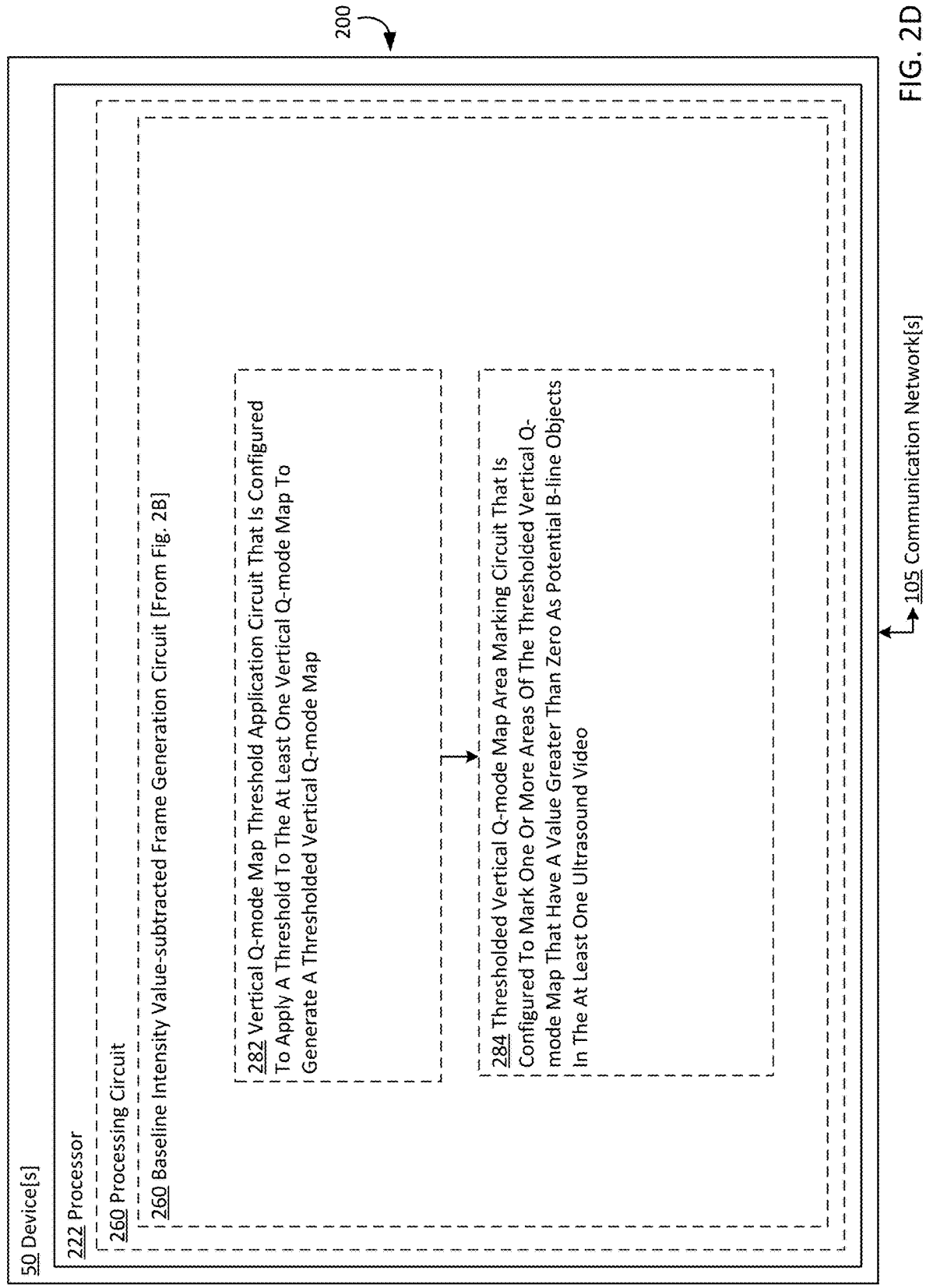
Figure 2E:
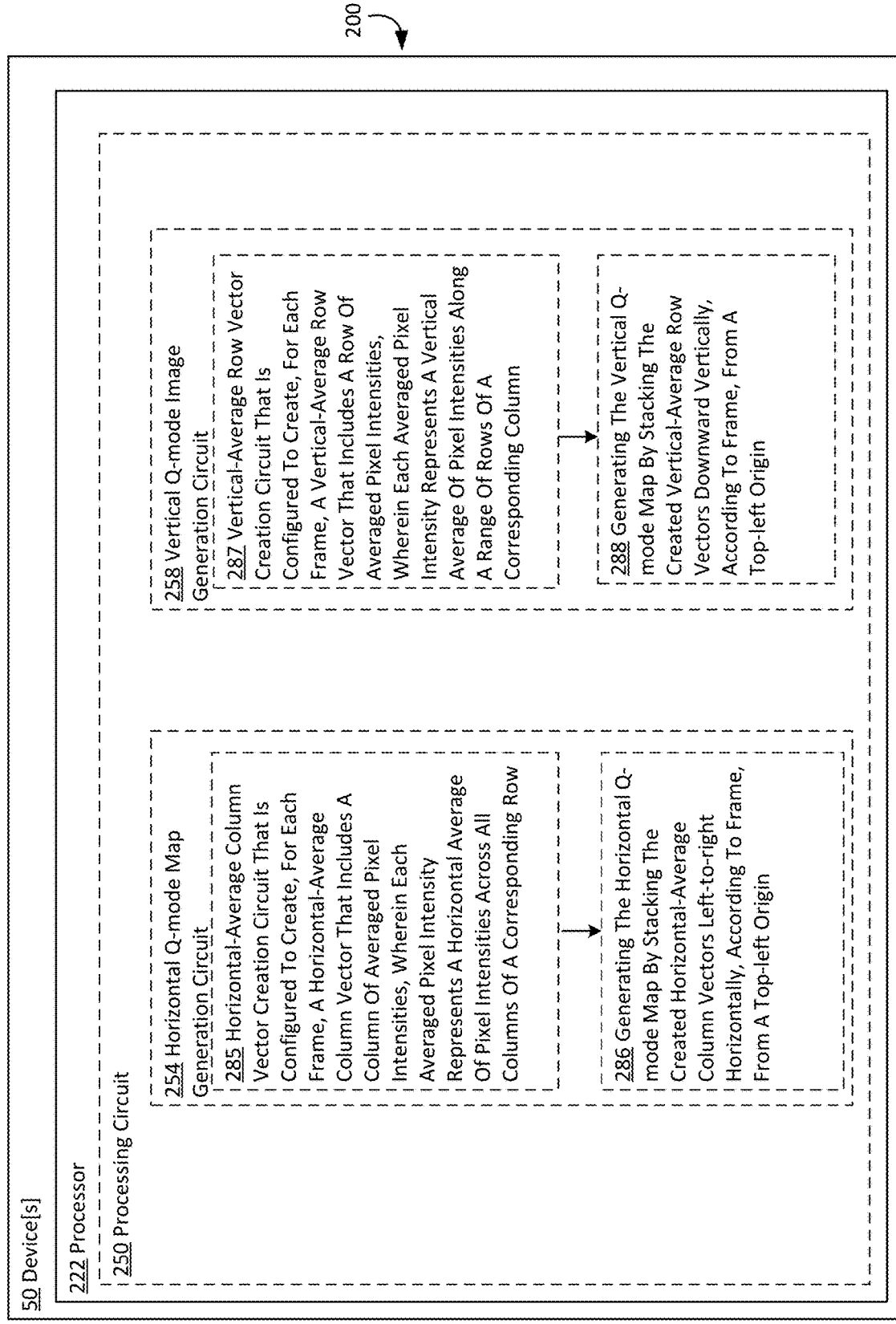

In an implementation, the horizontal Q-mode map may be generated by horizontal Q-mode map generation circuit 254 through a number of techniques, some of which are illustrated in FIG. 3 and described in FIG. 2E. For example, FIG. 2E describes a horizontal Q-mode map generation circuit 254 which, in an implementation, may include a horizontal-average column vector creation circuit 285 that is configured to create a horizontal-average column vector (e.g., horizontal-average column vector 361 of FIG. 3D). The horizontal-average column vector may be a column vector that includes a column of averaged pixel intensities. Each averaged pixel intensity in the horizontal-average column vector represents an average of pixel intensities across all columns of a corresponding row (e.g., horizontally summing pixel intensities across all columns of a corresponding row and dividing by the number of columns summed). This process is described in more detail herein with respect to FIG. 3D. By way of illustrative example, an exemplary Row 5 of Frame 12 of an ultrasound video may have various pixel intensities. For purposes of the example, assuming Frame 12 has sixty columns, the pixel intensities of the pixels across all of the sixty columns of Row 5 of Frame 12 are summed together. This sum is then divided by the total number of values (e.g., total number of columns) that were summed (e.g., sixty), to generate the average value. This average value is then placed in the horizontal-average column vector, e.g., at position 5 of that particular horizontal-average column vector. As will be described in the next paragraph, this particular horizontal-average column vector will be "stacked" twelfth from the left, indicating that the horizontal-average column vector was generated from Frame 12.

Additionally, as shown in FIG. 2E, horizontal Q-mode map generation circuit 254 also may include horizontal Q-mode map generation circuit 286, which, in an implementation, may be configured to generate the horizontal Q-mode map through stacking the created horizontal-average column vectors, created as described in the previous paragraph, left-to-right horizontally, according to frame, from a top-left origin, e.g., as illustrated in FIG. 3D.

Referring back to FIG. 2A, in an implementation, processing circuit 250 may include pleural line detection rule application circuit 256. For example, in an implementation, e.g., as shown in sub-operation 256A of FIG. 2B, the pleural line detection rule application circuit 256 may be configured to detect at least one pleural line through application, to the horizontal Q-mode map, of a pleural line detection rule that defines an appearance of a pleural line in the horizontal Q-mode map. As mentioned above, pleural lines run substantially horizontally in a lung ultrasound video that is mapped in a Cartesian coordinate plane. Accordingly, the horizontal Q-mode map, which emphasizes areas where horizontal lines are detected, may be useful in determining a location of the pleural line in the lung ultrasound. In an implementation, detection of the pleural line is useful in later processing to determine whether objects detected in the image represent B-lines or other artifacts (e.g., see the following discussion herein regarding ultrasound image artifacts). In various implementations, after this detection of the pleural line is performed, areas above the pleural line, which in some embodiments may not contain B-lines, do not have further processing performed on them. For example, as previously described, in an implementation, once the pleural line is detected, a depth range may be selected for the various vertical Q-modes, e.g., as described with respect to FIG. 3C, such that a range of rows is selected to exclude rows that are above the row detected as containing the pleural line. In an implementation, pleural line detection rule application circuit 256 may carry out operation 926 of FIG. 9B, detecting at least one pleural line through application, to the horizontal Q-mode map, of a pleural line detection rule that defines an appearance of a pleural line in the horizontal Q-mode map, and/or portions of operation 902 of FIG. 9A, generating at least one Q-mode map from at least one ultrasound video, which will be discussed in more detail further herein with respect to the respective figures.

Referring again to FIG. 2A, in an implementation, processing circuit 250 of processor 222 may include vertical Q-mode map generation circuit 258. In an implementation, as shown in FIG. 2B, vertical Q-mode map generation circuit 258 may be configured to generate a vertical Q-mode map that is a representation of data gathered from at least one frame of the ultrasound video, as shown in sub-operation 258A. In an implementation, vertical Q-mode map generation circuit 258 may generate a vertical Q-mode map, e.g., vertical Q-mode map 323 or vertical Q-mode map 324 in FIGS. 3B-3C, respectively, in a process described in more detail with respect to FIGS. 3B-3C. Moreover, in an implementation, vertical Q-mode map generation circuit 258 may carry out operation 928 of FIG. 9B, generating at least one vertical Q-mode map that is a representation of data gathered from at least one frame of the at least one ultrasound video, and/or portions of operation 902 of FIG. 9A, generating at least one Q-mode map from at least one ultrasound video, which will be discussed in more detail further herein with respect to the respective figures. In an implementation, the vertical Q-mode map may be generated by vertical Q-mode map generation circuit 258 through a number of different techniques, some of which are illustrated in FIG. 3 and described in FIG. 2E. For example, FIG. 2E describes a vertical Q-mode map generation circuit 258 that, in an implementation, includes a vertical-average row vector creation circuit 287 that is configured to create a vertical-average row vector (e.g., vertical-average row vector 365 of FIG. 3B). The vertical-average row vector 365 may be a row vector that extends horizontally and that includes a row of averaged pixel intensities. Each averaged pixel intensity in the vertical-average row vector 365 represents an average of pixel intensities across a range of rows of the corresponding column (e.g., vertically traversing pixel intensities down a range of rows of a corresponding column and averaging by summing up the pixel intensities and dividing by the number of rows summed). This process is more precisely illustrated in FIGS. 3B-3C. By way of illustrative example, an exemplary Column 19 of Frame 10 may have various pixel intensities. For purposes of the example, assuming Frame 10 has eighty columns and eighty rows, the pixel intensities of the pixels along all of the eighty rows of Column 19 of Frame 10 are added together. This total is then divided by the total number of values (e.g., total number of rows) that were summed (e.g., eighty), to generate the average pixel intensity value. This average pixel intensity value then is placed in the vertical-average row vector, e.g., at position 19 of that particular vertical-average row vector. As will be described in the next step, this particular vertical-average row vector will be stacked tenth from the top, indicating that the vertical-average row vector was generated from Frame 10. Accordingly, in an implementation, vertical-average row vector creation circuit 287 may generate the vertical Q-mode map through placement of a sequence of frame-based one dimensional horizontal vectors, e.g., vertical-average row vector 365 from FIG. 3C, below one another in descending order (e.g., downward, although the frame number will be increasing because the origin is at the top-left).

In an implementation e.g., as shown in FIG. 2E, the vertical Q-mode map may be generated by vertical Q-mode map generation circuit 258, which in an implementation also may include the vertical Q-mode map generation circuit 288 of FIG. 2E that generates the vertical Q-mode map by stacking the created vertical-average row vectors downward vertically according to frame, e.g., as shown in FIG. 3B with respect to vertical-average row vector 365, vertical-average row vector 366, and vertical-average row vector 367. As previously mentioned, the vertical Q-mode map may be selected with the frame number and the vertical column number along various axes, and with different points of origin, without affecting the operation of the various detection algorithms, but which may reduce human capacity to understand and/or visualize the Q-mode data, in implementations where such is made available for human review.

In an implementation, vertical Q-mode map generation circuit 258 may carry out operation 928 of FIG. 9B, e.g., generating at least one vertical Q-mode map that is a representation of data gathered from at least one frame of the at least one ultrasound video, which will be discussed in more detail herein with respect to FIG. 9B.

Referring again to FIG. 2A, in an implementation, processing circuit 250 of processor 222 may include potential B-line object in the vertical Q-mode map detection circuit 260. In an implementation, as shown in FIG. 2B, potential B-line object in the vertical Q-mode map detection circuit 260 may be configured to detect one or more potential B-line objects in the vertical Q-mode map, as shown in sub-operation 260A. This may be accomplished by, for example, thresholding the vertical Q-mode map, and detecting a potential B-line object at any location in the vertical Q-mode map where pixel intensities greater than zero are detected after thresholding. In another implementation, areas where pixel intensities greater than zero are detected after thresholding may be clustered together, e.g., as will be described in more detail with respect to FIG. 18. In an implementation, potential B-line objects may be marked at an average or midpoint location of an area in the vertical Q-mode map where pixel intensities greater than zero are detected after thresholding. In an implementation, potential B-line object detection on the vertical Q-mode map may tend to detect merged B-lines or otherwise prominent B-lines which could be canceled out otherwise when performing baseline adjustment on the image.

In an implementation, potential B-line object in the vertical Q-mode map detection circuit 260 may carry out operation 930 of FIG. 9B, e.g., detecting one or more potential B-line objects in the at least one vertical Q-mode map, which will be discussed in more detail herein with respect to FIG. 9B.

Referring again to FIG. 2A, in an implementation, processing circuit 250 of processor 222 may include baseline adjustment rule application circuit 262. In an implementation, as shown in FIG. 2B, baseline adjustment rule application circuit 262 may be configured to apply a baseline adjustment rule to at least one frame of the at least one ultrasound video to generate baseline-adjusted ultrasound video data, as shown in sub-operation 262A. In an implementation, baseline adjustment rule application circuit 262 may apply a baseline, e.g., as shown in FIG. 3E, to one or more of the frames of the ultrasound video. In other implementations, baseline adjustment rule application circuit 262 may apply a different baseline adjustment rule that may select a frame to use as a baseline, or use one or more formulas or algorithms for determining the baseline adjustment to the at least one frame of the ultrasound video. In an implementation, the baseline-adjusted ultrasound video data may be stored and processed, but in another implementation, the baseline-adjusted ultrasound video data may be processed and discarded, e.g., once the baseline-adjusted vertical Q-mode map has been generated, as will be described herein.

In an implementation, baseline adjustment rule application circuit 262 may carry out operation 932 of FIG. 9B, e.g., applying a baseline adjustment rule to at least one frame of the at least one ultrasound video to generate baseline-adjusted ultrasound video data, which will be discussed in more detail herein with respect to FIG. 9B.

Referring again to FIG. 2A, in an implementation, processing circuit 250 of processor 222 may include baseline-adjusted vertical Q-mode map generation circuit 264. In an implementation, as shown in FIG. 2B, baseline-adjusted vertical Q-mode map generation circuit 264 may generate the baseline-adjusted vertical Q-mode map at least partly based on the baseline-adjusted ultrasound video data, as shown in sub-operation 264A. That is, through a similar process as the vertical Q-mode map, the baseline-adjusted vertical Q-mode map may be generated in the same manner using the baseline-adjusted ultrasound video data, e.g., through generating one or more vertical-average row vectors from the baseline-adjusted ultrasound video data, and stacking those vertical-average row vectors vertically, as previously described. For example, in an implementation, the baseline-adjusted vertical Q-mode map generation circuit 264 may generate baseline-adjusted vertical Q-mode map through placement of a sequence of vertical-average row vectors, e.g., vertical-average row vector 385 from FIG. 3E, below one another in descending order (e.g., downward, although the frame number will be increasing because the origin is at the top-left). Each vertical-average row vector may be constructed by calculating, for each column, an average of pixel intensities across a range of rows for that column of the baseline-adjusted frame. In contrast with the horizontal Q-mode map, and similarly to the vertical Q-mode map, the baseline-adjusted vertical Q-mode map may generate an averaged pixel intensity over only a range of rows (which may include all rows), for reasons that have been previously mentioned. That is, for each column of the particular baseline-adjusted frame, a subset of the pixel intensity values in that column will be averaged, and then that average is placed in the vertical-average row vector at a location corresponding to the location of the column that was averaged.

In an implementation, baseline-adjusted vertical Q-mode map generation circuit 264 may carry out operation 934 of FIG. 9B, e.g., generating at least one baseline-adjusted vertical Q-mode map, at least partly based on the baseline-adjusted ultrasound video data, which will be discussed in more detail herein with respect to FIG. 9B.

Referring again to FIG. 2A, in an implementation, processing circuit 250 of processor 222 may include potential B-line object in an adjusted Q-mode map detection circuit 266. In an implementation, as shown in FIG. 2B, potential B-line object in an adjusted Q-mode map detection circuit 266 may be configured to detect one or more potential B-line objects in an adjusted Q-mode map, e.g., the baseline-adjusted vertical Q-mode map (e.g., the baseline-adjusted vertical Q-mode map 350 of FIG. 3E, previously discussed in more detail. This may be accomplished by, for example, thresholding the baseline-adjusted vertical Q-mode map, and detecting a potential B-line object at any location in the baseline-adjusted vertical Q-mode map where pixel intensities greater than zero are detected after thresholding. In another implementation, areas where pixel intensities greater than zero are detected after thresholding may be clustered together, e.g., as will be described in more detail with respect to FIG. 18. In an implementation, potential B-line objects may be marked at an average or midpoint location of an area in the baseline-adjusted vertical Q-mode map where pixel intensities greater than zero are detected after thresholding. In an implementation, potential B-line object detection on the baseline-adjusted vertical Q-mode map may be more efficient, relative to the vertical Q-mode map, at detecting transient B-lines, or less prominent B-lines, due to adjustment of the frames based on a median pixel intensity.

In an implementation, the potential B-line object in an adjusted Q-mode map detection circuit 266 may carry out operation 936 of FIG. 9B, detecting one or more potential B-line objects in the baseline-adjusted vertical Q-mode map, and/or portions of operation 904 of FIG. 9A, applying at least one rule to the generated at least one Q-mode map from at least one ultrasound video to identify one or more B-lines in the at least one ultrasound video, which will be discussed in more detail further herein with respect to the respective figures.

Referring again to FIG. 2A, in an implementation, processing circuit 250 of processor 222 may include B-line detection rule application circuit 268. In an implementation, as shown in FIG. 2B, B-line detection rule application circuit 268 may be configured to apply one or more B-line detection rules to the detected one or more potential B-line objects to identify one or more potential B-lines in the at least one ultrasound video, as shown in sub-operation 268A. The one or more B-line detection rules may specify one or more portions of the at least one ultrasound video to extract, e.g., at locations specified by the detected one or more potential B-line objects, and how to further determine whether the detected potential B-line objects are true B-lines or false positives. In an implementation, B-line detection rule application circuit 268 may detect the various B-lines present in the ultrasound video through detection of one or more objects in the baseline-adjusted vertical Q-mode map, through application of one or more rules which will be discussed in more detail herein, e.g., a thresholding rule, and one or more detection and/or pattern matching rules, and then through further processing on the corresponding locations within the ultrasound video, e.g., performing machine learning on the extracted image portions, in a process that will be described in more detail further herein.

Figure 9A:
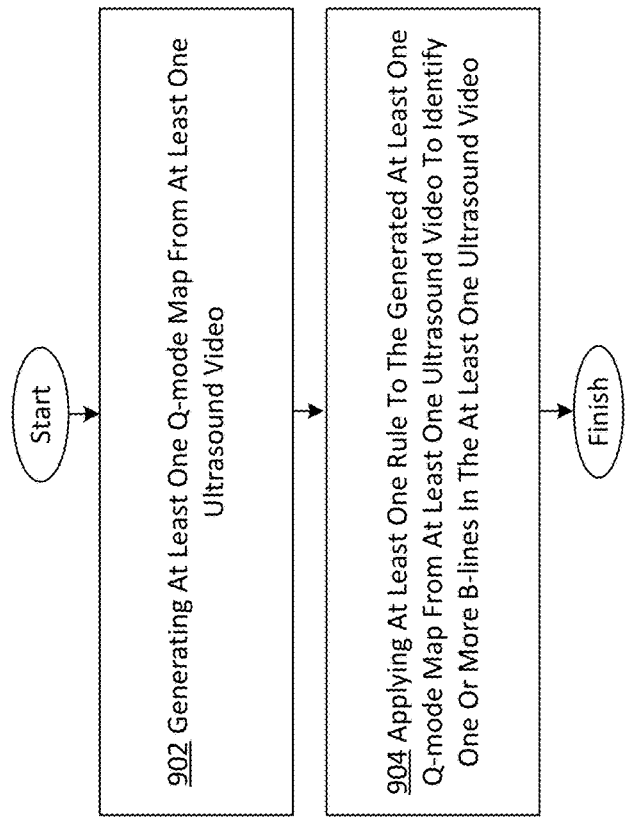
FIG. 9A is a high-level logic flowchart of a process, e.g., operational flow 900, according to various embodiments of the invention.

In an implementation, B-line detection rule application circuit 268 may carry out operation 938 of FIG. 9B, applying one or more B-line detection rules to the detected one or more potential B-line objects to identify one or more potential B-lines in the at least one ultrasound video, and/or portions of operation 904 of FIG. 9A, applying at least one rule to the generated at least one Q-mode map from at least one ultrasound video to identify one or more B-lines in the at least one ultrasound video, which will be discussed in more detail further herein with respect to the respective figures.

Referring now to FIG. 2C, FIG. 2C shows a processing circuit 270 operating in environment 200B according to other implementations of device 50. For example, in an implementation, processing circuit 270 of processor 222 of device 50 may include a Q-mode map generation circuit 272. In an implementation, Q-mode map generation circuit 272 may be configured to generate at least one Q-mode image from the at least one ultrasound video, as shown in sub-operation 272A. For example, in an implementation, Q-mode map generation circuit 272 may generate one or more of the previously-described Q-mode maps, e.g., a horizontal Q-mode map, a vertical Q-mode map, and a baseline-adjusted vertical Q-mode map. In other implementations, the vertical Q-mode map may not be generated, e.g., and the calculations may be directly performed on the image to generate a baseline-adjusted vertical Q-mode map. In an implementation, Q-mode map generation circuit 272 may be configured to carry out portions of operation 902 of FIG. 9A, generating at least one Q-mode map from at least one ultrasound video.

Referring again to FIG. 2C, processing circuit 270 may include a B-line detection rule application circuit 274. In an implementation, B-line detection rule application circuit 274 may be configured to apply at least one rule to the generated at least one Q-mode map from at least one ultrasound video to identify one or more B-lines in the at least one ultrasound video, as shown in sub-operation 274A. For example, in an implementation, B-line detection rule application circuit 274 may be configured to carry out portions of operation 904 of FIG. 9A, applying at least one rule to the generated at least one Q-mode map from at least one ultrasound video to identify one or more B-lines in the at least one ultrasound video, which will be discussed in more detail further herein.

Referring now to FIG. 9 and beyond, following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Further, in FIG. 9 and in several of the figures to follow thereafter, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence, except as context dictates otherwise, e.g., where a result of a process step or a circuit output is required for a further process step or as a further circuit input with respect to all other illustrated operations, or may be performed concurrently. Still further, these operations illustrated in FIGS. 9-15, as well as the other operations to be described herein may be performed by at least one of a machine, an article of manufacture, or a composition of matter.

Referring now to FIG. 9A, FIG. 9A shows operation 900, which may include operation 902 depicting generating at least one Q-mode map from at least one ultrasound video. For example, FIG. 2, e.g., FIG. 2C, shows Q-mode map generation circuit 272, which in various implementations may be configured to generate at least one Q-mode map from at least one ultrasound video. Operation 900 may further include operation 904 depicting applying at least one rule to the generated at least one Q-mode map from at least one ultrasound video to identify one or more B-lines in the at least one ultrasound video. For example, FIG. 2, e.g., FIG. 2C, shows B-line detection rule application circuit 274, which in various implementations may be configured to apply at least one rule to the generated at least one Q-mode map from at least one ultrasound video to identify one or more B-lines in the at least one ultrasound video.

Referring now to FIG. 9B, FIG. 9B shows operation 900B, which may include operation 922 depicting preparing, for processing, at least one ultrasound video that includes two or more frames. For example, FIG. 2, e.g., FIG. 2A, shows ultrasound video processing circuit 252, which in various implementations may be configured to prepare, for processing, the at least one ultrasound video that includes two or more frames. The processing preparation may be on a frame-by-frame basis or may target the video as a whole. In an implementation, some frames that are captured by the ultrasound device, e.g., ultrasound device 40, may not ultimately become part of the ultrasound image 70, e.g., if the circuitry for displaying or processing the images and video is expecting a particular number of frames per second. For example, if the ultrasound device 40 captures 180 frames per second of image data, and the connected circuitry is set to receive and process 30 frames per second of image data, then only every sixth frame may become part of the ultrasound image/video 70, and the other five frames are discarded to arrive at a video that is 30 frames per second.

Figure 4A:
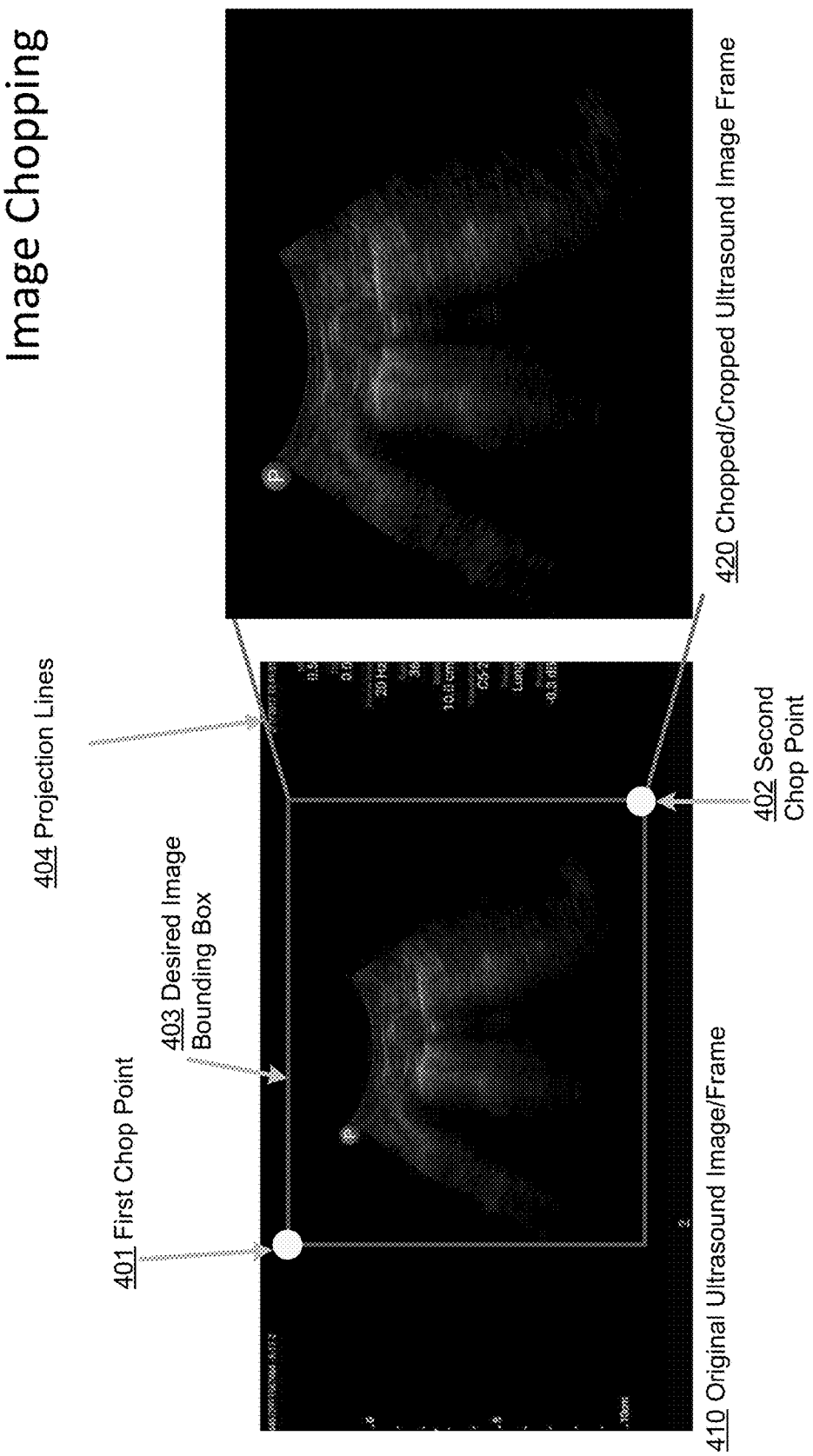
FIG. 4A shows an exemplary illustration of applying a pre-processing cropping or chopping of an image, according to various embodiments of the invention.
Figure 4B:
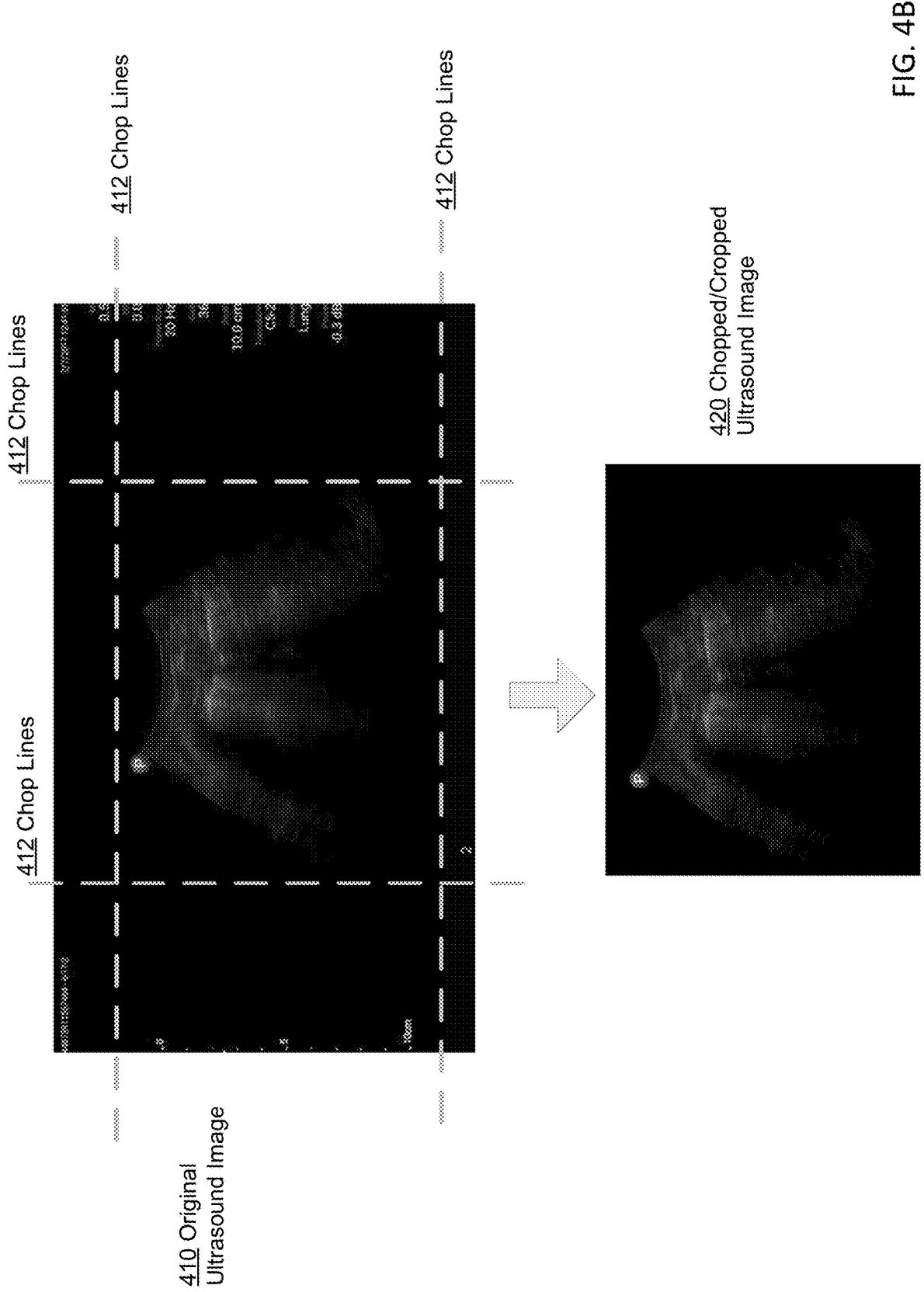
FIG. 4B shows an exemplary illustration of applying a pre-processing cropping or chopping of an image, according to various embodiments of the invention.

In an implementation, in addition to other known pre-processing directives to be applied to the video and images, there are two specific types of image pre-processing that are specifically recited and contemplated here for exemplary purposes. The first is "cutting" or "cropping" of the image to remove excess or unwanted pixels. Some more specific examples of these methods are discussed with respect to FIG. 10A herein. In addition, FIGS. 4A and 4B show various implementations of cutting or cropping the image. Referring to FIG. 4A, then, FIG. 4A shows an original ultrasound image 410, which may be a frame of an ultrasound video, e.g., ultrasound video 70 from FIG. 1A. That is, in an implementation, original ultrasound image 410 represents a single frame from an ultrasound video captured by an ultrasound device, e.g., ultrasound device 40. Referring again to FIG. 4A, original ultrasound image 410 may be manipulated with chop points, e.g., first chop point 401 and second chop point 402. These chop points each may have an x-value and a y-value and thus may define a rectangle between them, e.g., a bounding box. This is shown in FIG. 4A as desired image bounding box 403. In an implementation, pixels within desired image bounding box 403 may be kept, and pixels outside desired image bounding box 403 may be discarded. This is shown through projection lines 404, which show the pixels within desired image bounding box 403 used to form chopped ultrasound image 420. In an implementation, chopped ultrasound image 420 may simply be the pixels that were originally within desired image bounding box 403 of original ultrasound image 410. In another implementation, chopped ultrasound image 420 may be enlarged, e.g., to an original size of original ultrasound image 410, e.g., through various processing techniques, e.g., image interpolation.

Referring now to FIG. 4B, FIG. 4B shows a different manner of converting original ultrasound image 410 into chopped ultrasound image 420. In FIG. 4B, original ultrasound image 410 may be intersected by one or more chop lines 412 that define a bounding box, e.g., similarly to desired image bounding box 403. In FIG. 4B, four chop lines 412 are shown, one for each "side" of original ultrasound image 410, but in other implementations, more or fewer chop lines 412 may be used. In an implementation, original ultrasound image 410 may be cropped at the chop lines 412 to generate chopped ultrasound image 420. In an implementation, chop lines 412 may be set automatically, may be set by an operator (e.g., through viewing original ultrasound image 410 on a portion of device output component 220B, e.g., a monitor, and inputting chop lines 412 into the device 50 via an input device, e.g., a touchscreen monitor, of device input component 220A of device 50), or may be set by some combination thereof. In an implementation, chop lines 412 may be set based on one or more properties of device 50, ultrasound device 40, or probe 42. For example, if a specific type of ultrasound device 40, e.g., a General Electric™ ultrasound device, is used, this ultrasound device may generate an image of a specific size, with lung data in a specific location, and these parameters may be used to select chop lines 412 (the foregoing example is merely exemplary). In another implementation, device 50 may use various image processing techniques, e.g., edge detection, to place chop lines 412. Upon verification of chop lines 412, only those pixels of original ultrasound image 410 that are inside the box formed by chop lines 412 are kept, and other pixels are discarded. As previously described with respect to FIG. 4A, in an implementation, chopped ultrasound image 420 may simply be the pixels that were originally within the box formed by chop lines 412 of original ultrasound image 410. In another implementation, chopped ultrasound image 420 may be enlarged, e.g., to an original size of original ultrasound image 410, e.g., through various processing techniques, e.g., image interpolation.

Figure 4C:
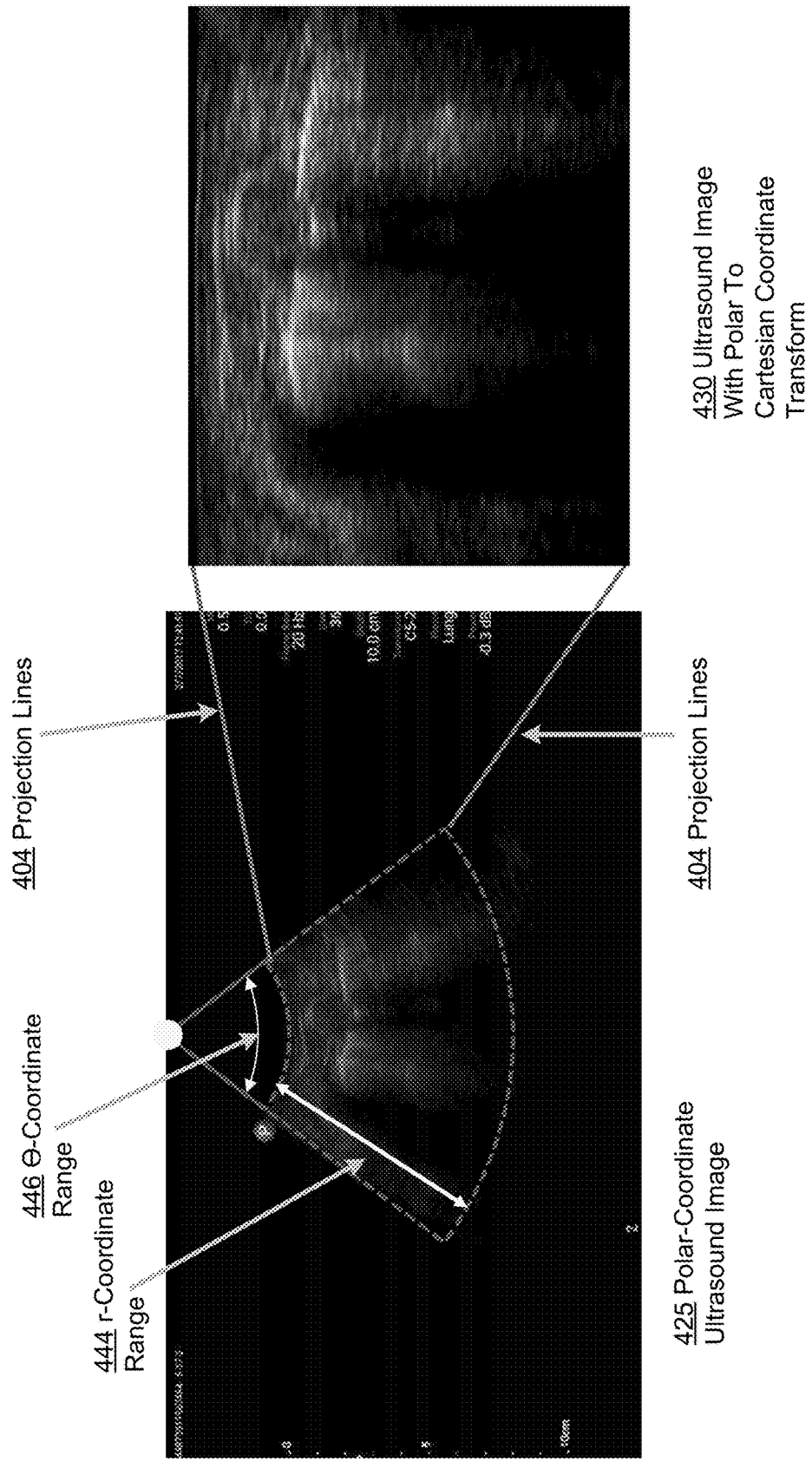
FIG. 4C shows an exemplary illustration of applying a pre-processing coordinate transformation an image that was taken by a phased array or curvilinear transducer and that appears in polar coordinates, according to various embodiments of the invention.

A second type of image pre-processing specifically described herein is a coordinate plane shift. Referring now to FIG. 4C, in an implementation, FIG. 4C shows a polar-coordinate ultrasound image 425, which is a lung ultrasound plotted on a polar coordinate plane (e.g., an (r,θ) coordinate system). In an implementation, polar-coordinate ultrasound image 425 is defined over an r-coordinate 444 and a θ coordinate 446, as shown in FIG. 4C. In an implementation, a coordinate transform is performed to arrive at Cartesian ultrasound image 430, shown in FIG. 4C through projection lines 404 from the edges of polar-coordinate ultrasound image 425 to the opposite edges of Cartesian ultrasound image 430, which has had the polar coordinates (r,θ) transformed to Cartesian coordinates (x,y). In an implementation, this operation may be carried out by re-plotting the pixels to a new coordinate plane, interpolating pixels in portions of the image (e.g., near the top), where pixel data may not be explicitly located, and/or averaging pixels in portions of the image where there is more pixel data than can be plotted (e.g., near the bottom). Any number of known image processing techniques may be used to convert the polar coordinate to the Cartesian coordinates, as well as to fill in any gaps or condense any image data as necessary. As can be seen in the caption to FIG. 4C, the origin point and the depth range may be selected at least partially based on the image depth used to generate the polar-coordinate ultrasound image 425.

Figure 11:
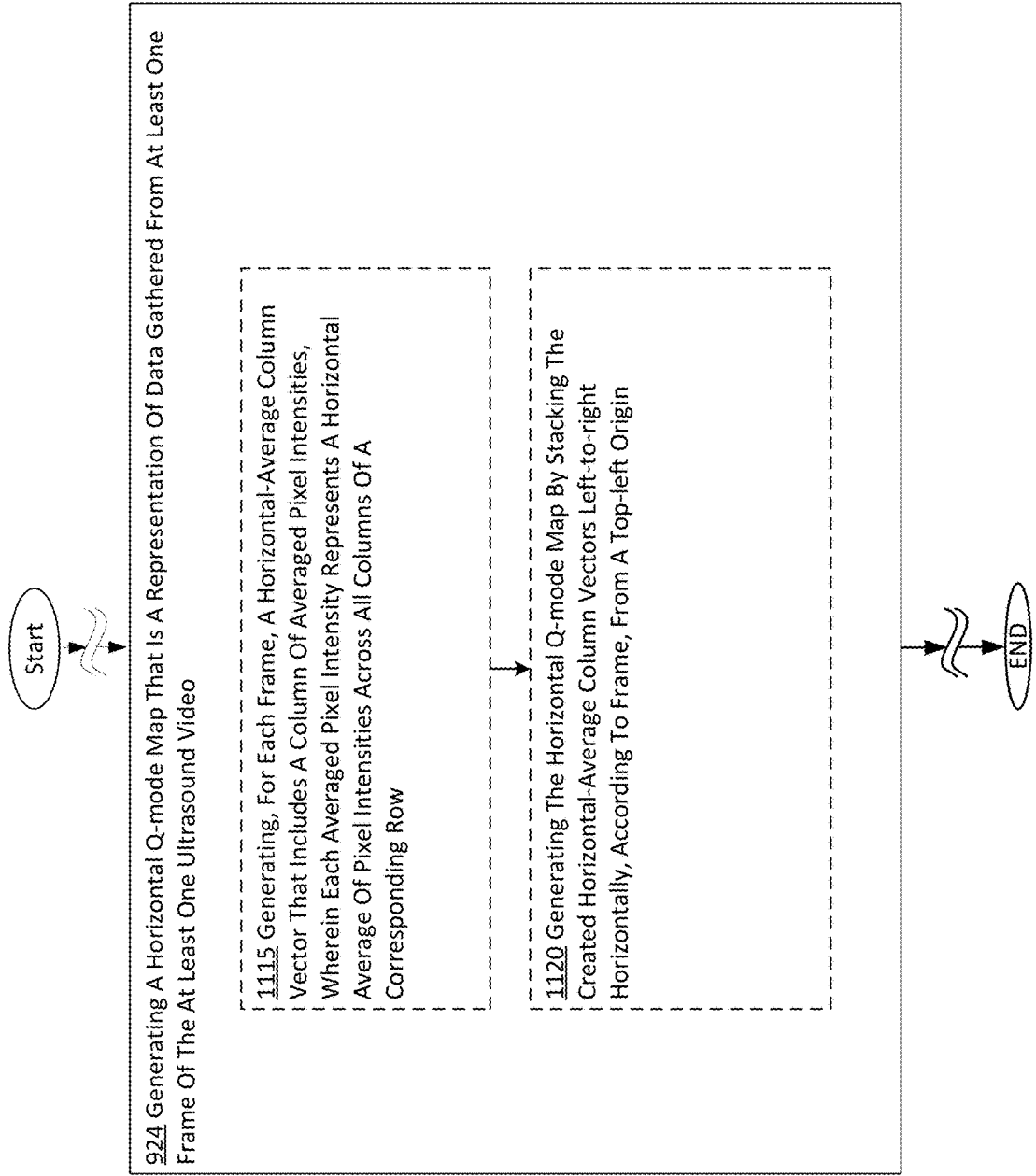
FIG. 11 is a high-level logic flowchart of a generating a horizontal Q-mode map operation 924, according to embodiments of the invention.

Referring again to FIG. 9B, operation 900B may include operation 924 depicting generating a horizontal Q-mode map that is a representation of video data gathered from at least one frame of the at least one ultrasound video. For example, FIG. 2, e.g., FIG. 2A, shows horizontal Q-mode map generation circuit 254, which in various implementations may be configured to generate a horizontal Q-mode map that is at least partly based on the at least one ultrasound video. The horizontal Q-mode map generation is discussed generally with respect to FIG. 3D. In an implementation, the horizontal Q-mode map generation circuit 254 may generate the horizontal Q-mode map through placement of a sequence of horizontal-average column vectors, as previously described. The horizontal-average column vectors may be placed next to each other in ascending (left-to-right) order from a leftmost origin, e.g., starting at the left side of the horizontal Q-mode map. Each horizontal-average column vector may be constructed by calculating, for each row, an average of pixel intensities across columns of that row of the particular frame. That is, for each row of the particular frame, the pixel intensities in that row are averaged, and that average then is placed in the horizontal-average column vector at a location corresponding to the location of the row that was averaged. This implementation is shown in FIG. 11, in which operation 924, e.g., generating a horizontal Q-mode map that is a representation of video data gathered from at least one frame of the at least one ultrasound video, is implemented as operation 1115 depicting generating, for each frame, a horizontal-average column vector that includes a column of averaged pixel intensities, wherein each averaged pixel intensity represents a horizontal average of pixel intensities across all columns of a corresponding row, and operation 1120 depicting generating the horizontal Q-mode map by stacking the created horizontal-average column vectors left-to-right horizontally, according to frame, from a top-left origin.

Another manner of visualizing the construction of the horizontal Q-mode map may be visualizing the construction as individual placement of values at their corresponding locations For example, in an implementation, the horizontal Q-mode map is generated by averaging, for each horizontal row of the frame, a pixel intensity for each pixel in the horizontal row of the frame, and placing, in the horizontal Q-mode map, an averaged pixel at a row indicated by a horizontal row location of the averaged pixels, and at a column indicated by the frame from which the pixels of the horizontal row were averaged, and then repeating that process for each frame of the ultrasound video.

Referring back to FIG. 2E, in an implementation, horizontal Q-mode map generation circuit 254 may include a horizontal-average column vector generation circuit 285 that is configured to create, for each frame, a horizontal-average column vector that includes a column of averaged pixel intensities, wherein each averaged pixel intensity represents a horizontal average of pixel intensities across all columns of a corresponding row, and in various implementations is configured to carry out operation 1115, and horizontal Q-mode map generation circuit 254 configured to carry out operation 1120.

Referring again to FIG. 9B, operation 900B may include operation 926 depicting detecting at least one pleural line through application, to the horizontal Q-mode map, of a pleural line detection rule that defines an appearance of a pleural line in the horizontal Q-mode map. For example, FIG. 2, e.g., FIG. 2A, shows pleural line detection rule application circuit 256, which in various implementations may be configured to detect at least one pleural line (e.g., a line indicating a boundary between a lung and chest cavity wall), through application, to the horizontal Q-mode map, of a pleural line detection rule that defines an appearance of a pleural line in the horizontal Q-mode map. In an implementation, pleural lines run substantially horizontally in ultrasound video images that are mapped to a Cartesian coordinate plane, and thus the horizontal Q-mode map, which due to its formation through horizontal-average column vectors, highlights areas of horizontal lines that persist across more than one frame of the ultrasound video. Thus, in an implementation, horizontal Q-mode map may contain various objects having one or more characteristics indicative of pleural lines, e.g., persistent horizontal lines, roughly in an upper third of the ultrasound video when oriented as described in the previous figures, e.g., FIG. 3D. These objects in the horizontal Q-mode map may indicate where the pleural line or lines are located. In an implementation, the location of the pleural line is used in further processing B-line detection, which may include detecting that the B-line started from a location of the pleural line. Additional rule applications of the pleural line detection will be described in more detail herein with respect to FIG. 12.

Referring again to FIG. 9B, operation 900B may include operation 928 depicting generating at least one vertical Q-mode map that is a representation of data gathered from at least one frame of the at least one ultrasound video. For example, FIG. 2, e.g., FIG. 2A, shows vertical Q-mode map generation circuit 258, which in various implementations may be configured to generate at least one vertical Q-mode map that is a representation of data gathered from at least one frame of the at least one ultrasound video. The vertical Q-mode image generation is discussed generally with respect to FIGS. 3B-3C. In an implementation, the vertical Q-mode map may be generated by stacking vertical-average row vectors, e.g., as illustrated in FIG. 3B, and those vertical-average row vectors may be vertical averages down a subset of rows, e.g., as shown in FIG. 3C. In an implementation, the subset of rows may be selected, at least in part, based on the position of the detected pleural in the previous operation, e.g., operation 926. In an implementation, referring to FIG. 2E, vertical Q-mode map generation circuit 258 may include vertical-average row vector creation circuit 287. The vertical-average row vector creation circuit 287 of FIG. 2E may be configured to create, for each frame, a vertical-average row vector, e.g., vertical-average row vector 365 from FIG. 3B, that includes a row of averaged pixel intensities, wherein each averaged pixel intensity represents a vertical average of pixel intensities along a range of rows of a corresponding column. That is, vertical-average row vector creation circuit 287 may be configured to perform operation 1325 of FIG. 13, which will be discussed in more detail in the next paragraph. Additionally, in an implementation, vertical Q-mode map generation circuit 258 may also include vertical Q-mode map generation circuit 288 of FIG. 2E, which in various implementations may be configured to perform operation 1330 of FIG. 13, e.g., creating the vertical Q-mode map by stacking the created vertical-average row vectors downward vertically, according to frame, from a top-left origin, e.g., as shown in FIGS. 3B and 3C.

Figure 5A:
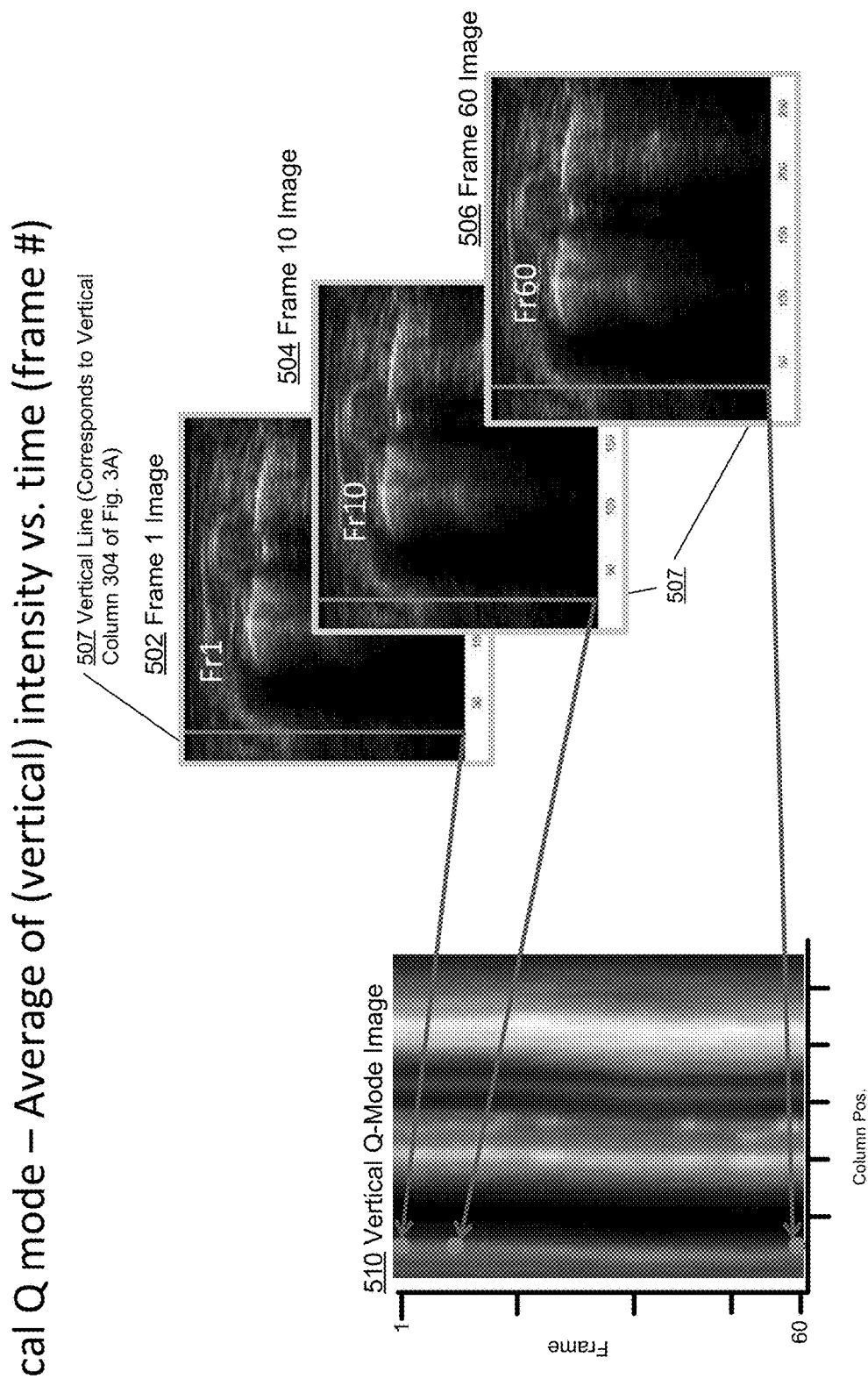
FIG. 5A shows an exemplary illustration of generation of a vertical Q-mode map/image 510, according to various embodiments of the invention.

Referring now to FIG. 5A, FIG. 5A shows an exemplary illustration of how a vertical Q-mode map, e.g., vertical Q-mode image 510, is formed. As mentioned above, although the various Q-mode implementations may be implemented as maps, they also may be implemented as images, as shown in FIG. 5A and some of the following figures. In addition, in FIG. 5A and in some, but not all, of the various other figures, axes appear around the various Q-mode images, e.g., as the axes appear around vertical Q-mode image 510. These axes are not part of the Q-mode image, and are provided for illustration purposes only. These axes are not necessarily to scale or number-accurate, and their inclusion or omission in any drawing should not be assigned a meaning, unless otherwise explicitly stated, or unless context dictates otherwise. As shown in FIG. 5A, a vertical column is signified by the vertical line, e.g., vertical line 507, in image 502 (Frame 1), image 504 (Frame 10), and image 506 (Frame 60). The vertical line 507, which may correspond to the vertical column 304 illustrated in FIG. 3A, represents the vertical column by which the pixels of that column will be averaged, and then placed into a vertical-average row vector corresponding to the frame from which that sum was taken. Individually speaking, the average of the pixel intensities of various vertical lines 507 in FIG. 5A is plotted on vertical Q-mode image 510 at an x-position corresponding to the column number (25) and at a y-position corresponding to the frame (1, 10, and 60, respectively, for image 502, image 504, and image 506). As can be seen by the vertical Q-mode image 510, which is generated and aligned similarly to as described in FIGS. 3B and 3C, persistent vertical lines that appear across multiple frames in the ultrasound image, e.g., potential B-line objects, may appear as lines in substantially the same direction in the vertical Q-mode image 510.

Referring now to FIG. 5B, FIG. 5B shows that various vertical Q-mode images may be generated at various depth ranges, as is specifically illustrated in FIG. 3C. FIG. 5B shows some various exemplary depth ranges for which vertical Q-mode maps and/or images may be generated. For example, varying the depth range of the vertical Q-mode image may be useful, because, as previously described in various implementations, the pleural line, which is substantially horizontal, may effectively create a barrier above which any potential B-line objects that are generated are not true B-lines, but are generated by other objects in the ultrasound video, and will not be further processed. Referring again to FIG. 5B, FIG. 5B shows an ultrasound image 522. One or more vertical Q-mode images may be generated from the video (e.g., the set of frames) to which ultrasound image 522 is associated (only a single frame of the ultrasound video is shown, e.g., ultrasound image 522, for illustration purposes, but the depth range may not change from frame to frame once the depth range has been selected). In an implementation, a vertical Q-mode image, e.g., vertical Q-mode image 514 may be generated from ultrasound image 522, using a first depth range indicated by the large "1" on ultrasound image 522, e.g., depth range 512A. Depth range 512A corresponds to an entire vertical range of ultrasound image 522, and vertical Q-mode image 514 of FIG. 5B may be generated over that entire vertical range. In other words, depth range 512A represents an entire-image depth range, e.g., the entirety of ultrasound image 522 (which may have been previously cropped and converted to Cartesian coordinates as previously described with respect to ultrasound image 520) that is used to generate vertical Q-mode image 514.

Continuing to refer to FIG. 5B, in another implementation, a vertical Q-mode image, e.g., vertical Q-mode image 516 may be generated from ultrasound image 522, using a second depth range indicated by the large "2" on ultrasound image 522, e.g., depth range 512B. Depth range 512B corresponds to a vertical range of ultrasound image 522 that excludes the pleural line and areas above it, e.g., areas in which B-line detection is unlikely or not performed. In yet another implementation, vertical Q-mode image 518 may be generated from ultrasound image 522 using a third depth range indicated by the large "3" on ultrasound image 522 that uses a bottom vertical range. It is noted that each of vertical Q-mode image 514, vertical Q-mode image 516, and vertical Q-mode image 518 are aligned in a similar manner as vertical Q-mode image 510 of FIG. 5A, that is, with the x-axis being the column position and the y-axis being the frame number, e.g., as in FIGS. 3B and 3C.

Referring now to FIG. 5D, FIG. 5D shows how various B-lines in an ultrasound image may appear in a vertical Q-mode map. Although FIG. 5D is provided here as an example, the B-lines in the ultrasound images of FIG. 5D are not very strongly defined, thus making detection more difficult. Specifically, FIG. 5D shows an ultrasound video frame 541 (Frame 23) that includes a transient B-line 542A. As can be seen from FIG. 5D, the transient B-line 542A extends from the pleural line, downward substantially along the scanning beam (because ultrasound video frame 541 is mapped to polar coordinates, not Cartesian, the B-lines, including transient B-lines, are not perfectly vertical). Similarly, ultrasound video frame 542 (Frame 53), shows two additional transient B-lines, transient B-line 542B and transient B-line 542C. These transient B-lines, e.g., 542A, 542B, and 542C, show up as vertical light trails on the vertical Q-mode image 545, as shown in FIG. 5D. Vertical Q-mode image 545 is oriented and aligned similarly to as described in FIGS. 3C and 3E, that is, with a top-left origin, the column position on the x-axis, and the frame number on the y-axis (e.g., so both transient B-line 542B and transient B-line 542C detected in frame 53 have the same y-value, as shown in vertical Q-mode image 545). As shown in FIG. 5D, the vertical Q-mode image 545 allows for the transient B-lines, e.g., transient B-line 542A, transient B-line 542B, and transient B-line 542C, to be detected, and from that detection it can be determined whether they are true B-lines or non-B-line artifacts. In other implementations, transient B-lines may be difficult to detect in the vertical Q-mode map (or detection may result in a high number of false positives), and thus the baseline-adjusted vertical Q-mode map may be generated, which may improve the detection rate and/or the false positive rate.

Referring back to FIG. 9B, operation 900B may include operation 930 depicting detecting one or more potential B-line objects in the at least one vertical Q-mode map. For example, FIG. 2, e.g., FIG. 2A, shows potential B-line object in the vertical Q-mode map detection circuit 260, which in various implementations may be configured to detect one or more potential B-line objects in the at least one vertical Q-mode map. For example, a merged B-line may show up in the ultrasound video as a persistent (e.g. across more than one frame) vertical line. Additionally, merged B-lines are often wider (e.g., span more columns in the ultrasound image and thus appear more frequently in the vertical Q-mode map) than other artifacts detected in the ultrasound image. This vertical line leads to a greater sum in that vertical column, which leads to a greater pixel intensity at that point (vertical column and frame) of the vertical Q-mode map. When that vertical line persists across multiple frames, it appears as a vertical line in an image rendering of the vertical Q-mode map (e.g., the vertical Q-mode image), and such artifacts can be detected as potential B-line objects in the vertical Q-mode map (noting it is not necessary or required to express the vertical Q-mode map as an image—this example mapping used primarily for analogy and illustration). This is shown with respect to FIG. 8A, which shows an ultrasound image 802 that is an image representation of an ultrasound video that contains a merged B-line, e.g., a wide B-line that is wider than many other artifacts of the ultrasound video, persistent across several frames and which may, in some cases, be detectable in the vertical Q-mode image. Because it is not feasible to re-create a video on paper without printing each frame, "ultrasound image 802" will herein be used interchangeably with "ultrasound video 802" and "the video associated with ultrasound image 802," as context dictates.

Referring again to FIG. 9B, operation 900B may include operation 932 depicting applying a baseline adjustment rule to at least one frame of the at least one ultrasound video to generate baseline-adjusted ultrasound video data. For example, FIG. 2, e.g., FIG. 2A, shows baseline adjustment rule application circuit 262, which in various implementations may be configured to carry out operation 932, e.g., application of a baseline adjustment rule to at least one frame of the ultrasound video to generate baseline-adjusted ultrasound video data.

In various implementations, the baseline adjustment rule specifies a baseline number, vector, grid, table, or map, that is a set of pixel intensities, in any format, that is subtracted from the pixel intensities of a frame of the ultrasound video to generate a baseline-adjusted frame. It is noted here that a baseline-adjusted frame does not need to be specifically created, that is, in some implementations, the calculations that would be used to convert a frame into a baseline-adjusted frame are performed, and the results are used in further operations but not stored or assembled into a baseline-adjusted frame. That convention is for sake of illustration and ease of understanding the operations taking place.

The baseline intensity value-subtracted frame is obtained by generating, calculating, receiving, retrieving, or otherwise obtaining, a baseline intensity value for each pixel location. For example, the pixel location (302,202) may have a baseline intensity value of 25 (e.g., on a 0 to 255 grayscale pixel intensity scale). Thus, to convert, e.g., frame 15 into its baseline intensity value-subtracted frame, the value of the pixel intensity of frame 15, pixel (302, 202), will be subtracted by 25 (e.g., if the value is 42 in frame 15, the new value will become 17). The baseline intensity value may be calculated in a number of different ways. For example, in an implementation, the baseline intensity value may be calculated by determining the median pixel intensity for each pixel, as will be discussed in more detail with respect to FIG. 14A.

In an implementation, selecting the baseline image to use for adjusting the various frames of the video is quite important in B-line detection. In one implementation disclosed herein, a median pixel intensity is used as a baseline for each pixel. In other implementations, however, a specific frame may be chosen to serve as the baseline frame, whose pixel intensity values will be subtracted from all other frames' pixel intensity values. For example, if Frame 1 is selected as a baseline frame, then the baseline intensity value for each pixel location will be set to the pixel intensity value of that pixel location within Frame 1. Referring now to FIG. 6D, FIG. 6D shows a baseline-adjusted vertical Q-mode image 612 (from FIG. 6B), which is a vertical Q-mode image of the ultrasound video with Frame 1 values used as baseline pixel intensity values. This is the same baseline-subtracted vertical Q-mode image 612 as seen in FIG. 6B. FIG. 6D then shows, side by side, baseline-adjusted vertical Q-mode image 632, which is the vertical Q-mode image of the same ultrasound video with Frame 25 values used as baseline pixel intensity values and subtracted from the ultrasound video associated with the ultrasound image 602.

Figure 6A:
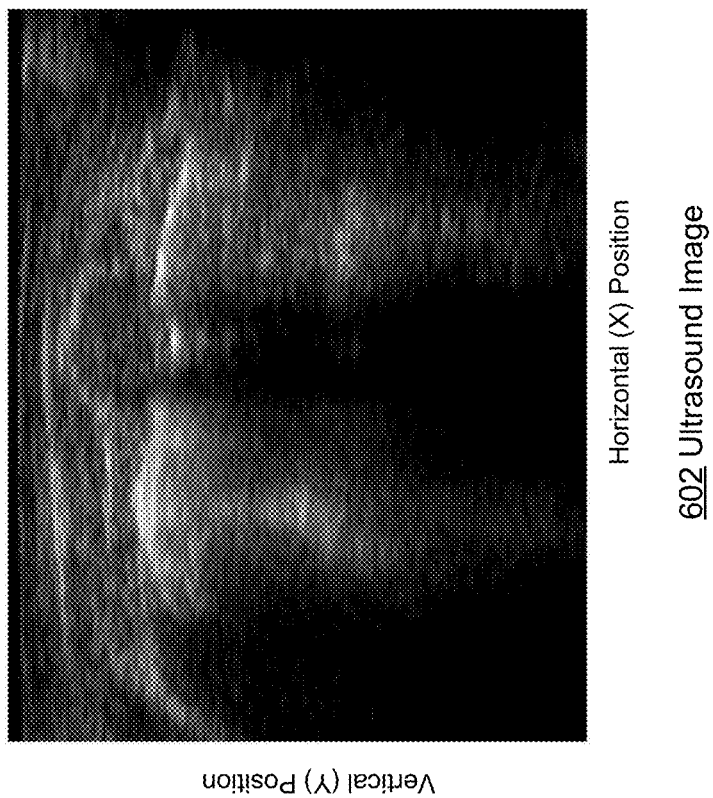
FIG. 6A shows an exemplary illustration of an ultrasound image 602, in Cartesian coordinates, according to various embodiments of the invention.
Figure 7A:
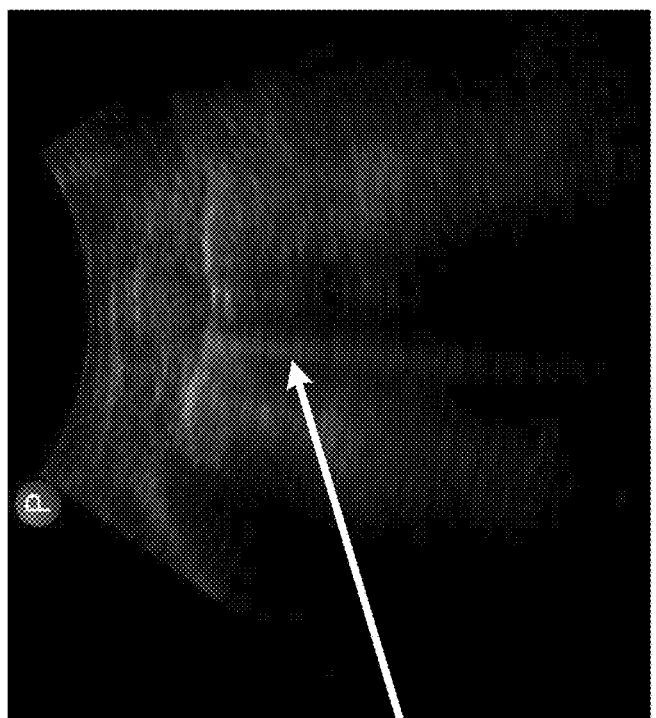
FIG. 7A shows an exemplary illustration of an ultrasound image 702, including at least one B-line, according to various embodiments of the invention.

Referring also to FIG. 7B, it is demonstrated that the selection of the specific frame to serve as the baseline frame may have an effect on the resultant baseline-adjusted vertical Q-mode image as contrasted with selecting a median pixel value used as a baseline. For example, in an implementation, one or more frames of the ultrasound video, e.g., ultrasound video based on ultrasound image 702 of FIG. 7A, (which shows an ultrasound image 702 that has a B-line 704 present in the image), may be selected as a baseline set of values. The baseline-adjusted vertical Q-mode image 712 represents a vertical Q-mode image that is generated based on a set of frames from the video associated with ultrasound image 702, and that that have been adjusted by subtracting pixel intensities of baseline frame 25. This baseline-adjusted vertical Q-mode image 712 is placed side by side with baseline-adjusted vertical Q-mode image 714, which uses the median pixel value for each pixel location as a baseline. As can be seen in the side by side images of FIGS. 6D and 7B, respectively, the selection of a particular frame to be used as a baseline, as well as the use of a median pixel intensity value instead of a specific frame's pixel intensity value can have dramatic effects on the resulting baseline-adjusted vertical Q-mode image.

Accordingly, in various implementations, a median value of pixel intensities at a particular location across all frames is calculated, and used as a baseline value. In other implementations, a median value of pixel intensities at a particular location across a subset of frames is calculated, for example, with certain frames dropped (e.g., to make a non-contiguous set), or with the first ten frames at the beginning and/or at the end dropped from the set. In other implementations, outlier frames may be identified with various algorithms (e.g., total intensity far out of line with expected value), and discarded from the set from which median value of pixel intensities at particular pixel locations will be calculated.

Figure 14A:
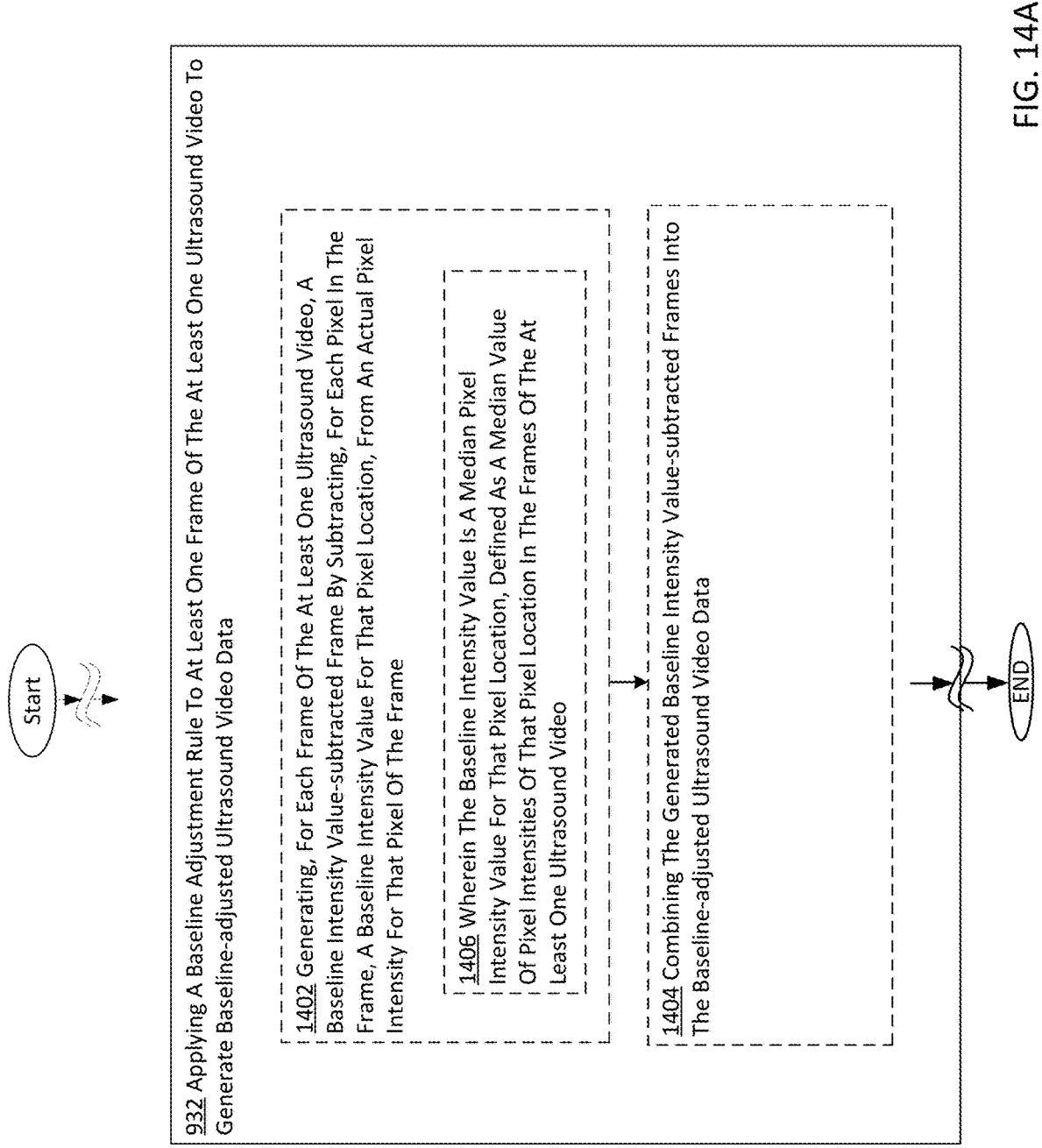
FIG. 14A is a high-level logic flowchart of an applying a baseline adjustment rule operation 932, according to embodiments of the invention.

Referring now to FIG. 14A, FIG. 14A shows various implementations of operation 932 depicting applying a baseline adjustment rule to at least one frame of the at least one ultrasound video to generate baseline-adjusted ultrasound video data. For example, in an implementation, operation 932 may include operation 1402 depicting generating, for each frame of the at least one ultrasound video, a baseline intensity value-subtracted frame by subtracting, for each pixel in the frame, a baseline intensity value for that pixel location, from an actual pixel intensity for that pixel of the frame. As described above, the baseline intensity value may be subtracted from the actual pixel intensity value for each pixel of the frame, e.g., as shown in FIG. 3E. In an implementation, operation 932 also may include operation 1404 depicting combining the generated baseline intensity value-subtracted frames into the baseline-adjusted ultrasound video data that is, generating the baseline-adjusted ultrasound video data that is a combination of all of the generated baseline intensity-value subtracted frames, while noting that the frames may not all be calculated at the same time (e.g., a frame may be calculated, used to generate the baseline-adjusted vertical Q-mode map data for that frame, and then discarded or overwritten by a new frame's data), and may not ever be stored as, used, or otherwise converted or utilized as "video data." The term is used here merely for convenience and ease of explanation.

Referring again to FIG. 14A, operation 1404 may be modified so that the baseline intensity value is a median pixel intensity value, e.g., as shown in operation 1406 of FIG. 14A. That is, rather than selecting a single frame from which to draw the baseline intensity values, a median pixel intensity, based upon a median, e.g., a quantity lying at the midpoint of a frequency distribution of observed values or quantities, e.g., a $50^{th}$ percentile value, e.g., a middle value when stacked in ascending or descending order, of all the pixel intensities of a specific pixel location across all or a set of the frames in the ultrasound video, is generated. This median pixel intensity is then used as the baseline value to be subtracted out from each frame of the ultrasound video. Such a technique may be useful when detecting B-lines, because unlike some other artifacts shown in ultrasounds of the lung, B-lines are not persistent for an extended period of time (for example A-lines, which are persistent in contrast to most B-lines, as previously discussed) relative to the entire ultrasound video. Thus, subtracting a median pixel intensity from each frame allows to reduce artifacts that are persistent throughout the entire video, e.g., that are unlikely to be B-line artifacts. This is particularly true in the case of detecting transient B-lines, or B-lines that would be otherwise difficult to detect. By subtracting the median pixel intensity from each frame, artifacts that would otherwise be detected as potential B-line objects, but which are in truth false positives generated by other artifacts in the ultrasound video, are less likely to be detected, which may reduce the rate at which false positives are detected, and further may allow the threshold levels to be lowered and the sensitivity to be increased (e.g., the thresholding and choosing of a threshold level will be discussed in more detail herein).

Referring again to FIG. 9B, in an implementation, operation 900B may include operation 934 depicting generating at least one baseline-adjusted vertical Q-mode map, at least partly based on the baseline-adjusted ultrasound video data. For example, FIG. 2, e.g., FIG. 2A, shows baseline-adjusted vertical Q-mode map generation circuit 264, which in various implementations may be configured to carry out operation 934. That is, from the baseline-adjusted ultrasound video data generated in the previous operation, a baseline-adjusted vertical Q-mode map, e.g., baseline-adjusted vertical Q-mode map 350 of FIG. 3E, may be generated. It is noted that operation 934 may happen in parallel with operation 932, that is, as the baseline-adjusted ultrasound video data is generated, it may be used to generate portions of the baseline-adjusted vertical Q-mode map, so that a complete set of baseline-adjusted ultrasound video data may not ever be generated in some embodiments, but may be cycled and overwritten as the baseline-adjusted vertical Q-mode map is generated. In an implementation in which baseline-adjusted frames are generated for which a baseline intensity has been subtracted (e.g., a baseline intensity value-subtracted frame), the baseline-adjusted vertical Q-mode map may be at least partly based on each baseline intensity value-subtracted frame. In this instance, the baseline-adjusted vertical Q-mode map is generated in substantially the same manner as the vertical Q-mode image, except that the baseline-adjusted vertical Q-mode map relies on the baseline intensity value-subtracted frames rather than on merely the frames of the ultrasound video. Thus, in an implementation, the baseline-adjusted vertical Q-mode map is generated through placement of a sequence of baseline-adjusted vertical-average row vectors, e.g., vertical-average row vector 385 from FIG. 3E, as modified with a baseline adjustment.

As an example of a baseline-adjusted vertical Q-mode map, reference now is made to FIG. 7B, which shows a vertical Q-mode image 712 of the video associated with ultrasound image 702. Vertical Q-mode image 712 has been adjusted by subtracting the pixel intensities found at frame 25, from every frame in the image. In contrast, FIG. 7B also shows vertical Q-mode image 714, which follows operation 1402, 1404, and 1406, in that, for each frame of the at least one ultrasound video that is associated with ultrasound image 702, a baseline-subtracted frame is generated by subtracting the median pixel intensity value from the pixel intensity for that pixel of the frame. Thus, vertical Q-mode image 714 is a vertical Q-mode image of that adjusted ultrasound video frame data, in which the median pixel intensity value has been subtracted from every frame in the video, generating a different vertical Q-mode image, e.g., baseline-adjusted vertical Q-mode image 714, which, in some implementations, has fewer artifacts and/or candidates that may trigger a false positive, and also which may have better performance in detecting true positives, in some implementations.

Figure 14B:
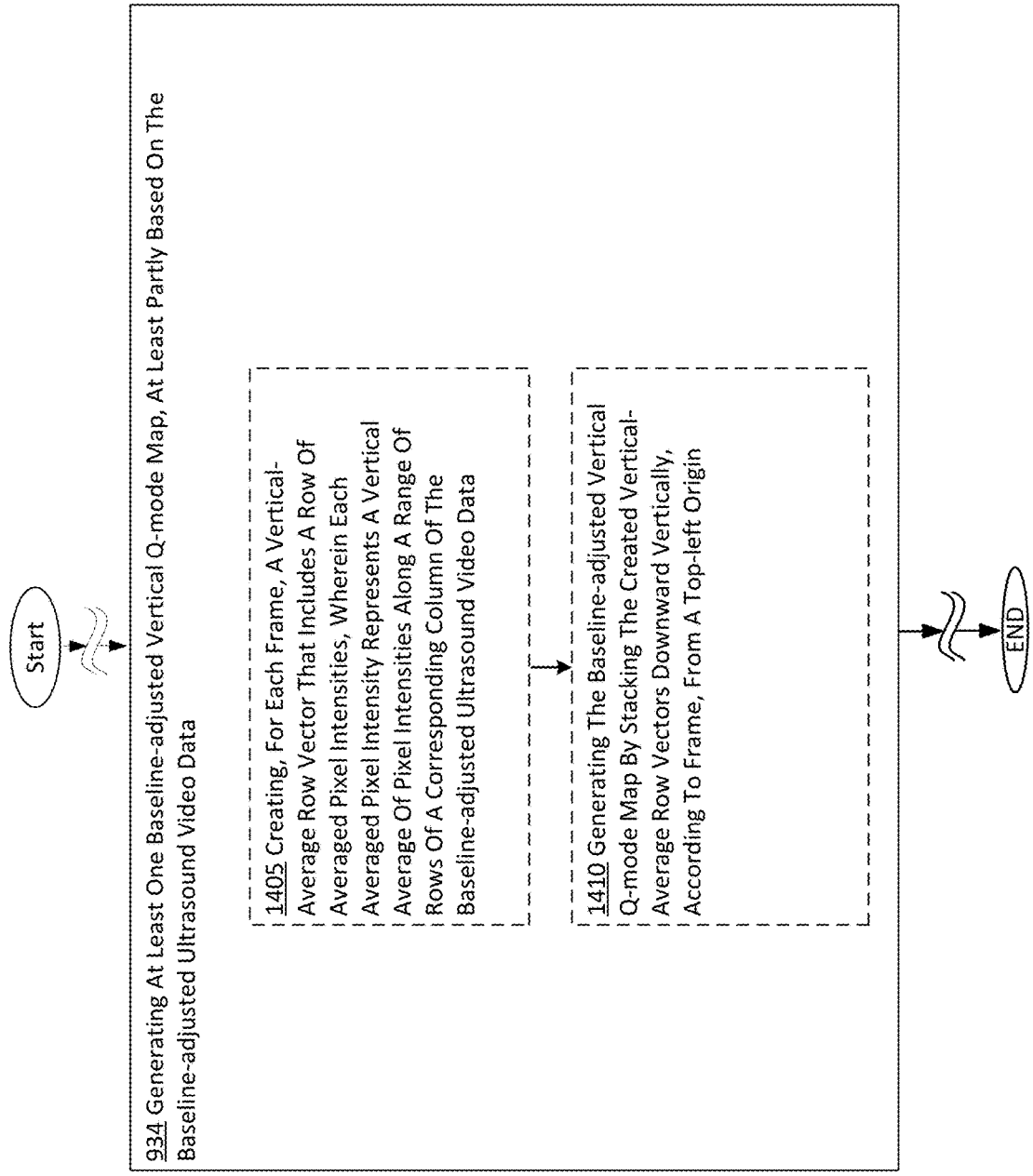
FIG. 14B is a high-level logic flowchart of a generating at least one baseline-adjusted vertical Q-mode map operation 934, according to embodiments of the invention.

These baseline-adjusted vertical-average row vectors may be placed below one another in descending order (e.g., downward, although the frame number will be increasing because the origin is at the top-left). As has been previously described, each baseline-adjusted vertical-average row vector may be constructed by calculating, for each column, an average of pixel intensities down a range of rows for the column of the frame that is associated with that specific baseline-adjusted vertical-average row vector. Similarly to the vertical Q-mode map, the baseline-adjusted vertical Q-mode map may be generated with an average over only a range of rows (which may include all rows), for the same reasons that have been previously described with respect to the vertical Q-mode map. For each column of the particular frame, a subset of the pixel intensity values in that column will be averaged, and then that average is placed in the baseline-adjusted vertical-average row vector at a location corresponding to the location of the column that was averaged. This implementation is shown in FIG. 14B, which shows an implementation of operation 932, e.g., applying a baseline adjustment rule to at least one frame of the at least one ultrasound video to generate baseline-adjusted ultrasound video data, as operation 1405 depicting creating, for each frame, a vertical-average row vector that includes a row of averaged pixel intensities, wherein each averaged pixel intensity represents a vertical average of pixel intensities along a range of rows of a corresponding column of the baseline-adjusted ultrasound video data, and operation 1410 depicting generating the baseline-adjusted vertical Q-mode map by stacking the created vertical-average row vectors downward vertically, according to frame, from a top-left origin.

Referring now to FIG. 5C, FIG. 5C shows various baseline-adjusted vertical Q-mode maps and baseline-adjusted horizontal Q-mode images (which may be used in various alternate implementations for detection and/or confirmation, and/or reducing false positives). For example, FIG. 5C shows a vertical Q-mode image 531A. Vertical Q-mode image 531A is aligned similarly to other vertical Q-mode images in previous figures, e.g., with the column position on the x-axis, and the frame number on the y-axis, with an origin at the top-left. In an implementation, vertical Q-mode image 531A represents a vertical Q-mode image taken from an ultrasound video at a particular depth level. FIG. 5C also shows rib areas 532A of vertical Q-mode image 531A that are shown for effect. In FIG. 5C, a baseline-adjusted vertical Q-mode image 531B is shown side by side with vertical Q-mode image 531A for comparison. Specifically, baseline-adjusted vertical Q-mode image 531B is a vertical Q-mode image that is based on baseline-adjusted frames, e.g., it is an image in which pixel intensity values from Frame 1 were used as baseline pixel intensity values, and subtracted from the frames of the ultrasound video, and the subtracted frames were used to generate baseline-adjusted vertical Q-mode image 531B. In FIG. 5C, baseline-adjusted vertical Q-mode image 531B also appears side by side with baseline-adjusted vertical Q-mode image 532 for comparison. Specifically, baseline-adjusted vertical Q-mode image 532 is a vertical Q-mode image generated similarly to vertical Q-mode image 531B, except by using Frame 25 for the baseline pixel intensity values to generate vertical Q-mode image 532.

Referring again to FIG. 5C, FIG. 5C also shows a horizontal Q-mode image 533A. Horizontal Q-mode image 533A is aligned similarly to other horizontal Q-mode images in previous figures, e.g., with the frame number on the x-axis, and the row position on the y-axis, with the origin at the top-left. In FIG. 5C, horizontal Q-mode image 533A is shown with pleural line 534A for effect. Additionally, horizontal Q-mode image 533A is compared side by side with baseline-adjusted horizontal Q-mode image 533B. Specifically, baseline-adjusted horizontal Q-mode image 533B is a horizontal Q-mode image that is based on baseline-adjusted frames, e.g., it is an image in which frame 1 pixel intensity values were used as baseline pixel intensity values, and subtracted from the frames of the ultrasound video, and the subtracted frames were used to generate baseline-adjusted horizontal Q-mode image 533B.

Referring now to FIG. 6, e.g., FIG. 6A, an exemplary ultrasound image 602 that is a frame of an ultrasound video is shown. Referring to FIG. 6B, FIG. 6B shows vertical Q-mode image 610, which is a vertical Q-mode image of the ultrasound video associated with ultrasound image 602 (e.g., the single-frame image 602 is used since videos cannot easily be displayed on paper, but for the various figures included in FIG. 6, and everywhere else dictated by context, it can be assumed that "ultrasound image 602" can be replaced with "the video associated with ultrasound image 602" as context dictates). Vertical Q-mode image 610 is aligned similarly to other vertical Q-mode images in previous figures, e.g., with the column position on the x-axis, and the frame number on the y-axis, with an origin at the top-left. In an implementation, vertical Q-mode image 610 includes various patterns of very dark areas, marked in the vertical Q-mode image 610 as rib areas 617. These rib areas 617 of vertical Q-mode image 610 represent rib shadows present in the ultrasound image 602. As described above, rib shadows occur when the ultrasound signal is reflected by a rib of the rib cage, rather than penetrating through to the lung.

As shown in FIG. 6B, vertical Q-mode image 610 is shown next to baseline-adjusted vertical Q-mode image 612, in which frame 1 values were used as the baseline pixel intensities. Specifically, if reference is made back to the example shown in FIG. 3E, the pixel intensities of Frame 1 of ultrasound image 602 would be used as baseline adjustment value table 355. That is, the pixel intensities of Frame 1 are as subtracted from the pixel intensities of the various frames of the video associated with ultrasound image 602. These "new" frames then form the basis for baseline-adjusted vertical Q-mode image 612, which is generated as a vertical Q-mode image, as previously described, from the baseline-subtracted frames.

Referring again to FIG. 6B, FIG. 6B also shows horizontal Q-mode image 620, which is a horizontal Q-mode image of the ultrasound video associated with ultrasound image 602. Horizontal Q-mode image 620 is aligned similarly to other horizontal Q-mode images in previous figures, e.g., with the origin at the top-left (e.g., which causes the pleural line to appear in the top half of the Q-mode image), the frame number on the x-axis, and the row position on the y-axis. Additionally, horizontal Q-mode image 620 shows pleural line 619, for a reference/orientation point. As shown in FIG. 6B, horizontal Q-mode image 620 is placed side by side with baseline-adjusted horizontal Q-mode image 622, in which pixel intensity values from Frame 1 were used as the baseline pixel intensities, subtracted from the various frames of the video associated with ultrasound image 602, and the baseline-adjusted horizontal Q-mode image 622 was generated from the baseline-subtracted frames.

Referring back to FIG. 9B, operation 900B may include operation 936 depicting detecting one or more potential B-line objects in the baseline-adjusted vertical Q-mode map. For example, FIG. 2, e.g., FIG. 2A, shows potential B-line object in an adjusted Q-mode map detection circuit 266, which in various implementations may be configured to detect potential B-line objects in the baseline-adjusted vertical Q-mode map generated in operation 936. For example, a transient or merged B-line may show up in the ultrasound video as a persistent (e.g. across more than one frame) vertical line. This vertical line leads to a greater sum in that vertical column, which leads to a greater pixel intensity at that point (vertical column and frame) of the baseline-adjusted vertical Q-mode map. When that vertical line persists across multiple frames, it appears as a vertical line in an image rendering of the baseline-adjusted vertical Q-mode map (e.g., the baseline-adjusted vertical Q-mode image), and such artifacts can be detected as potential B-line objects in the vertical Q-mode map (noting it is not necessary or required to express the vertical Q-mode map as an image—this example mapping used primarily for analogy and illustration). This effect may be amplified for transient B-lines that appear only briefly, because the pixel locations in frames in which they appear will be adjusted by a lower value (in implementations in which a median pixel value is used), relative to pixel locations where the artifacts appear throughout the entire image, in which the median pixel value will be higher and thus those pixel intensities will be adjusted downward by a larger value.

Figure 8B:
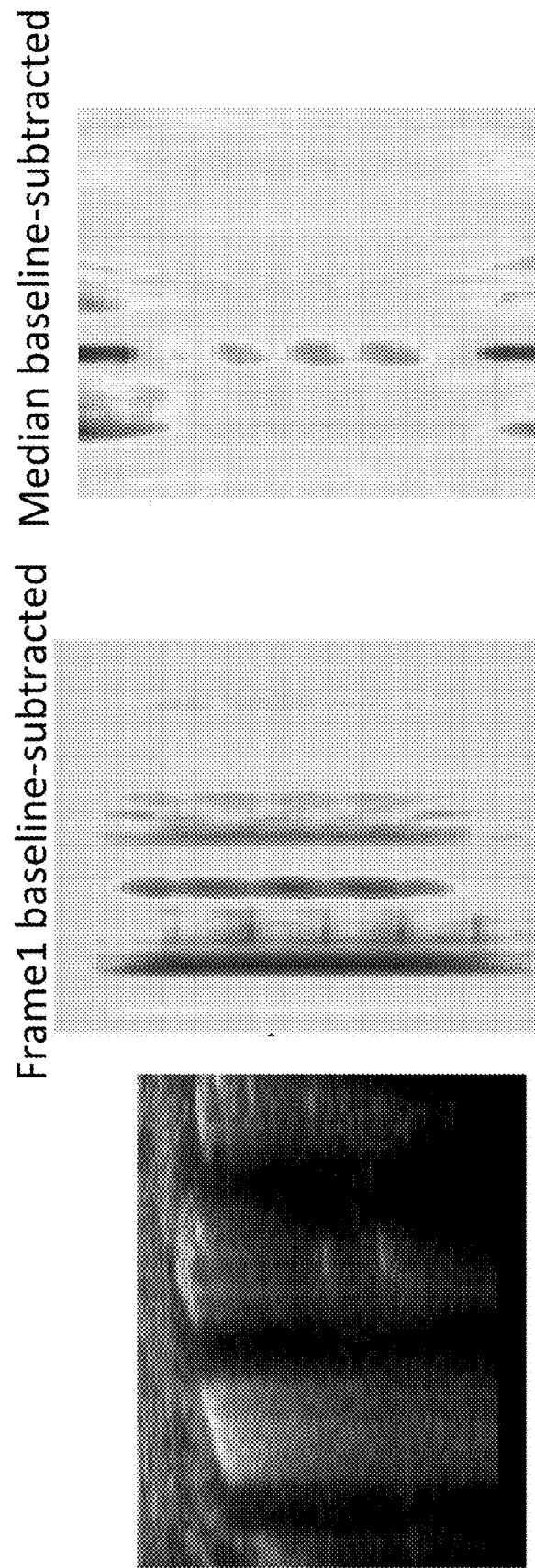
FIG. 8B shows an exemplary illustration of various ultrasound video images, Q-mode maps/images and modified Q-mode maps/images, according to various embodiments of the invention.

An exemplary baseline-adjusted vertical Q-mode map and its relationship to an exemplary vertical Q-mode map can be seen in FIGS. 8A and 8B. As previously described, FIG. 8A shows a Frame 14 of ultrasound video 802, and the vertical Q-mode map generated therefrom (e.g., vertical Q-mode image 810, with the merged B-line visible. Referring now to FIG. 8B, which also shows frame 804 (e.g., Frame 14 of ultrasound video 802), FIG. 8B shows the baseline-adjusted vertical Q-mode map 822. Baseline-adjusted vertical Q-mode map 822 is generated from a baseline-adjusted video that used pixel intensity values of Frame 1 of ultrasound video 802 as baseline values throughout the ultrasound video 802. Baseline-adjusted vertical Q-mode map 822 may be compared to vertical Q-mode map 810 of FIG. 8A, or, may be compared side-by side with baseline-adjusted vertical Q-mode map 824, which is a baseline-adjusted vertical Q-mode map that uses the median pixel intensities for each pixel location as a baseline. As can be seen from the side-by-side images in FIG. 8B, changing the baseline in the video-based B-line detection process also causes substantially varying results, which may have the effect of improving potential B-line object detection.

Figure 15A:
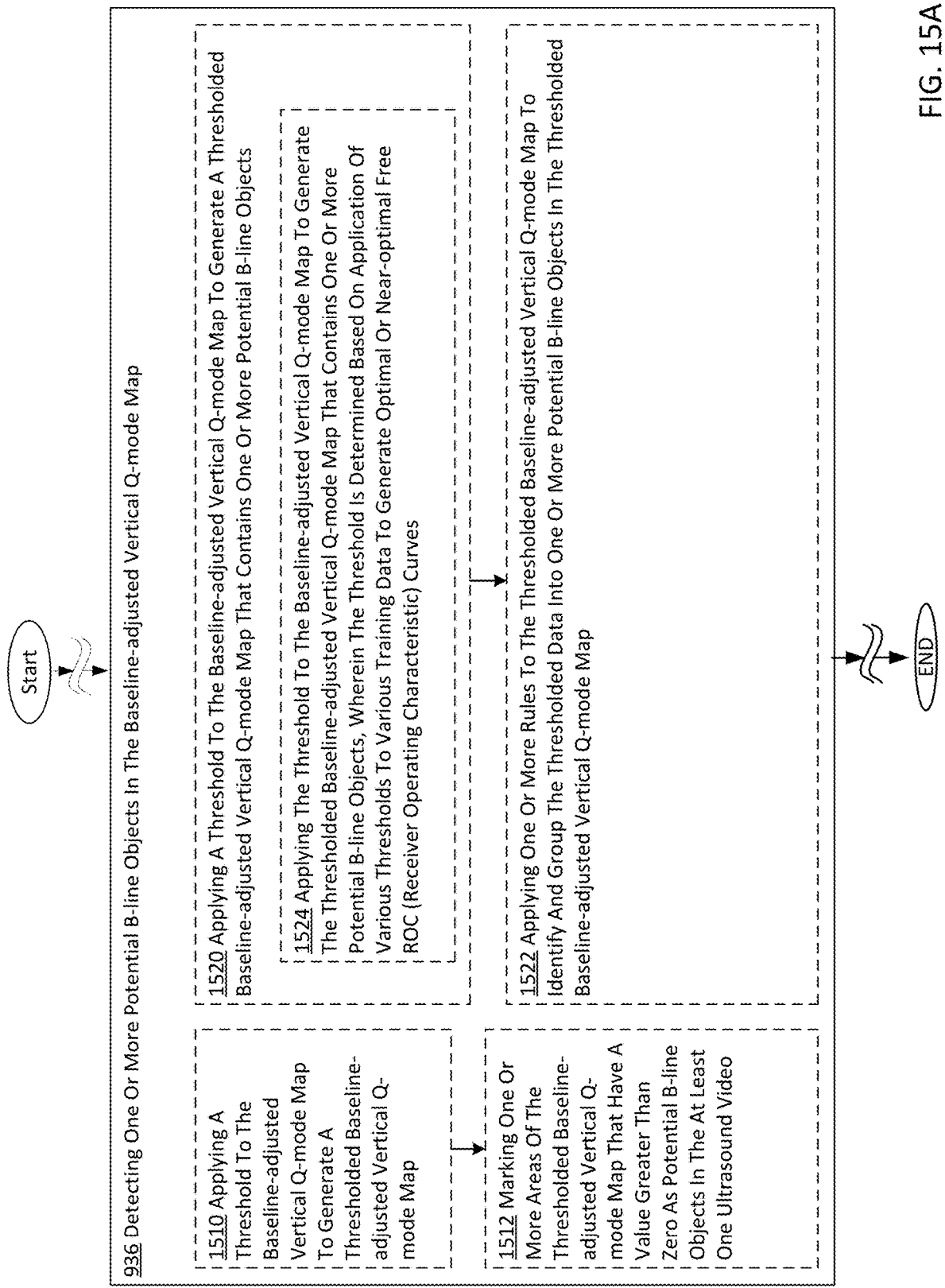
FIG. 15A is a high-level logic flowchart of an detecting one or more potential B-line object operation 936, according to embodiments of the invention.
Figure 16:
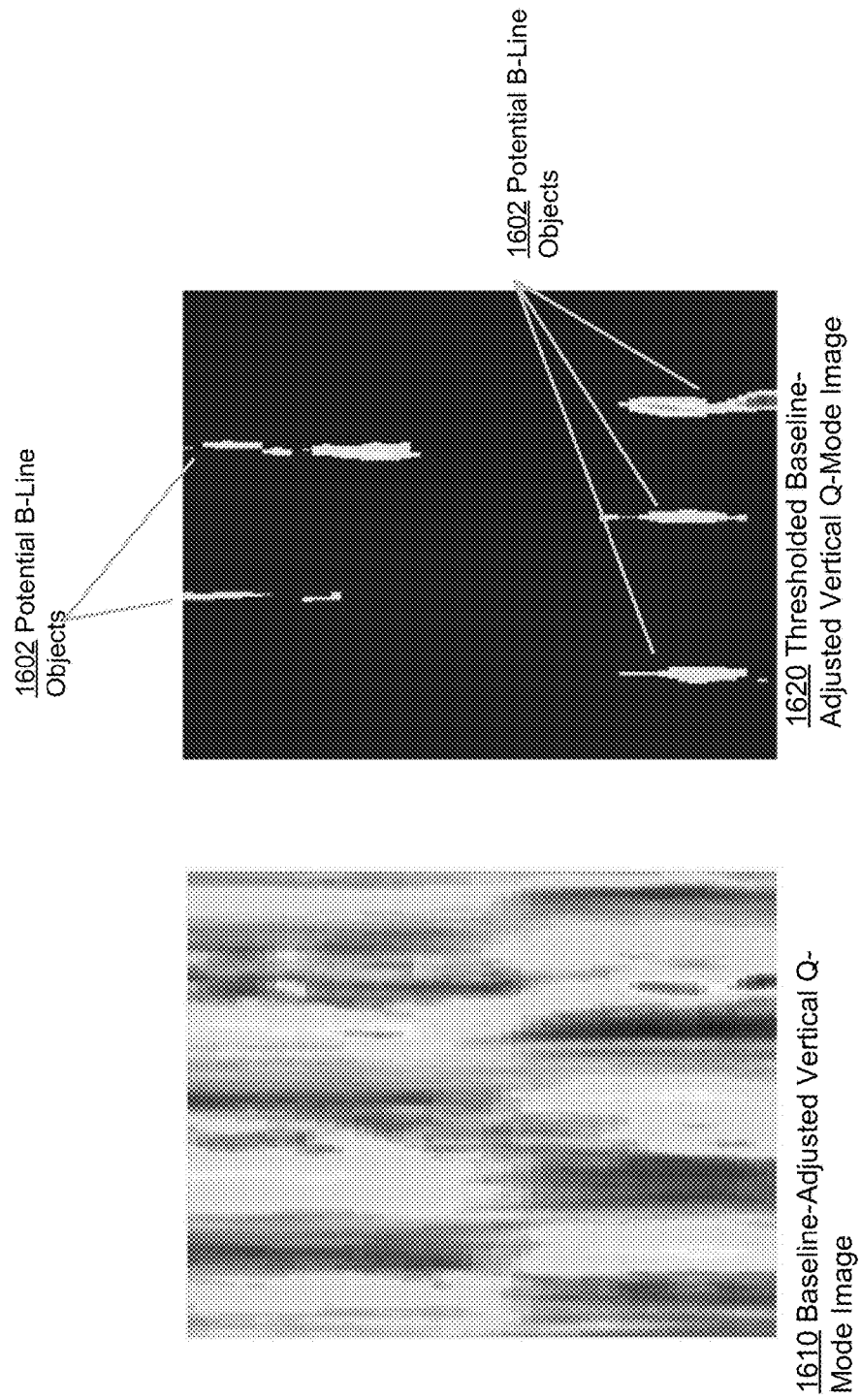
FIG. 16 shows an exemplary illustration of a baseline-adjusted vertical Q-mode image and a thresholded baseline-adjusted Q-mode image, according to various embodiments of the invention.

Referring now to FIG. 15A, FIG. 15A shows various implementations of operation 936 of depicting detecting one or more potential B-line objects in the baseline-adjusted vertical Q-mode map, e.g., specifically with respect to thresholding. It is noted that all of the operations described in FIG. 15A with respect to the baseline-adjusted vertical Q-mode map also may apply to the original vertical Q-mode map, in various implementations. For example, in an implementation, operation 934 may include operation 1510 depicting applying a threshold to the baseline-adjusted vertical Q-mode map to generate a thresholded baseline-adjusted vertical Q-mode map. For example, various threshold values may be applied to the baseline-adjusted vertical Q-mode image, as is illustrated in various figures throughout the application. In another implementation, e.g., referring to FIG. 6C, FIG. 6C shows various effects of different threshold values. For example, in FIG. 6C, a vertical Q-mode image, e.g., vertical Q-mode image 610 (from FIG. 6B) is selected, and then baseline-adjusted using frame 25 values of pixel intensity, from which a frame-25 baseline-adjusted vertical Q-mode image was generated. This frame-25 baseline-adjusted vertical Q-mode image was then thresholded at 0-value to generate thresholded vertical Q-mode image 642. Similarly, this frame-25 baseline-adjusted vertical Q-mode image was thresholded at 2-value to generate thresholded vertical Q-mode image 644. In yet another implementation, the frame-25 baseline-adjusted vertical Q-mode image was then thresholded at 4-value to generate thresholded vertical Q-mode image 646, as can be seen in FIG. 6C. Referring now to FIG. 16, in an implementation, FIG. 16 shows an example of a threshold being applied to a baseline-adjusted vertical Q-mode image. For example, FIG. 16 shows baseline-adjusted vertical Q-mode image 1610. In an implementation, application of a threshold or a thresholding rule to baseline-adjusted vertical Q-mode image 1610 may generate a thresholded image, e.g., thresholded baseline-adjusted vertical Q-mode image 1620. In an implementation, thresholded baseline-adjusted vertical Q-mode image 1620 may have different gradations of thresholding, e.g., represented by the different colors or shades shown in thresholded baseline-adjusted vertical Q-mode image 1620; in other implementations, the thresholding may be binary or otherwise graded.

Referring again to FIG. 15A, in implementations in which operation 936 includes operation 1510, operation 936 also may include operation 1512 depicting marking one or more areas of the thresholded vertical Q-mode map that have a value greater than zero as potential B-line objects in the at least one ultrasound video. For example, in an implementation, the thresholded baseline-adjusted vertical Q-mode image may have one or more B-line detection rules for which candidates for B-lines, e.g., potential B-line objects 1602 of FIG. 16, may be processed and used to determine which portions of the ultrasound video should be extracted or "sliced" based on the detection of the potential B-line objects 1602. In various implementations, these determinations may be based on distance tolerance calculations, or may involve finding midpoints of clusters of potential B-line objects.

For example, as shown in FIG. 16, FIG. 16 shows one application of one or more B-line detection rules as applied to a thresholded vs. non-thresholded image. For example, in an implementation, FIG. 16 shows a baseline-adjusted vertical Q-mode image 1610, in which one or more of the previously described steps have been applied. FIG. 16 also shows a thresholded baseline-adjusted vertical Q-mode image 1620, which has had a threshold applied to the image. In the example shown in FIG. 16, the threshold value used was 5, but other threshold values may be chosen through any number of machine-based or human-assisted techniques. In an implementation, the thresholding of baseline-adjusted vertical Q-mode image 1610 into thresholded baseline-adjusted vertical Q-mode image 1620 generates one or more potential B-line objects 1602. In an implementation, various techniques are used to determine which of potential B-line objects 1602 should be clustered together, and in various implementations, no clustering is performed (e.g., each potential B-line object is treated as a separate potential B-line).

Referring again to FIG. 15A, in an implementation, operation 936 may include operation 1520 depicting applying a threshold to the baseline-adjusted vertical Q-mode map to generate a thresholded baseline-adjusted vertical Q-mode map that contains one or more potential B-line objects, which is similar to the operation previously described in operation 1510 of FIG. 15A. For example, various threshold values may be applied to the baseline-adjusted vertical Q-mode image, as is illustrated in various figures throughout the application. In an implementation, e.g., referring to FIG. 6C, FIG. 6C shows various effects of different threshold values. For example, in FIG. 6C, a vertical Q-mode image, e.g., vertical Q-mode image 602 (from FIG. 6A) is selected, and then baseline-adjusted using frame 25 values of pixel intensity, from which a frame-25 baseline-adjusted vertical Q-mode image was generated. This frame-25 baseline-adjusted vertical Q-mode image was then thresholded at 0-value to generate thresholded vertical Q-mode image 642. Similarly, this frame-25 baseline-adjusted vertical Q-mode image was thresholded at 2-value to generate thresholded vertical Q-mode image 644. In yet another implementation, the frame-25 baseline-adjusted vertical Q-mode image was then thresholded at 4-value to generate thresholded vertical Q-mode image 646, as can be seen in FIG. 6C.

Referring again to FIG. 15A, operation 1520 may include operation 1524 depicting applying the threshold to the baseline-adjusted vertical Q-mode map to generate the thresholded baseline-adjusted vertical Q-mode map that contains one or more potential B-line objects, wherein the threshold is determined based on application of various thresholds to various training data to determine optimal or near-optimal free ROC (receiver operating characteristic) ("fROC") curves. For example, in an implementation, the threshold value may vary depending on a result of various training data that yields various receiver operating characteristic (ROC) curves or free ROC curves, depending on the desired sensitivity, and/or an acceptable false positive rate.

Referring again to FIG. 15A, in implementations in which operation 936 includes operation 1520, operation 936 also may include operation 1522 depicting applying one or more rules to the thresholded baseline-adjusted vertical Q-mode map to identify and group the thresholded data into one or more potential B-line objects in the thresholded baseline-adjusted vertical Q-mode map. For example, in an implementation, the thresholded baseline-adjusted vertical Q-mode image may have one or more rules for which candidates for B-lines, e.g., potential B-line objects 1602 of FIG. 16, may be grouped and determined for extraction from the ultrasound video data to determine whether they represent B-lines.

Referring back to FIG. 9B, operation 900B may conclude with operation 938 depicting applying one or more B-line detection rules to the detected one or more potential B-line objects to identify one or more potential B-lines in the at least one ultrasound video. For example, FIG. 2, e.g., FIG. 2A, shows B-line detection rule application circuit 268 to apply one or more B-line detection rules to the detected one or more potential B-line objects, in both the vertical Q-mode map (e.g., which may be better for detecting merged or persistent B-lines) and the baseline-adjusted vertical Q-mode map (e.g., which may be better for detecting transient, faint, or briefly-appearing B-lines) to identify one or potential B-lines in the at least one ultrasound video. As will be discussed in more detail herein, the image may be thresholded according to one or more rules, and then objects in the vertical Q-mode map that survive thresholding may be clustered or otherwise selected and/or grouped for image extraction from the ultrasound video at the location specified by the detection, in a process that will be described in more detail herein. The thresholding operations and graphs of various threshold selections and ROC (receiver operating characteristic)/free ROC (fROC) curves are shown in FIG. 18 and will be discussed in more detail herein.

Figure 15B:
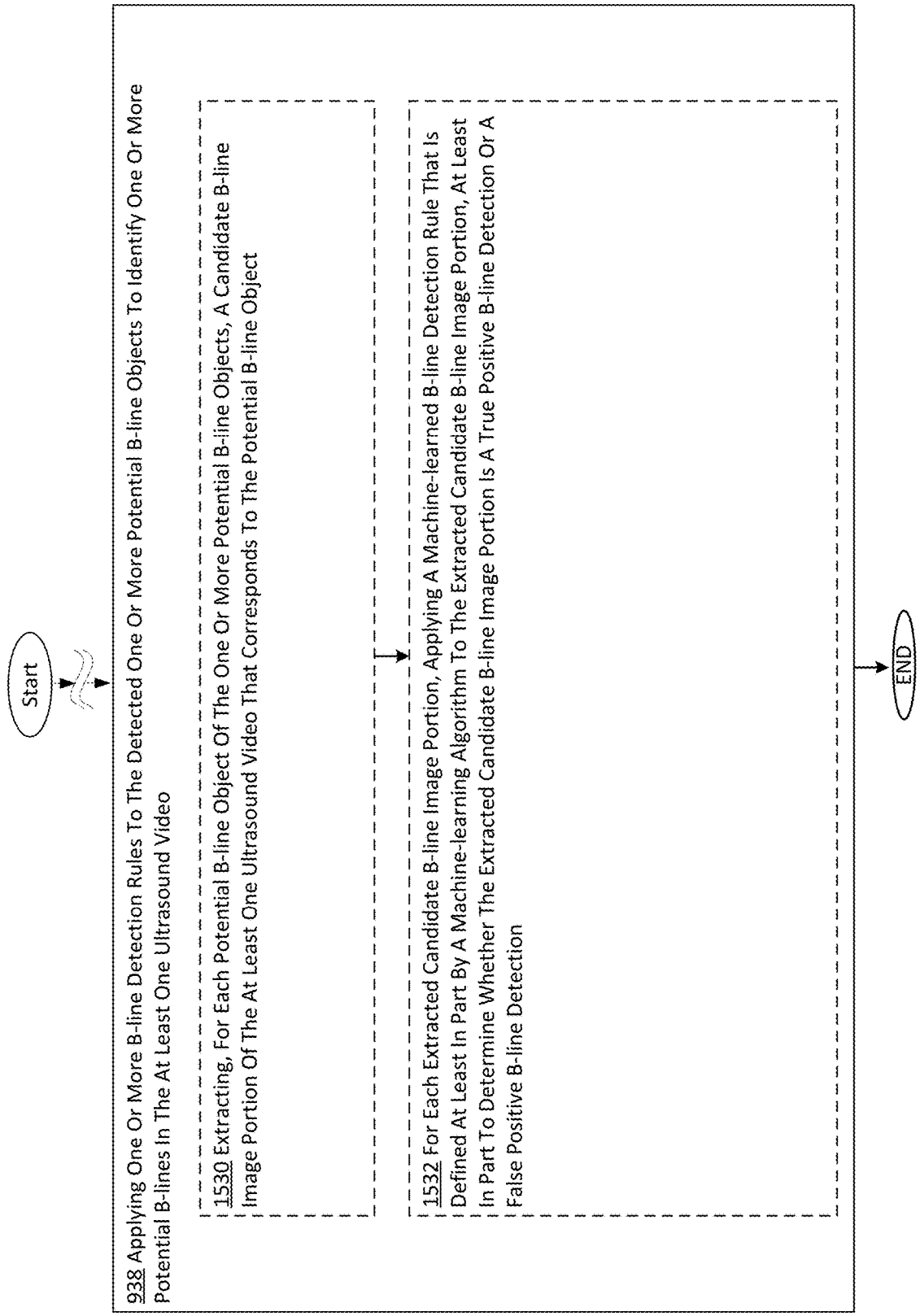
FIG. 15B is a high-level logic flowchart of an applying one or more B-line detection rules operation 938, according to embodiments of the invention.

Referring now to FIG. 15B, in an implementation, operation 938 (from FIG. 9B), may include operation 1530 depicting extracting, for each potential B-line object of the one or more potential B-line objects, a candidate B-line image portion of the at least one ultrasound video that corresponds to the potential B-line object. That is, each potential B-line object of the one or more potential B-line objects that is present in the vertical Q-mode image or the baseline-adjusted vertical Q-mode image, represents a location (e.g., frame and column) in the ultrasound video. In an implementation, referring to FIG. 18, the annotated thresholded vertical Q-mode map 1810 shows various "bands" around the asterisked areas, e.g., labeled as "2" and "3." These bands represent areas where pixel intensity data is still present after thresholding of the vertical Q-mode map. In an implementation, some portion of these bands is used as an "address" (e.g., column and frame number) of the ultrasound video, to extract that portion of the ultrasound video, to perform further B-line detection on the actual video data, to determine whether the potential B-line object that is detected is a true positive B-line or a false positive generated by a different artifact. In an implementation, each of the band areas is treated as a potential B-line object. In another implementation, the bands of post-thresholding data are consolidated into a midpoint location, represented by the black asterisks in areas 2 and 3 of thresholded vertical Q-mode map 1810. In this implementation, the black asterisks represent the address, e.g., column and frame number, of the candidate B-line image portion that will be extracted from the ultrasound video. For example, in an implementation, one of the black asterisks may represent column 100, frame 55 (these numbers are hypothetical). In that instance, the image data from column 100, frame 55 will be extracted from the ultrasound video as the candidate B-line image portion, to which a machine-learning algorithm will be applied to determine whether it is a true B-line. Of course, in other implementations, it may be useful to extract the surrounding areas of the frame, e.g., extracting columns 90-110 (e.g., ten columns in either direction around column 100 of frame 55), for the candidate B-line portion, to improve the usefulness and accuracy of the machine-learning algorithm. In an implementation, the number of surrounding columns of the frame that are to be extracted may be a predetermined number, and in other implementations, the number of surrounding columns of the frame that are to be extracted may be based on data extracted from the thresholded vertical Q-mode map (e.g., the wider the band of remaining thresholded data, the more columns of the image are extracted for the candidate B-line portion).

Referring again to FIG. 15B, in an implementation, operation 938 also may include operation 1532 depicting that, for each extracted candidate B-line image portion, applying a machine-learned B-line detection rule that is defined at least in part by a machine-learning algorithm to the extracted candidate B-line image portion, at least in part to determine whether the extracted candidate B-line image portion is a true positive B-line detection or a false positive B-line detection. For example, in an implementation, the one or more B-line detection rules may define one or more characteristics of what a B-line object looks like, that can be applied to the thresholded baseline-adjusted vertical Q-mode image. These characteristics may be built up from a training set, and may be adaptive (e.g., deep machine learning techniques, decision trees, neural networks, etc.). The characteristics may include a minimum and maximum height (distance) for a detected B-line and a minimum and maximum angle for the detected B-line. It is also noted that these same characteristics may be applied to B-line object candidates, e.g., the objects themselves that appear in the thresholded baseline-adjusted vertical Q-mode image, rather than the characteristics that these B-line object candidates represent in the potential B-lines in the ultrasound image.

Figure 15C:
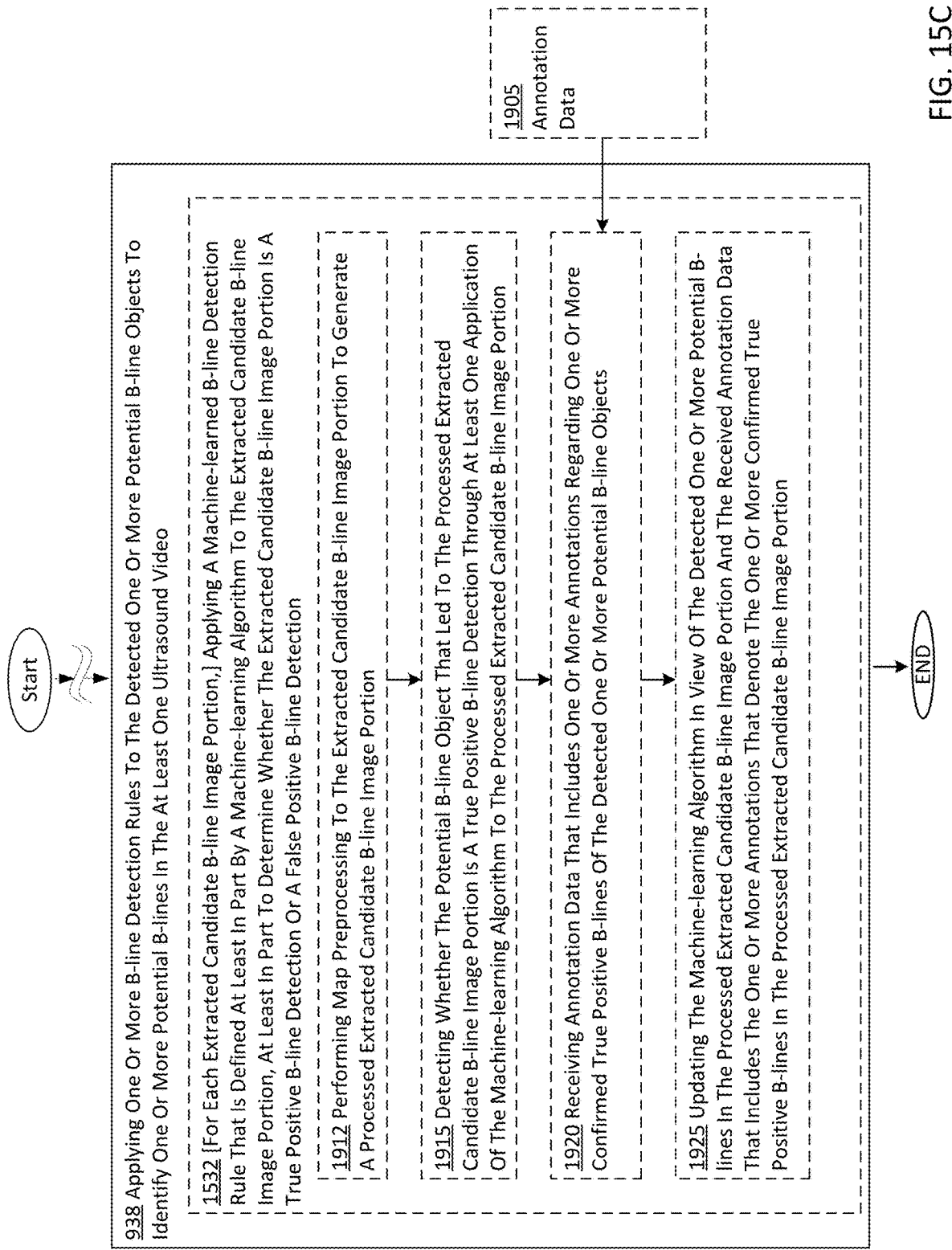
FIG. 15C is a high-level logic flowchart of an applying one or more B-line detection rules operation 938, including operation 1532, according to embodiments of the invention.
Figure 15D:
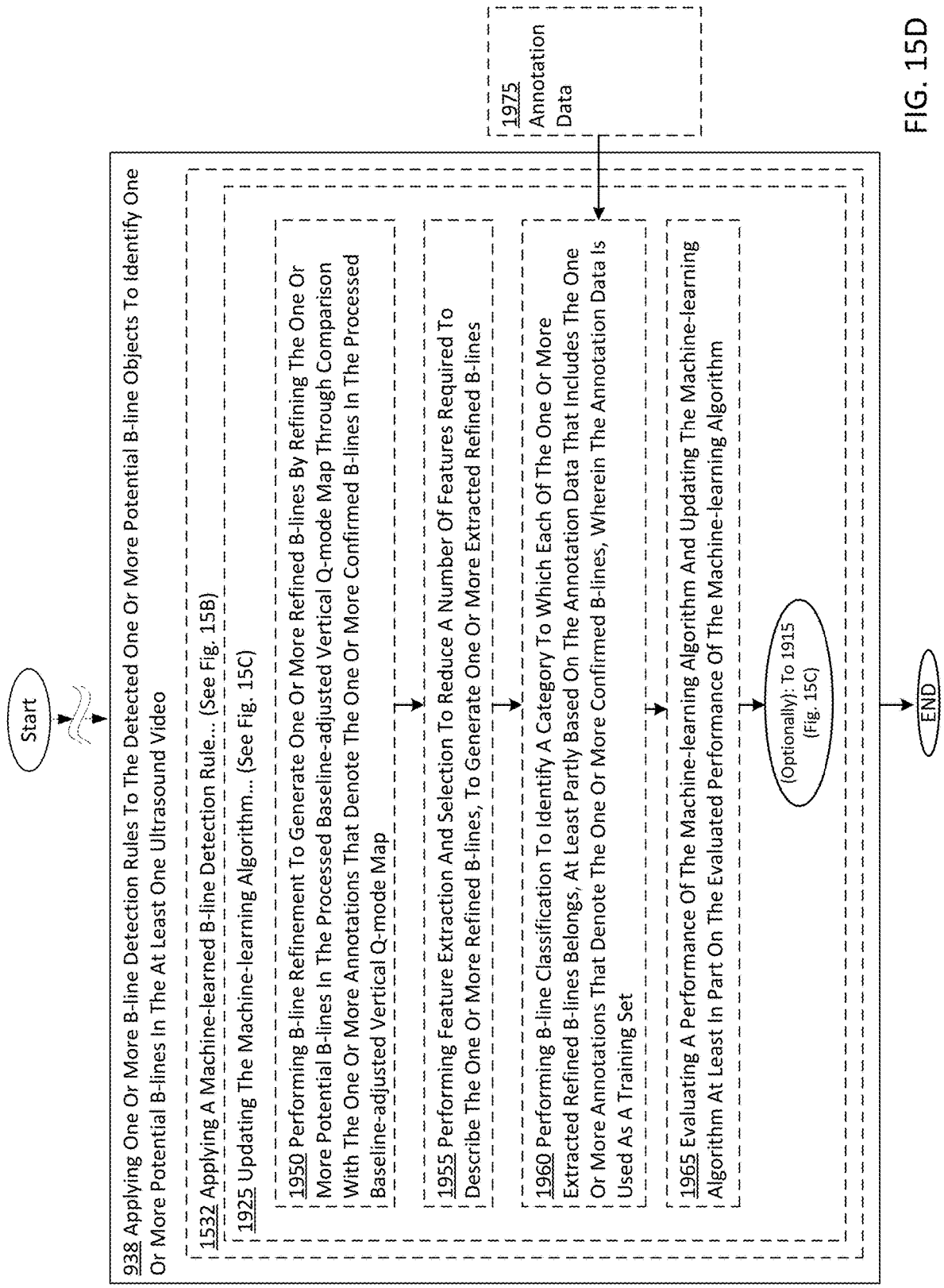
FIG. 15D is a high-level logic flowchart of an updating the machine learning algorithm operation 1925 (which is a sub-operation of operation 1532, which is a sub-operation of operation 938), according to embodiments of the invention.

Referring now to FIGS. 15C and 15D, FIGS. 15C and 15D show various implementations of operation 938 depicting applying one or more B-line detection rules to the detected one or more potential B-line objects to identify one or more potential B-lines in the at least one ultrasound video, specifically various implementations of operation 934 that use machine learning and/or a machine-learning algorithm for improved detection of potential B-lines that have been extracted from the ultrasound video, e.g., as described in operations 1530 and 1532 of FIG. 15B. For example, in an implementation, FIG. 15C shows an implementation of operation 938 that includes operation 1532 depicting that, for each extracted candidate B-line image portion, applying a machine-learned B-line detection rule that is defined at least in part by a machine-learning algorithm to the extracted candidate B-line image portion, at least in part to determine whether the extracted candidate B-line image portion is a true positive B-line detection or a false positive B-line detection. For example, as shown in FIG. 15C, a machine-learned B-line detection rule, e.g., a rule defined to detect potential B-lines in the extracted candidate B-line image portion, may be defined by a machine-learning algorithm that uses, e.g., training set data and other machine learning techniques to detect and identify potential B-lines in the extracted candidate B-line image portion, which were specified by the detection performed on the various vertical Q-mode maps, as previously described.

Referring again to FIG. 15C, in an implementation, operation 1910 may include operation 1912 depicting performing map preprocessing to the extracted candidate B-line image portion to generate a processed extracted candidate B-line image portion. For example, in an implementation, prior to execution of, or in concert with the machine-learning algorithm, the extracted candidate B-line image portion may undergo various "preprocessing" directives to prepare for execution of the machine-learning algorithm. Although FIG. 15C and this associated description use the term preprocessing, that term is relative only to the machine-learning algorithm, as other processing may have taken place on the extracted candidate B-line image portion. In an implementation, map preprocessing may include one or more image processing functions, including but not limited to, image enhancement, image denoising, image sharpening, image smoothing, image feature adjustment, and/or one or more image transformation algorithms.

Referring again to FIG. 15C, in an implementation, operation 1910 may include operation 1915 depicting detecting whether the potential B-line object that led to the processed extracted candidate B-line image portion is a true positive B-line detection through at least one application of the machine-learning algorithm to the processed extracted candidate B-line image portion. In an implementation, the machine-learning algorithm may detect the one or more potential B-lines in the processed extracted candidate B-line image portions, using one or more tools such as pattern recognition, feature detection, edge detection, novelty detection, and outlier detection. In various implementations, as will be described in more detail with respect to FIG. 15D, in an implementation, the machine-learning algorithm may be improved based on the performed detection, and thus may be iterated, e.g., the machine-learning algorithm may be performed multiple times, e.g., as described in "at least one application of the machine-learning algorithm."

Referring again to FIG. 15C, in an implementation, operation 1910 may include operation 1920 depicting receiving annotation data that includes one or more annotations regarding one or more confirmed true positive B-lines of the detected one or more potential B-line objects. For example, in an implementation, after the machine-learning algorithm has detected the B-lines from the processed extracted candidate B-line image portions, annotation data may be received that includes one or more annotations regarding one or more confirmed B-lines in the baseline-adjusted vertical Q-mode map, so that the algorithm can compare the results from detection in the processed extracted candidate B-line image portions with the annotations of the vertical Q-mode maps. This annotation data, e.g., annotation data 1905 of FIG. 15C, may be data that marks where confirmed B-lines are in the processed baseline-adjusted vertical Q-mode map, as shown in the blue asterisks of thresholded vertical Q-mode map 1810 of FIG. 18. In another implementation, not pictured herein, the annotation data may be data that indicates where confirmed B-lines are in the original ultrasound video, and various processing may be performed to determine where the confirmed B-lines would be present in the processed baseline-adjusted vertical Q-mode map. The annotation data 1905 may come from a specialist, e.g., operator/specialist 140 of FIG. 1, from remote data stored at a remote server, e.g., server 10, from a remote specialist viewing the data remotely from the subject 150, or from a different algorithm or process through which automated B-line detection is performed, e.g., a confirmed process. In an implementation, the annotation data 1905 may be training data for which the location of various confirmed B-lines is already known and stored, e.g., inside device memory 245 of FIG. 2A, or inside server 10 of FIG. 1.

Referring again to FIG. 15C, in an implementation, operation 1910 may include operation 1925 depicting updating the machine-learning algorithm in view of the detected one or more potential B-lines in the processed extracted candidate B-line image portion and the received annotation data that includes the one or more annotations that denote the one or more confirmed true positive B-lines in the processed extracted candidate B-line image portion. For example, in an implementation, the machine-learning algorithm may be updated in view of the detected one or more potential B-lines, e.g., through a process that will be described in more detail herein with respect to FIG. 15D. Specifically, the machine-learning algorithm may be updated in view of the detected potential B-lines in the processed extracted candidate B-line image portion that were extracted at locations specified by the various vertical Q-mode maps, e.g., the baseline-adjusted vertical Q-mode map, as well as in view of the annotation data 1905, which may include reference to one or more confirmed B-lines in the baseline-adjusted vertical Q-mode map, as shown in 1810 of FIG. 18.

Referring now to FIG. 15D, FIG. 15D shows more specific details about operation 1925 of FIG. 15C, e.g., updating the machine-learning algorithm in view of the detected one or more potential B-lines in the processed extracted candidate B-line image portion and the received annotation data that includes the one or more annotations that denote the one or more confirmed true positive B-lines in the processed extracted candidate B-line image portion. For example, as shown in FIG. 15D, operation 1925 may include operation 1950 depicting performing B-line refinement to generate one or more refined B-lines by refining the one or more potential B-lines in the processed extracted candidate B-line image portion at least partially through comparison with the one or more annotations that denote the one or more confirmed true positive B-lines in the processed extracted candidate B-line image portion. For example, in an implementation, part of the updating the machine-learning algorithm includes generating one or more refined B-lines through performance of B-line refinement, e.g., refining the definition of the detected B-lines. This refinement may be accomplished through a variety of known algorithms, and may be performed at least partially through comparison with the one or more annotations that denote the one or more confirmed B-lines. For example, if the annotation data defines the confirmed B-line in a slightly different way than the detection of the potential B-line, then the detected potential B-line is refined into a refined B-line through use of the annotation data, to more closely match the confirmed B-line specified by the annotation data.

Referring again to FIG. 15D, in an implementation, operation 1925 may include operation 1955 depicting performing feature extraction and selection, which may have a result of reducing a number of features required to describe the one or more refined B-lines, to generate one or more extracted refined B-lines. For example, in an implementation, the one or more refined B-lines may be described by a number of features, e.g., in a data structure which may interact with the machine-learning algorithm, in part. In an implementation, the feature extraction may be performed on the various one or more refined B-lines in order to extract the features from the refined B-lines. Then, feature selection may be applied to the extracted features, which may have the effect of reducing the number of features that are required to describe the one or more refined B-lines. In an implementation, the feature extraction and selection may build derived features of the refined B-lines, so that the refined B-lines may have a smaller dimensionality, be easier to classify, and/or be more accurate in recognition. In another implementation, the feature extraction and selection may include feature selection, e.g., selecting or determining a subset of the number of features required to describe the one or more refined B-lines, to simplify or reduce a size or complexity of the one or more extracted refined B-lines. In an implementation, various feature extraction and selection techniques relevant to image processing of grayscale images may be used, e.g., zoning, geometric moment calculation, template matching, unitary transforms, and/or Zernike moments. In other implementations, other feature extraction and selection techniques, not limited to those relevant for image processing of grayscale images, may be implemented and utilized.

Referring again to FIG. 15D, in an implementation, operation 1925 may include operation 1960 depicting performing B-line classification to identify a category to which each of the one or more extracted refined B-lines belongs, at least partly based on the annotation data that includes the one or more annotations that denote the one or more confirmed true positive B-lines, wherein the annotation data is used as a training set. For example, in an implementation, in a process that works closely with the feature extraction and selection described with respect to operation 1955, the extracted, refined B-lines may be classified, e.g., identified in one or more categories to which the extracted, refined B-lines, or their set of features used to define them in the machine-learning algorithm, belong. The refined B-lines may be analyzed using one or more classification algorithms, e.g., classifiers. In various implementations, the classification may be done in conjunction with the annotation data, e.g., annotation data 1975, as shown in FIG. 15D. In an implementation, annotation data 1975 of FIG. 15D is the same as annotation data 1905 of FIG. 15C, but this is not necessarily the case and may not be true across all implementations. The B-line classification may include binary or multiclass classification. In an implementation, the B-line classification may include one or more linear classifiers, one or more decision trees, one or more neural networks, or other supervised learning algorithms in which the annotation data, e.g., annotation data 1975 is used as a training set of data.

Referring again to FIG. 15D, in an implementation, operation 1925 may include operation 1965 depicting evaluating a performance of the machine-learning algorithm and updating the machine-learning algorithm at least in part on the evaluated performance of the machine-learning algorithm. In an implementation, evaluation of the performance of the machine learning algorithm, or portions of the machine learning algorithm, e.g., the classification (which, in some implementations, may be closely connected to the feature extraction and selection), may be performed using various techniques. In an implementation, evaluation may focus on precision, e.g., a number of true positives of B-line detection divided by a sum of the number of true positives and false positives, and/or recall, e.g., a number of true positives of B-line detection divided by the total number of B-lines actually present in the image, e.g., which may be determined from the annotation data. In another implementation, evaluation may be performed through calculation of various ROC and free ROC curves (e.g., as previously discussed elsewhere in this document). In another implementation, an outcome of the evaluation may lead to one or more decision branches regarding updating of the machine-learning algorithm. In an implementation, as shown in FIG. 15D, after the machine-learning algorithm is updated, the operation 1910, including operation 1915, e.g., detecting one or more potential B-lines in the processed baseline-adjusted vertical Q-mode map through at least one application of the machine-learning algorithm to the processed baseline-adjusted vertical Q-mode map, may operate again, e.g., as another application of the machine-learning algorithm to the processed baseline-adjusted vertical Q-mode map.

Figure 10A:
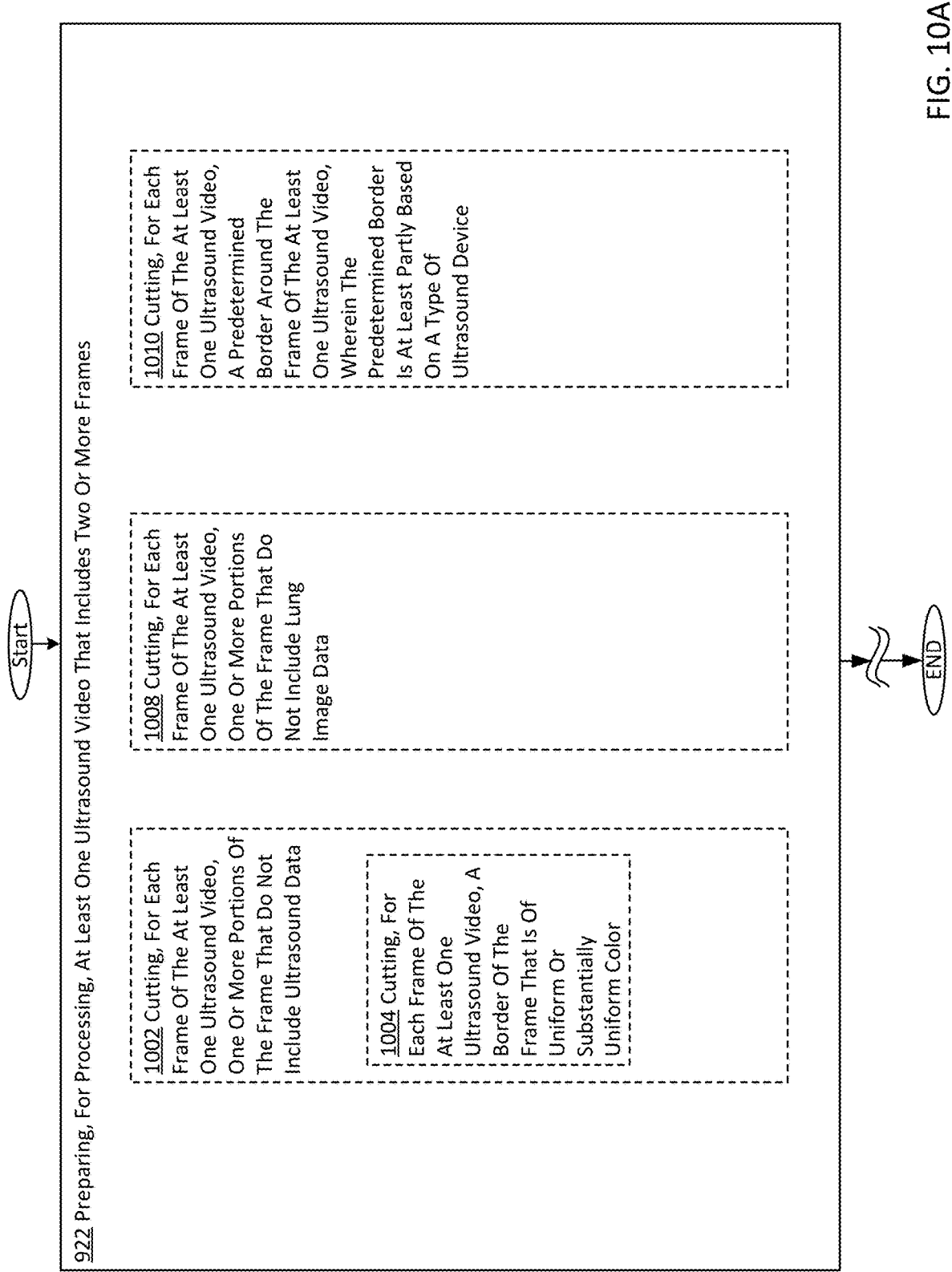
FIGS. 10A-10B, is a high-level logic flowchart of preparing for processing operation 922, according to embodiments of the invention.

Referring now to FIG. 10A, various additional implementations of operation 922, e.g., preparing, for processing, at least one ultrasound video that includes two or more frames, are discussed. For example, in an implementation, operation 922 may include operation 1002 depicting cutting, for each frame of the at least one ultrasound video, one or more portions of the frame that are determined to be absent of usable ultrasound data. In an implementation, the one or more portions of the frame that do not include ultrasound data may include borders, edges, complete dark spots, a predefined area, etc., or may be calculated through use of machine vision and machine learning/image processing techniques, or a combination thereof. In an implementation, operation 1002 may include operation 1004 depicting cutting, for each frame of the at least one ultrasound video, a border of the frame that is of uniform or substantially uniform color. For example, in an implementation, if a border of the frame is all black (e.g., zero pixel intensity) for, e.g., a distance of 50 pixels, it may be reasonably determined that this border of the frame does not include ultrasound data, and it can be removed, or cut, from the ultrasound video. The previous example is a simple one provided for clarity purposes, as more complex edge or border detection may be performed.

Referring again to FIG. 10A, in an implementation, operation 922 may include operation 1008 depicting cutting, for each frame of the at least one ultrasound video, one or more portions of the frame that do not include lung image data. Such portions of the frame may be determined by a human operator, e.g., operator 140, operating the device, with a pen, touchscreen, mouse, or other input component, or by machine algorithm, e.g., edge detection, or by predetermined rule (e.g., a specific probe leads to specific portions of the frame being cut). Referring again to FIG. 10A, in an implementation, operation 922 may include operation 1010 depicting cutting, for each frame of the at least one ultrasound video, a predetermined border around the frame of the at least one ultrasound video, wherein the predetermined border is at least partly based on a type of ultrasound device. For example, in an implementation, each various ultrasound device may have a different set of parameters that determines where the predetermined border falls. This set of parameters may be predetermined and stored on the device, or retrieved from a network, either remote or local, for example.

Figure 10B:
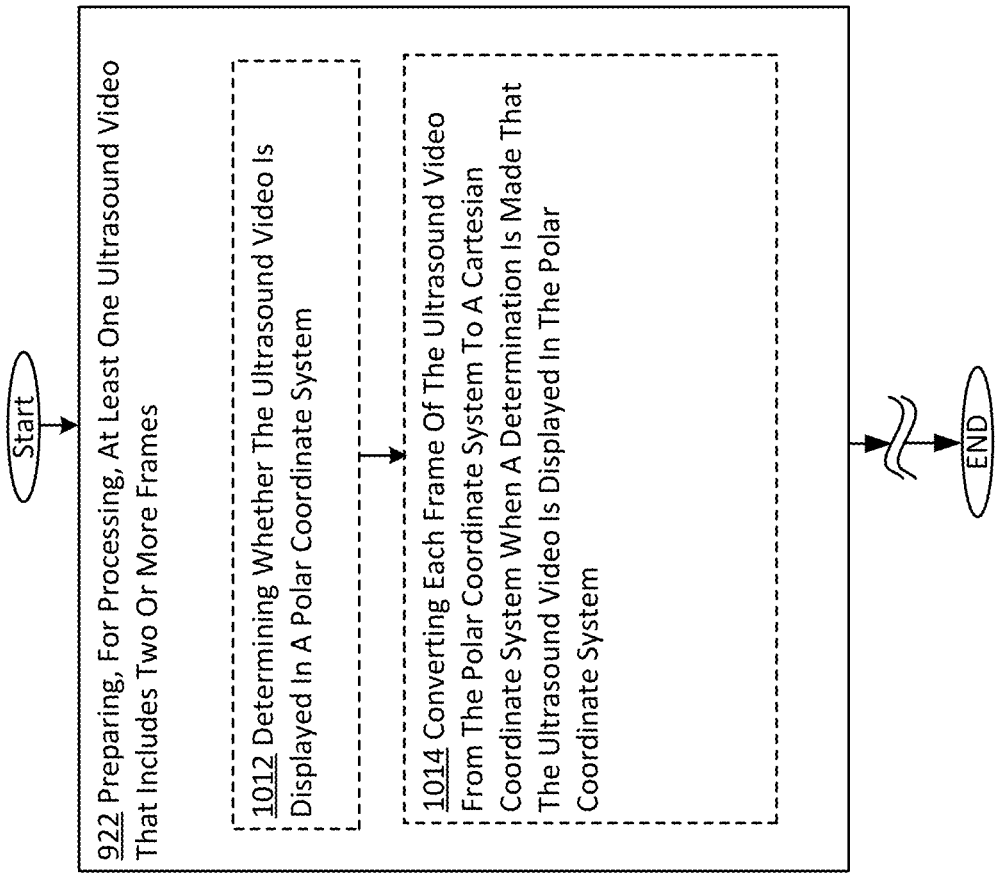

Referring now to FIG. 10B, in an implementation, operation 922 may include operation 1012 depicting determining whether the ultrasound video is displayed in a polar coordinate system. For example, this determination may be made based upon one or more characteristics of the image, e.g., fewer pixels near the top of the image, or based upon information that is received regarding the type of ultrasound device that is used, or based on a selector switch operated by a human operator to toggle the machine between "polar" and "Cartesian" coordinate systems.

Referring again to FIG. 10B, in an implementation in which operation 922 includes operation 1012, operation 922 also may include operation 1014 depicting converting each frame of the ultrasound video from the polar coordinate system to a Cartesian coordinate system when a determination is made that the ultrasound video is displayed in the polar coordinate system. For example, FIG. 4C shows chopped ultrasound image 420, which is a lung ultrasound plotted on a polar coordinate plane. In an implementation, e.g., in an implementation in which a curvilinear probe is used to generate a polar-coordinate image or video, a coordinate transform is performed to arrive at ultrasound image 430, which has had the polar coordinates converted to a Cartesian coordinate plane. In an implementation, this operation may be carried out by re-plotting the pixels to a new coordinate plane, interpolating pixels in portions of the image (e.g., near the top), where pixel data may not be explicitly located, and/or averaging pixels in portions of the image where there is more pixel data than can be plotted (e.g., near the bottom). Any number of known image processing techniques may be used to convert the polar coordinate to the Cartesian coordinates, as well as to fill in any gaps or condense any image data as necessary.

Figure 12:
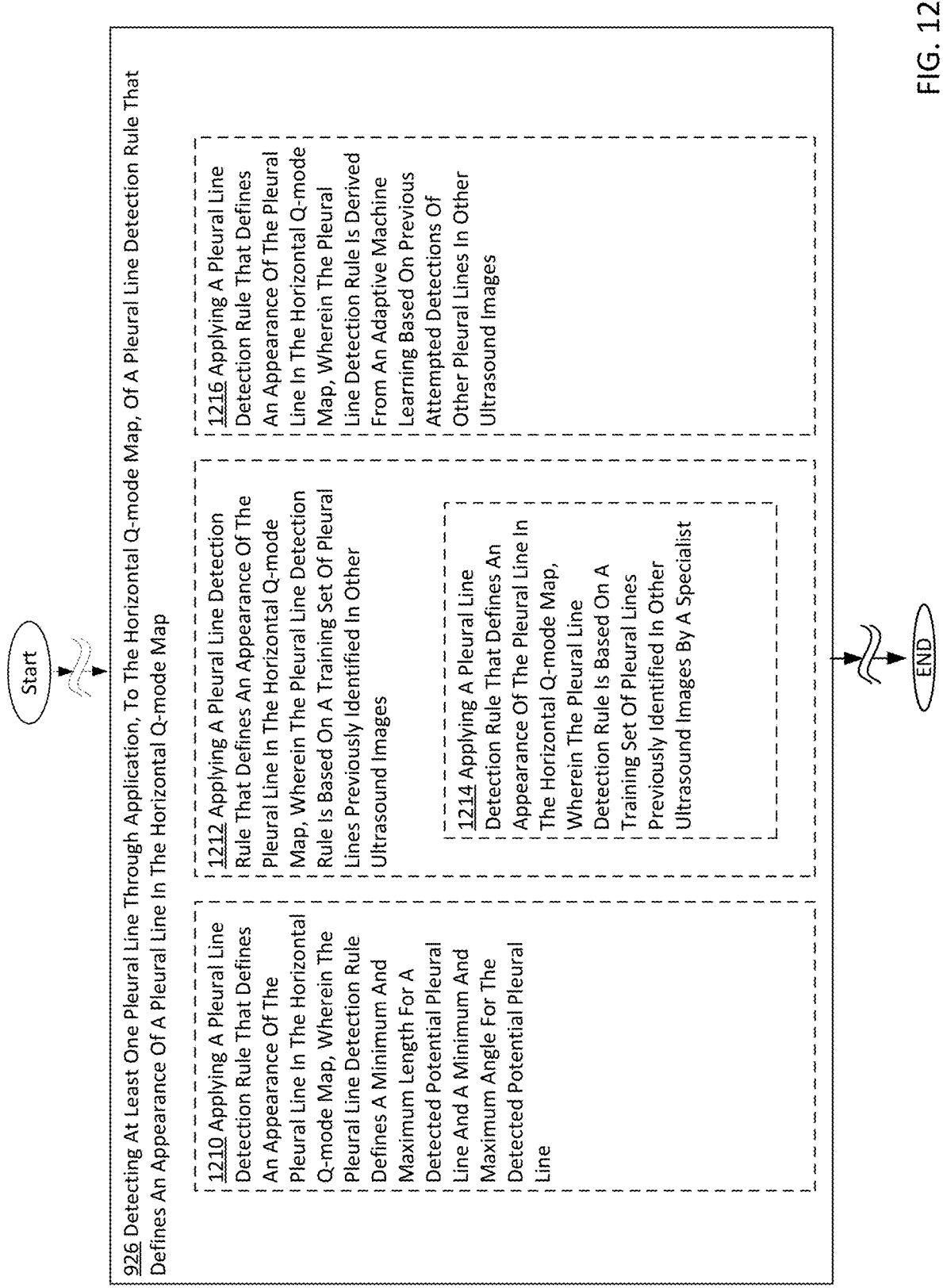
FIG. 12 is a high-level logic flowchart of a detecting at least one pleural line operation 926, according to embodiments of the invention.

Referring now to FIG. 12, FIG. 12 depicts various implementations of operation 926, e.g., detecting at least one pleural line through application, to the horizontal Q-mode map, of a pleural line detection rule that defines an appearance of a pleural line in the horizontal Q-mode map. For example, in an implementation, operation 926 may include operation 1210 depicting applying a pleural line detection rule that defines an appearance of the pleural line in the horizontal Q-mode map, wherein the pleural line detection rule specifies one or more expected characteristics of the pleural line as it appears in the horizontal Q-mode map, such as distance extended by the pleural line representation and intensity of the pleural line representation. It is noted that the various minimum and maximum length minimum and maximum angle, and minimum and maximum width, may refer to the actual properties of the pleural line in one or more frames of the ultrasound video, or the object created in the horizontal Q-mode image that represents the one or more potential pleural lines.

Referring again to FIG. 12, in an implementation, operation 926 may include operation 1212 depicting applying a pleural line detection rule that defines an appearance of the pleural line in the horizontal Q-mode map, wherein the pleural line detection rule is based on a training set of pleural lines previously identified in other ultrasound images. For example, the pleural line detection rule may be an adaptive decision tree that is based on a training set of many different pleural lines, which may be filtered for specific lung characteristics that may generate pleural lines with specific corresponding characteristics. In another implementation, operation 1212 may include operation 1214 depicting applying a pleural line detection rule that defines an appearance of the pleural line in the horizontal Q-mode map, wherein the pleural line detection rule is based on a training set of pleural lines previously identified in other ultrasound images by a specialist.

Referring again to FIG. 12, in an implementation, operation 926 may include operation 1216 depicting applying a pleural line detection rule that defines an appearance of the pleural line in the horizontal Q-mode map, wherein the pleural line detection rule is derived from a machine learning algorithm that is at least partially based on evaluation of previous attempted detections of other pleural lines in other ultrasound images. For example, adaptive machine-learning techniques may be used to detect pleural lines as the machine performs more ultrasound scans, which may be useful in various implementations, e.g., in understaffed hospitals in developing countries.

Figure 17:
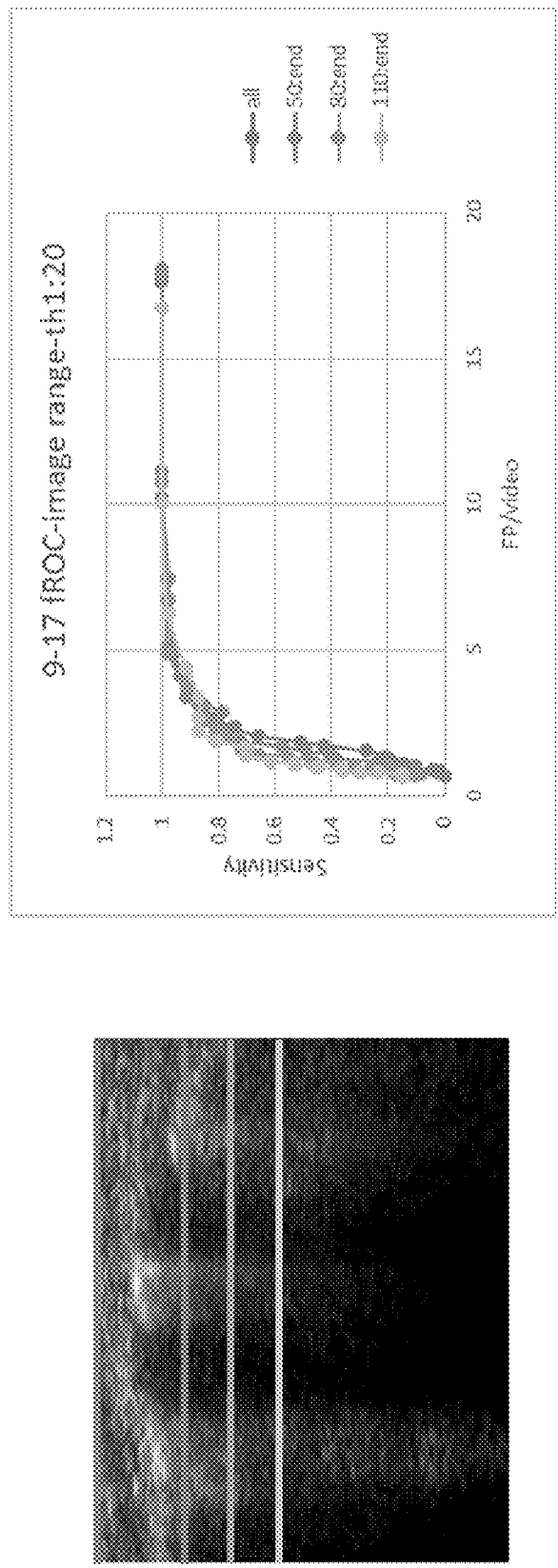
FIG. 17 shows an exemplary illustration of an effect of depth range selection on free ROC (Receiver Operating Characteristic) curves, according to various embodiments of the invention.

Referring now to FIG. 17, FIG. 17 shows the various effects of vertical depth range selection, which may, in various implementations, be based on pleural line detection in the various images. For example, referring back to FIG. 5B, FIG. 5B and its associated description provide details about the various selections of depth range, and how they may be at least partially based on the detection of the pleural line in the image. Specifically, FIG. 17 uses free ROC (e.g., receiver-operating-characteristic) curves to illustrate the impact of the various depth range selections made for an ultrasound image, e.g., the depth selections shown in FIG. 5B. As a preliminary matter, FIG. 17 shows a free ROC (also interchangeably referred to as a "free-response ROC," and interchangeably referred to herein abbreviated as "fROC"). Free-response ROC curves may be used in various implementations in which the number of potential positive detections is not known prior to analyzing the image, which is often the case with the pulmonary ultrasound images. For example, ultrasound image 1821 shows a Cartesian-coordinate ultrasound image with four different depth range cut-off lines selected (indicated in white), e.g., at 0, 50, 80, and 100. On the right, FIG. 17 shows an fROC (Free ROC) plot 1820 generated from performance of a video-based B-line detection on ultrasound image 1821, with each of the four different depth range cut-off line values plotted. That is, selection of the cut-off line in FIG. 17 directly determines the depth range, e.g., as shown in FIG. 5B.

Referring back to FIG. 13, FIG. 13 discusses the use of the vertical Q-mode image to detect certain artifacts and other objects in the ultrasound image, e.g., rib shadows. FIG. 13 describes processes for detection of rib shadows in the vertical Q-mode image, according to various implementations. For example, in an implementation, operation 928 may include operation 1320 depicting generating at least one vertical Q-mode map that is a representation of data gathered from at least one frame of the at least one ultrasound video, as shown in FIG. 13. In an implementation, when operation 928 includes operation 1320, operation 928 also may include operation 1322 depicting using the data present in the generated at least one vertical Q-mode map to mark or modify areas of the at least one ultrasound video that represent one or more rib shadows. Some of the operations in FIG. 13 are shown at least in part in FIG. 5E.

That is, referring to FIG. 5E, FIG. 5E shows a vertical Q-mode image 550 and the B-line artifacts that appear in vertical Q-mode image 550, which is oriented and aligned similarly to as described in FIGS. 3B and 3C, that is, with a top-left origin, the column position on the x-axis, and the frame number on the y-axis. In an implementation, as the soundwaves carried by the ultrasound device cannot pass through the rib cage to reach the lungs, the ribs may show up as darkened portions of the ultrasound video, e.g., as shown in the ultrasound images and vertical Q-mode images of FIG. 5E. Specifically, FIG. 5E shows frame 17 ultrasound image 551 and frame 48 ultrasound image 552, which are frames 17 and 48 of the same ultrasound video, e.g., ultrasound video 70. In an implementation, weak B-line 443 may be seen in frame 17 ultrasound image 551, and strong B-line 554 may be seen in frame 48 ultrasound image 552. As can be seen in FIG. 5E, the vertical Q-mode image 550 generated from the ultrasound video associated with ultrasound image 551 and ultrasound image 552 may generate strong "bands" of rib shadow 555, in addition to strong B-line 554 and weak B-line 553. These bands of rib shadow may be used in various algorithms to improve B-line detection, e.g., by refining B-line detections to reduce a false positive rate.

Figure 9C:
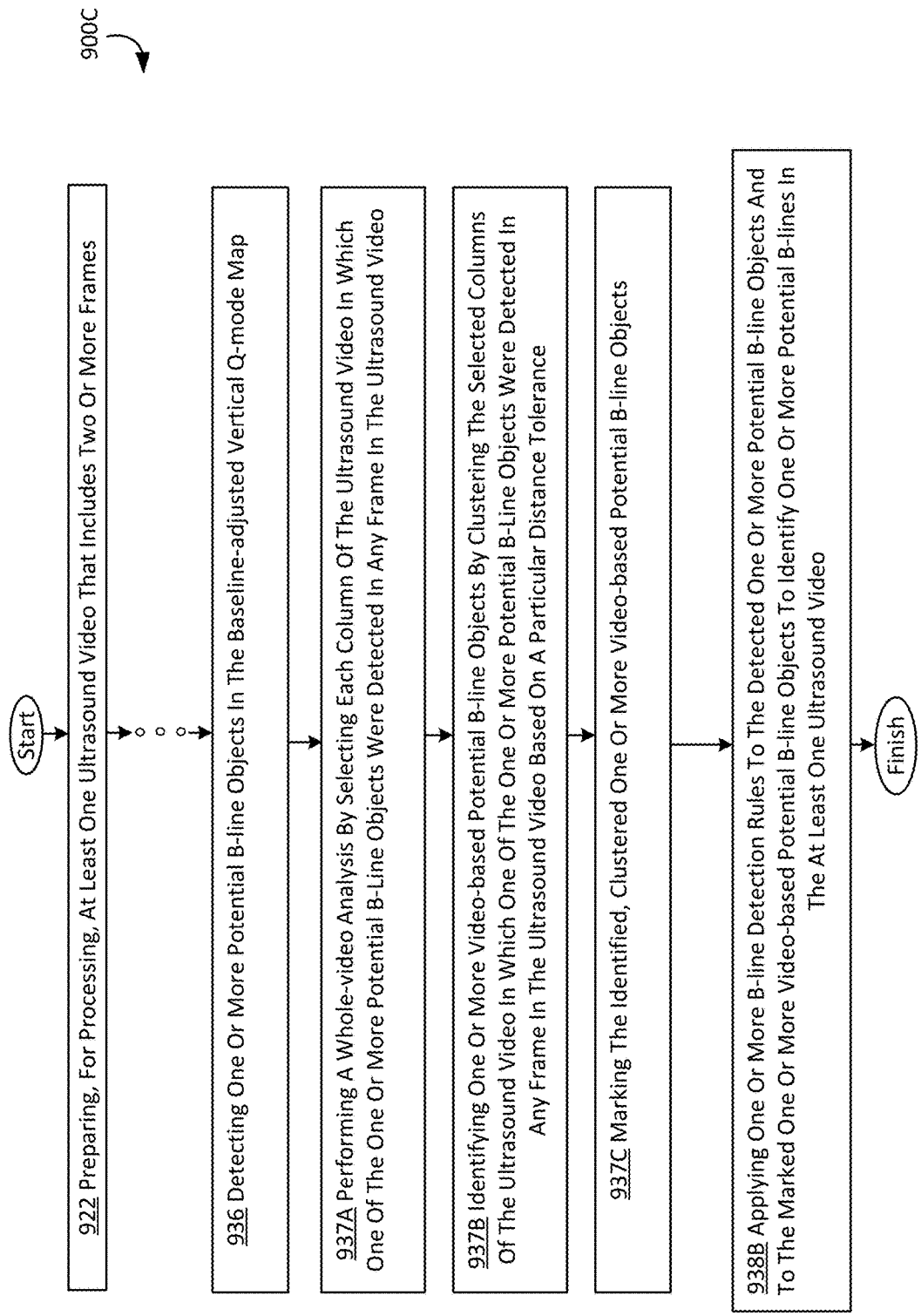
FIG. 9C is a high-level logic flowchart of a process, e.g., operational flow 900C, according to various embodiments of the invention.

In the implementations previously described, analysis of the ultrasound video was performed on a frame-by-frame basis. In other implementations, however, analysis of the ultrasound video as a whole may also be considered, in order to improve the algorithms for detecting B-lines and distinguishing false positives from true positives. Referring now to FIG. 9C, FIG. 9C depicts an operation 900C that is similar to operation 900B, except that operation 900C includes several additional operations that provide a "whole video" detection of potential B-line objects. As a visualization tool, whole-video detection of potential B-line objects is analogous to condensing the vertical Q-mode map downward into a single line (e.g., condensing the frames down), and performing detection in that manner. Another way of visualization is that, if a potential B-line object is detected in any frame of the video, which is considered a potential B-line object detection for the whole video.

Referring now to FIG. 9C, FIG. 9C and the depicted operation 900C includes the operations previously described in FIG. 9B, e.g., operation 922, 924, 926, 928, 930, 932, 934, and 936. After operation 936 is completed, however, additional operations may be carried out. For example, in an implementation, operation 900C may include operation 937A depicting performing a whole-video analysis by selecting each column of the ultrasound video where one of the one or more potential B-line objects were detected in any frame in the ultrasound video. For example, as shown in FIG. 18, the triangles at the bottom of map 1810 show the columns at which a B-line was detected at any point in the various vertical Q-mode analyses, as previously described. It is noted, however, that map 1810 shows fewer triangles than columns with asterisks (representing where a potential B-line was detected during frame-based analysis, as previously described). This apparent discrepancy is because of an operation, e.g., operation 937B of FIG. 9C, which identifies the one or more video-based potential B-line objects by clustering the selected columns of the ultrasound video in which one of the one or more potential B-line objects were detected in any frame in the ultrasound video, based on a particular distance tolerance. For example, B-line objects that are detected within a particular distance away from each other (e.g., ten columns) are treated as the same B-line object.

This distance tolerance may vary based on various algorithms applied for B-line detection and/or various rules that will be applied for B-line detection, as well as different characteristics of the image and video that are captured. For example, referring now to FIG. 18, FIG. 18 shows an annotated thresholded vertical Q-mode map 1810. The triangles near the bottom edge of annotated thresholded vertical Q-mode map 1810 represent video-based detection, and the asterisks represent frame-based detection of potential B-lines. The various video-based detections of potential B-line objects, represented by triangles, have been clustered together, based on that predefined distance tolerance value, as described above. For example, a pre-defined distance tolerance may be set, for which any identified threshold-positive areas are less than the pre-defined distance tolerance apart, are treated as a single identified potential B-line. Thus, although clustering and categorizing are mentioned in other implementations above, in this implementation, the clustering and categorizing are performed prior to B-line identification algorithms in operation 937B, e.g., the video-based B-line detection operation.

In an implementation, referring again to FIG. 18, plot 1812 shows a free ROC (fROC) plot that plots free ROC curves of the outcomes of application of the various distance tolerances, as applied to the video-based potential B-line detection, from a thresholded vertical Q-mode map on which annotated thresholded vertical Q-mode map 1810 is based. The furthest-left line (blue-grey) in plot 1812 represents a pre-defined distance tolerance of 30. The middle line (blue) in plot 1812 represents a pre-defined distance tolerance of 20, and the furthest-right line (red) in plot 1812 represents a pre-defined distance tolerance of 10.

Referring back to FIG. 9C, in an implementation, operation 900C may include operation 937C depicting marking identified, clustered one or more video-based potential B-line objects. These marks appear as red triangles in annotated thresholded vertical Q-mode map 1810 of FIG. 18. In an implementation, operation 900C includes operation 938B depicting applying one or more B-line detection rules to the detected one or more potential B-line objects and to the marked one or more video-based potential B-line objects to identify one or more potential B-lines in the at least one ultrasound video. In other words, operation 938B of operation 900C is the same as operation 938 of operation 900B, except that the marked one or more video-based potential B-line objects are also processed through application of one or more B-line detection rules, in a similar manner to as previously described with respect to operation 938.

The foregoing examples are meant to be illustrative only, and omission of an example here should not be construed as intentional or intentionally disavowing subject matter. The scope of the invention set forth herein is defined solely by the following claims at the end of this application.

V. Various Alternate Implementations and Non-Limiting Language

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory In a general sense, those skilled in the art will recognize that the various embodiments described herein can be implemented, individually and/or collectively, by various types of electro-mechanical systems having a wide range of electrical components such as hardware, software, firmware, and/or virtually any combination thereof, limited to patentable subject matter under 35 U.S.C. 101; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

For the purposes of this application, "cloud" computing may be understood as described in the cloud computing literature. For example, cloud computing may be methods and/or systems for the delivery of computational capacity and/or storage capacity as a service. The "cloud" may refer to one or more hardware and/or software components that deliver or assist in the delivery of computational and/or storage capacity, including, but not limited to, one or more of a client, an application, a platform, an infrastructure, and/or a server The cloud may refer to any of the hardware and/or software associated with a client, an application, a platform, an infrastructure, and/or a server. For example, cloud and cloud computing may refer to one or more of a computer, a processor, a storage medium, a router, a switch, a modem, a virtual machine (e.g., a virtual server), a data center, an operating system, a middleware, a firmware, a hardware back-end, a software back-end, and/or a software application. A cloud may refer to a private cloud, a public cloud, a hybrid cloud, and/or a community cloud. A cloud may be a shared pool of configurable computing resources, which may be public, private, semi-private, distributable, scalable, flexible, temporary, virtual, and/or physical. A cloud or cloud service may be delivered over one or more types of network, e.g., a mobile communication network, and the Internet.

As used in this application, a cloud or a cloud service may include one or more of infrastructure-as-a-service ("IaaS"), platform-as-a-service ("PaaS"), software-as-a-service ("SaaS"), and/or desktop-as-a-service ("DaaS"). As a non-exclusive example, IaaS may include, e.g., one or more virtual server instantiations that may start, stop, access, and/or configure virtual servers and/or storage centers (e.g., providing one or more processors, storage space, and/or network resources on-demand, e.g., EMC and Rackspace). PaaS may include, e.g., one or more software and/or development tools hosted on an infrastructure (e.g., a computing platform and/or a solution stack from which the client can create software interfaces and applications, e.g., Microsoft Azure). SaaS may include, e.g., software hosted by a service provider and accessible over a network (e.g., the software for the application and/or the data associated with that software application may be kept on the network, e.g., Google Apps, SalesForce). DaaS may include, e.g., providing desktop, applications, data, and/or services for the user over a network (e.g., providing a multi-application framework, the applications in the framework, the data associated with the applications, and/or services related to the applications and/or the data over the network, e.g., Citrix). The foregoing is intended to be exemplary of the types of systems and/or methods referred to in this application as "cloud" or "cloud computing" and should not be considered complete or exhaustive.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

To the extent that formal outline headings are present in this application, it is to be understood that the outline headings are for presentation purposes, and that different types of subject matter may be discussed throughout the application (e.g., device(s)/structure(s) may be described under process(es)/operations heading(s) and/or process(es)/operations may be discussed under structure(s)/process(es) headings; and/or descriptions of single topics may span two or more topic headings). Hence, any use of formal outline headings in this application is for presentation purposes, and is not intended to be in any way limiting.

Throughout this application, examples and lists are given, and these examples and/or lists may be delineated with parentheses, commas, the abbreviation "e.g.," or some combination thereof. Unless explicitly otherwise stated, these examples and lists are merely exemplary and are non-exhaustive. In most cases, it would be prohibitive to list every example and every combination. Thus, smaller, illustrative lists and examples are used, with focus on imparting understanding of the claim terms rather than limiting the scope of such terms.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although one or more users maybe shown and/or described herein, e.g., in FIG. 1, and other places, as a single illustrated figure, those skilled in the art will appreciate that one or more users may be representative of one or more human users, robotic users (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

VI. Preface to the Claimed Subject Matter

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

This application may make reference to one or more trademarks, e.g., a word, letter, symbol, or device adopted by one manufacturer or merchant and used to identify and/or distinguish his or her product from those of others. Trademark names used herein are set forth in such language that makes clear their identity, that distinguishes them from common descriptive nouns, that have fixed and definite meanings, or, in many if not all cases, are accompanied by other specific identification using terms not covered by trademark. In addition, trademark names used herein have meanings that are well-known and defined in the literature, or do not refer to products or compounds for which knowledge of one or more trade secrets is required in order to divine their meaning. All trademarks referenced in this application are the property of their respective owners, and the appearance of one or more trademarks in this application does not diminish or otherwise adversely affect the validity of the one or more trademarks. All trademarks, registered or unregistered, that appear in this application are assumed to include a proper trademark symbol, e.g., the circle R or bracketed capitalization (e.g., [trademark name]), even when such trademark symbol does not explicitly appear next to the trademark. To the extent a trademark is used in a descriptive manner to refer to a product or process, that trademark should be interpreted to represent the corresponding product or process as of the date of the filing of this patent application.

Throughout this application, the terms "in an embodiment," 'in one embodiment," "in some embodiments," "in several embodiments," "in at least one embodiment," "in various embodiments," and the like, may be used. Each of these terms, and all such similar terms should be construed as "in at least one embodiment, and possibly but not necessarily all embodiments," unless explicitly stated otherwise. Specifically, unless explicitly stated otherwise, the intent of phrases like these is to provide non-exclusive and non-limiting examples of implementations of the invention. The mere statement that one, some, or may embodiments include one or more things or have one or more features, does not imply that all embodiments include one or more things or have one or more features, but also does not imply that such embodiments must exist. It is a mere indicator of an example and should not be interpreted otherwise, unless explicitly stated as such.

Throughout this application, the terms "in an implementation," 'in one implementation," "in some implementations," "in several implementations," "in at least one implementation," "in various implementations," and the like, may be used. Each of these terms, and all such similar terms should be construed as "in at least one implementation, and possibly but not necessarily all implementations," unless explicitly stated otherwise. Specifically, unless explicitly stated otherwise, the intent of phrases like these is to provide non-exclusive and non-limiting examples of implementations of the invention. The mere statement that one, some, or may implementations include one or more things or have one or more features, does not imply that all implementations include one or more things or have one or more features, but also does not imply that such implementations must exist. It is a mere indicator of an example and should not be interpreted otherwise, unless explicitly stated as such.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

What is claimed is:

1. A method of detecting B-lines in ultrasound video and images, said method comprising:
    preparing, for processing, at least one ultrasound video that includes two or more frames;
    generating a horizontal Q-mode map comprising a plurality of horizontal-averaged vector representations, each corresponding to a horizontal average of a single frame of video data gathered from the at least one ultrasound video;
    detecting at least one pleural line through Application of a pleural line detection rule to the horizontal Q-mode map, wherein the pleural line detection rule defines an appearance of a pleural line in the horizontal Q-mode map;
    generating at least one vertical Q-mode map comprising a plurality of vertical-averaged vector representations, each corresponding to a vertical average of a single frame of data gathered from the at least one ultrasound video;
    detecting one or more potential B-line objects in the at least one vertical Q-mode map;
    applying a baseline adjustment rule to at least one frame of the at least one ultrasound video to generate baseline-adjusted ultrasound video data;
    generating at least one baseline-adjusted vertical Q-mode map, at least partly based on the baseline-adjusted ultrasound video data;
    detecting one or more potential B-line objects in the baseline-adjusted vertical Q-mode map; and
    applying one or more B-line detection rules to the detected one or more potential B-line objects to identify one or more potential B-lines in the at least one ultrasound video.

2. A device configured to detect B-lines in ultrasound video, said device comprising:
    a device interface component that includes one or more of a device input component and a device output component;
    a memory; and
    a processor operably coupled to the memory and configured to provide data to and from the device interface component, the processor including one or more circuits configured to include:
        an ultrasound video processing circuit that is configured to perform processing on at least one ultrasound video that includes two or more frames of ultrasound image data;
        a horizontal Q-mode map generation circuit that is configured to generate a horizontal Q-mode map comprising a plurality of horizontal-averaged vector representations, each corresponding to a horizontal average of a single frame of video data gathered from the at least one ultrasound video;
        a pleural line detection rule application circuit that is configured to detect at least one pleural line through Application of a pleural line detection rule to the horizontal Q-mode map, wherein the pleural line detection rule defines an appearance of a pleural line in the horizontal Q-mode map;
        a vertical Q-mode map generation circuit that is configured to generate a vertical Q-mode map comprising a plurality of horizontal-averaged vector representations, each corresponding to a horizontal average of a single frame of video data gathered from the at least one ultrasound video;

a potential B-line object in the vertical Q-mode map detection circuit that is configured to detect one or more potential B-line objects in the at least one vertical Q-mode map;

a baseline adjustment rule application circuit that is configured to apply a baseline adjustment rule to at least one frame of the at least one ultrasound video to generate baseline-adjusted ultrasound video data;

a baseline-adjusted vertical Q-mode map generation circuit that is configured to generate at least one baseline-adjusted vertical Q-mode map, at least partly based on the baseline-adjusted ultrasound video data;

a potential B-line object in an adjusted Q-mode map detection circuit that is configured to detect one or more potential B-line objects in the at least one baseline-adjusted vertical Q-mode map; and a B-line detection rule application circuit that is configured to apply one or more B-line detection rules to the detected one or more potential B-line objects to identify one or more potential B-lines in the at least one ultrasound video.

3. The device of claim 2, wherein said horizontal Q-mode map generation circuit comprises:

a horizontal-average column vector creation circuit that is configured to create, for each frame, a horizontal-average column vector that includes a column of averaged pixel intensities, wherein each averaged pixel intensity represents a horizontal average of pixel intensities across all columns of a corresponding row; and a horizontal Q-mode map generation circuit that is configured to generate the horizontal Q-mode map by stacking the created horizontal-average column vectors left-to-right horizontally, according to frame, from a top-left origin.

4. The device of claim 2, wherein said vertical Q-mode map generation circuit comprises:

a vertical-average row vector creation circuit that is configured to create, for each frame, a vertical-average row vector that includes a row of averaged pixel intensities, wherein each averaged pixel intensity represents a vertical average of pixel intensities along a range of rows of a corresponding column; and a vertical Q-mode map generation circuit that is configured to generate the vertical Q-mode map by stacking the created vertical-average row vectors downward vertically, according to frame, from a top-left origin.

5. The device of claim 2, wherein said baseline-adjusted vertical Q-mode map generation circuit comprises:

a baseline-adjusted vertical-average row vector creation circuit that is configured to create, for each frame, a vertical-average row vector that includes a row of averaged pixel intensities, wherein each averaged pixel intensity represents a vertical average of pixel intensities along a range of rows of a corresponding column of the baseline-adjusted ultrasound video data; and a baseline-adjusted vertical Q-mode map generation circuit that is configured to generate the baseline-adjusted vertical Q-mode map by stacking the created vertical-average row vectors downward vertically, according to frame, from a top-left origin.

6. The device of claim 2, wherein said baseline adjustment rule application circuit comprises:

a baseline intensity value-subtracted frame generation circuit that is configured to generate, for each frame of the at least one ultrasound video, a baseline intensity value-subtracted frame by subtracting, for each pixel in the frame, a baseline intensity value for that pixel location, from an actual pixel intensity for that pixel of the frame; and combining the generated baseline intensity value-subtracted frames into the baseline-adjusted ultrasound video data.

7. The device of claim 6, wherein said baseline intensity value comprises:

a median pixel intensity value for that pixel location, defined as a median value of pixel intensities of that pixel location in the frames of the at least one ultrasound video.

8. The device of claim 2, wherein said potential B-line object in the vertical Q-mode map detection circuit comprises:

a vertical Q-mode map threshold application circuit that is configured to apply a threshold to the at least one vertical Q-mode map to generate a thresholded vertical Q-mode map; and a thresholded vertical Q-mode map area marking circuit that is configured to mark one or more areas of the thresholded vertical Q-mode map that have a value greater than zero as potential B-line objects in the at least one ultrasound video.

* * * * *